(12) United States Patent
Narine et al.

(10) Patent No.: US 9,777,245 B2
(45) Date of Patent: Oct. 3, 2017

(54) METHODS OF FRACTIONATING METATHESIZED TRIACYLGLYCEROL POLYOLS AND USES THEREOF

(71) Applicant: Trent University, Peterborough (CA)

(72) Inventors: Suresh Narine, Peterborough (CA); Prasanth Kumar Sasidharan Pillai, Peterborough (CA); Shaojun Li, Peterborough (CA); Laziz Bouzidi, Peterborough (CA); Ali Mahdevari, Peterborough (CA)

(73) Assignee: Trent University, Peterborough, Ontario (CA)

( * ) Notice: Subject to any disclaimer, the term of this patent is extended or adjusted under 35 U.S.C. 154(b) by 0 days.

(21) Appl. No.: 15/005,895

(22) Filed: Jan. 25, 2016

(65) Prior Publication Data

US 2016/0312151 A1 Oct. 27, 2016

Related U.S. Application Data

(60) Provisional application No. 62/110,222, filed on Jan. 30, 2015.

(51) Int. Cl.
| | |
|---|---|
| *C07C 51/00* | (2006.01) |
| *C11C 3/00* | (2006.01) |
| *A61K 8/85* | (2006.01) |
| *C07C 67/31* | (2006.01) |
| *C08G 18/36* | (2006.01) |
| *C08L 75/04* | (2006.01) |
| *C07C 67/333* | (2006.01) |
| *C08G 18/08* | (2006.01) |

(Continued)

(52) U.S. Cl.
CPC ............ *C11C 3/00* (2013.01); *A61K 8/375* (2013.01); *A61K 8/85* (2013.01); *A61Q 19/00* (2013.01); *C07C 67/31* (2013.01); *C07C 67/333* (2013.01); *C08G 18/14* (2013.01); *C08G 18/36* (2013.01); *C08G 18/7671* (2013.01); *C08L 75/04* (2013.01); *C11C 1/005* (2013.01); *C11C 3/006* (2013.01); *A61K 2800/10* (2013.01); *C08G 2101/0008* (2013.01); *C08G 2101/0025* (2013.01); *C08G 2101/0083* (2013.01)

(58) Field of Classification Search
CPC .................................. C11C 3/00; A61K 8/375
USPC ........................................................ 554/149
See application file for complete search history.

(56) References Cited

U.S. PATENT DOCUMENTS

| 4,545,941 A | 10/1985 | Rosenburg |
| 5,312,940 A | 5/1994 | Grubbs et al. |

(Continued)

FOREIGN PATENT DOCUMENTS

| WO | WO2008048520 | 4/2008 | |
| WO | WO 2008048520 A2 * | 4/2008 | .......... B01J 31/2265 |

(Continued)

OTHER PUBLICATIONS

J.C. Mol. Application of olefin metathesis in oleochemistry: an example of green chemistry. Green Chem. 4:5-13, 2002.

(Continued)

*Primary Examiner* — Deborah D Carr
(74) *Attorney, Agent, or Firm* — Bereskin & Parr LLP/S.E.N.C.R.L., s.r.l.; Michael Fenwick

(57) ABSTRACT

Metathesized triacylglycerol polyols, fractionated polyol variants thereof, and their related physical and thermal properties are disclosed.

20 Claims, 32 Drawing Sheets

(51) Int. Cl.
*C08G 18/76* (2006.01)
*C11C 1/00* (2006.01)
*A61K 8/37* (2006.01)
*A61Q 19/00* (2006.01)
*C08G 101/00* (2006.01)

(56) References Cited

U.S. PATENT DOCUMENTS

| | | | |
|---|---|---|---|
| 5,342,909 | A | 8/1994 | Grubbs et al. |
| 5,710,298 | A | 1/1998 | Grubbs et al. |
| 5,728,785 | A | 3/1998 | Grubbs et al. |
| 5,728,917 | A | 3/1998 | Grubbs et al. |
| 5,750,815 | A | 5/1998 | Grubbs et al. |
| 5,831,108 | A | 11/1998 | Grubbs et al. |
| 5,922,863 | A | 7/1999 | Grubbs et al. |
| 6,306,988 | B1 | 10/2001 | Grubbs et al. |
| 6,414,097 | B1 | 7/2002 | Grubbs et al. |
| 6,696,597 | B2 | 2/2004 | Pederson et al. |
| 6,794,534 | B2 | 9/2004 | Grubbs et al. |
| 7,102,047 | B2 | 9/2006 | Grubbs et al. |
| 7,378,528 | B2 | 5/2008 | Herrmann et al. |
| 2009/0264672 | A1 | 10/2009 | Abraham et al. |
| 2010/0145086 | A1 | 6/2010 | Schrodi et al. |

FOREIGN PATENT DOCUMENTS

| | | |
|---|---|---|
| WO | WO2009020667 | 2/2009 |
| WO | WO2011133208 | 10/2011 |
| WO | WO2015143562 | 10/2015 |
| WO | WO2015143563 | 10/2015 |
| WO | WO2015143568 | 10/2015 |

OTHER PUBLICATIONS

Gibson and L.Tulich. Novel Synthesis of Long-chain Primary Alkyl Compounds. J. Org. Chem. 46:1821-1823, 1981.

Doyle, G. Olefin metathesis catalyzed by zero-valent, anionic group VI metal compounds. Journal of Catalysis. 30(1) (1973) 118-127.

Spronk, R. and Mol, J.C. Metathesis of 1-alkenes in the liquid phase over a $Re_2O_7/\gamma$—$Al_2O_3$ catalyst: I. Reactivity of the alkenes. Applied Catalysis. 70(1):295-306, 1991.

Harold H. Fox, Richard R. Schrock,. and Rick O'Dell. Coupling of Terminal Olefins by Molybdenum(VI) Imido Alkylidene Complexes. Organometallics 13:635-639, 1994.

K.J. Ivin and J.C. Mol. Olefin Metathesis and Metathesis Polyermization. Survey of Catalyst Systems, Chapter 2, pp. 12-49, 1997.

A. Maureen Rouhi. Olefin Metathesis and Metathesis Polymerization by Ivin and Mol (1997), and Chem. & Eng. News 80(51), Dec. 23, 2002, p. 29.

Boodhoo MV, Humphrey KL, and SS Narine, (2009) Relative Hardness of Fat Crystal Networks Using Force Displacement Curves, International Journal of Food Properties, V12, pp. 129-144.

Desroches, M. et al. From Vegetable Oils to Polyurethane: Synthetic Routes to Polyolds and Main Industrial Products. Polymer Reviews, 52:38-79, 2012.

\* cited by examiner

METHODS OF FRACTIONATING METATHESIZED TRIACYLGLYCEROL POLYOLS AND USES THEREOF

CROSS-REFERENCE TO RELATED APPLICATIONS

The present application claims the benefit of priority of U.S. Provisional Application No. 62/110,222, filed Jan. 30, 2015, which is incorporated by reference as though set forth herein in its entirety.

TECHNICAL FIELD

This application relates to metathesized triacylglycerol polyols and fractionated polyol variants thereof, and their related physical and thermal properties.

DESCRIPTION OF RELATED ART

Polyurethanes are one of the most versatile polymeric materials with regards to both processing methods and mechanical properties. Polyurethanes are formed either based on the reaction of NCO groups and hydroxyl groups, or via non-isocyanate pathways, such as the reaction of cyclic carbonates with amines, self-polycondensation of hydroxyl-acyl azides or melt transurethane methods. The most common method of urethane production is via the reaction of a polyol and an isocyanate which forms the backbone urethane group. Cross-linking agents, chain extenders, blowing agents and other additives may also be added as needed. The proper selection of reactants enables a wide range of polyurethane elastomers, sheets, foams, and the like.

Traditionally, petroleum-derived polyols have been widely used in the manufacturing of polyurethane foams. However, there has been an increased interest in the use of renewable resources in the manufacturing of polyurethane foams. This has led to research into developing natural oil-based polyols for use in the manufacturing of foams. The present effort details the synthesis of natural oil (palm oil, for example) based fractions of metathesized triacylglycerol and polyols thereof, which may be used in polyurethane applications, such as rigid and flexible polyurethane foams. The present effort also discloses physical and thermal properties of such polyols, and the formulation of polyurethane applications (such as foams) using such polyols as a component.

SUMMARY

In a first aspect, the disclosure provides methods of making a fractionated triacylglycerol polyol from palm oil, the method comprising: providing a metathesized triacylglycerol composition, which is formed by the cross-metathesis of a natural oil with lower-weight olefins, and which comprises triglyceride compounds having one or more carbon-carbon double bonds; reacting at least a portion of the carbon-carbon double bonds in the compounds comprised by the metathesized triacylglycerol composition to form a triacylglycerol polyol composition; and separating a fraction of the triacylglycerol polyol composition to form a fractionated triacylglycerol polyol composition, which comprises compounds having one or more carbon-carbon double bonds.

In a second aspect, the disclosure provides methods of forming a polyurethane composition, comprising: providing a triacylglycerol polyol and an organic diisocyanate, wherein providing the triacylglycerol polyol comprises making a triacylglycerol polyol according to the first aspect or any embodiments thereof; and reacting the triacylglycerol polyol and the organic diisocyanate to form a polyurethane composition. In some embodiments, the polyurethane composition is a polyurethane foam.

Further aspects and embodiments of the present disclosure are set forth in the Detailed Description.

BRIEF DESCRIPTION OF THE DRAWINGS

The following drawings are provided for purposes of illustrating various embodiments of the compounds, compositions, and methods disclosed herein. The drawings are provided for illustrative purposes only, and are not intended to describe any preferred compounds, preferred compositions, or preferred methods, or to serve as a source of any limitations on the scope of the claimed inventions.

DETAILED DESCRIPTION OF THE INVENTION

Figure 1:
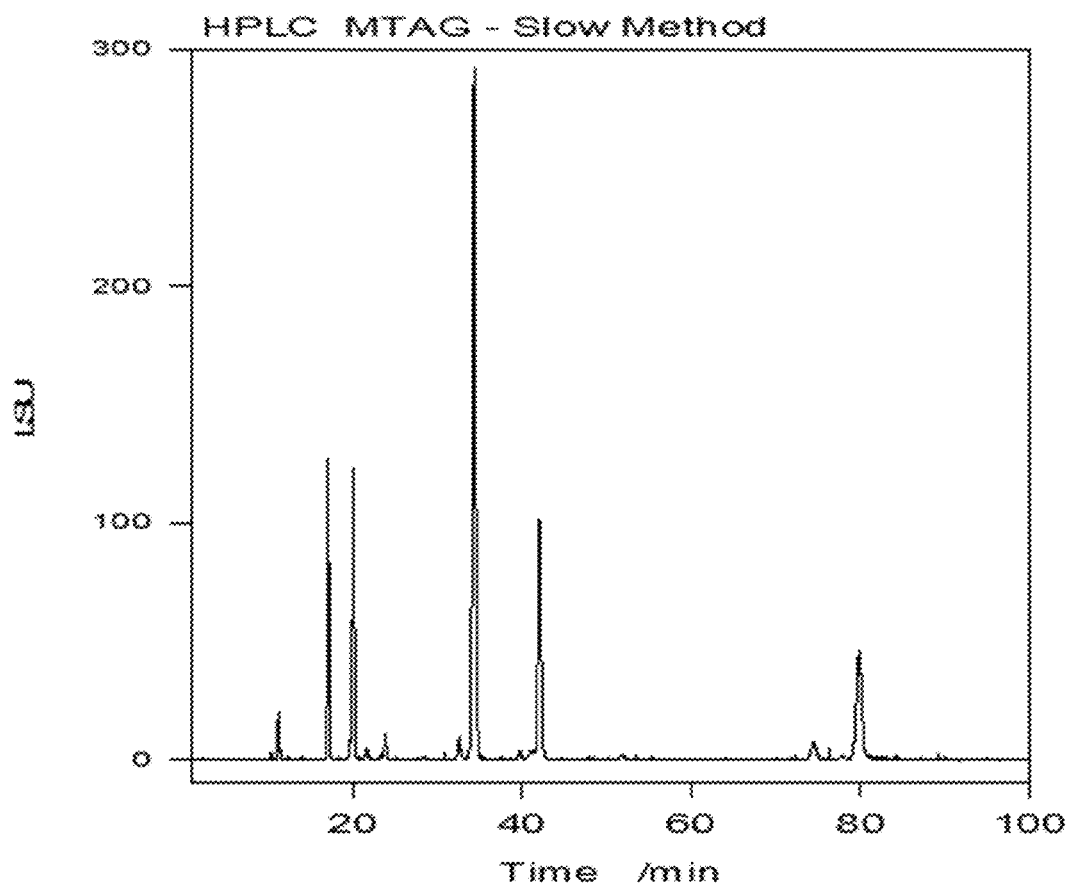
FIG. 1 depicts the HPLC of PMTAG.

The following description recites various aspects and embodiments of the inventions disclosed herein. No particular embodiment is intended to define the scope of the invention. Rather, the embodiments provide non-limiting examples of various compositions, and methods that are included within the scope of the claimed inventions. The description is to be read from the perspective of one of ordinary skill in the art. Therefore, information that is well known to the ordinarily skilled artisan is not necessarily included.

Metathesized Triacylglycerols of Natural Oils
Synthesis of Metathesized Triacylglycerols for Production of Polyols The synthesis of rigid and flexible polyurethane foams, and other polyurethanes, from natural oil based metathesized triacylglycerol (MTAG) and polyols thereof, begins with the initial synthesis of the MTAGs themselves. A general definition of a metathesized triacylglycerol is the product formed from the metathesis reaction (self-metathesis or cross-metathesis) of an unsaturated triglyceride in the presence of a metathesis catalyst to form a product comprising one or more metathesis monomers, oligomers or polymers.

Metathesis is a catalytic reaction that involves the interchange of alkylidene units among compounds containing one or more double bonds (i.e., olefinic compounds) via the formation and cleavage of the carbon-carbon double bonds. The metathesis catalyst in this reaction may include any catalyst or catalyst system that catalyzes a metathesis reaction. Generally, cross metathesis may be represented schematically as shown in Scheme 1 below:

$$R^1-CH=CH-R^2+R^3-CH=CH-R^4 \leftrightarrow R1-CH=CH-R3+R1-CH=CH-R4+R2-CH=CH-R3+R2-CH=CH-R4+R^1-CH=CH-R^1+R^2-CH=CH-R^2+R^3-CH=CH-R^3+R^4-CH=CH-R^4$$

Scheme 1. Representation of cross-metathesis reaction. Wherein $R^1$, $R^2$, $R^3$, and $R^4$ are organic groups.

Suitable homogeneous metathesis catalysts include combinations of a transition metal halide or oxo-halide (e.g., $WOCl_4$ or $WCl_6$) with an alkylating cocatalyst (e.g., $Me_4Sn$). Preferred homogeneous catalysts are well-defined alkylidene (or carbene) complexes of transition metals, particularly Ru, Mo, or W. These include first and second-generation Grubbs catalysts, Grubbs-Hoveyda catalysts, and the like. Suitable alkylidene catalysts have the general structure:

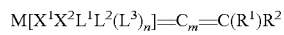

$$M[X^1X^2L^1L^2(L^3)_n]=C_m=C(R^1)R^2$$

where M is a Group 8 transition metal, $L^1$, $L^2$, and $L^3$ are neutral electron donor ligands, n is 0 (such that $L^3$ may not be present) or 1, m is 0, 1, or 2, $X^1$ and $X^2$ are anionic ligands, and $R^1$ and $R^2$ are independently selected from H, hydrocarbyl, substituted hydrocarbyl, heteroatom-containing hydrocarbyl, substituted heteroatom-containing hydrocarbyl, and functional groups. Any two or more of $X^1$, $X^2$, $L^1$, $L^2$, $L^3$, $R^1$ and $R^2$ can form a cyclic group and any one of those groups can be attached to a support.

First-generation Grubbs catalysts fall into this category where m=n=0 and particular selections are made for n, $X^1$, $X^2$, $L^1$, $L^2$, $L^3$, $R^1$ and $R^2$ as described in U.S. Pat. Appl. Publ. No. 2010/0145086 ("the '086 publication"), the teachings of which related to all metathesis catalysts are incorporated herein by reference. Second-generation Grubbs catalysts also have the general formula described above, but $L^1$ is a carbene ligand where the carbene carbon is flanked by N, O, S, or P atoms, preferably by two N atoms. Usually, the carbene ligand is part of a cyclic group. Examples of suitable second-generation Grubbs catalysts also appear in the '086 publication.

In another class of suitable alkylidene catalysts, $L^1$ is a strongly coordinating neutral electron donor as in first- and second-generation Grubbs catalysts, and $L^2$ and $L^3$ are weakly coordinating neutral electron donor ligands in the form of optionally substituted heterocyclic groups. Thus, $L^2$ and $L^3$ are pyridine, pyrimidine, pyrrole, quinoline, thiophene, or the like. In yet another class of suitable alkylidene catalysts, a pair of substituents is used to form a bi- or tridentate ligand, such as a biphosphine, dialkoxide, or alkyldiketonate. Grubbs-Hoveyda catalysts are a subset of this type of catalyst in which $L^2$ and $R^2$ are linked. Typically, a neutral oxygen or nitrogen coordinates to the metal while also being bonded to a carbon that is α-, β-, or γ- with respect to the carbene carbon to provide the bidentate ligand. Examples of suitable Grubbs-Hoveyda catalysts appear in the '086 publication.

The structures below (Scheme 2) provide just a few illustrations of suitable catalysts that may be used:

Scheme 2. Structures of few metathesis catalysts.

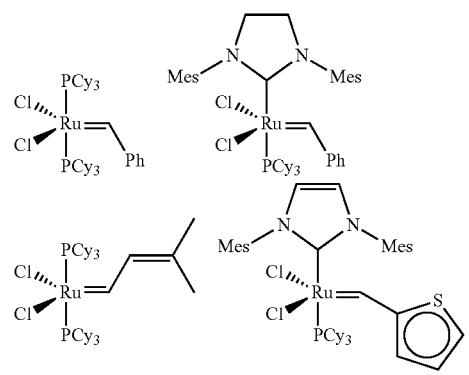

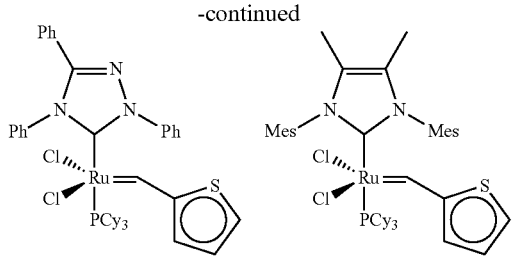

Heterogeneous catalysts suitable for use in the self- or cross-metathesis reactions include certain rhenium and molybdenum compounds as described, e.g., by J. C. Mol in *Green Chem.* 4 (2002) 5 at pp. 11-12. Particular examples are catalyst systems that include $Re_2O_7$ on alumina promoted by an alkylating cocatalyst such as a tetraalkyl tin lead, germanium, or silicon compound. Others include $MoCl_3$ or $MoCl_5$ on silica activated by tetraalkyltins. For additional examples of suitable catalysts for self- or cross-metathesis, see U.S. Pat. No. 4,545,941, the teachings of which are incorporated herein by reference, and references cited therein. See also *J. Org. Chem.* 46 (1981) 1821; *J. Catal.* 30 (1973) 118; *Appl. Catal.* 70 (1991) 295; *Organometallics* 13 (1994) 635; *Olefin Metathesis and Metathesis Polymerization* by Ivin and Mol (1997), and *Chem. & Eng. News* 80(51), Dec. 23, 2002, p. 29, which also disclose useful metathesis catalysts. Illustrative examples of suitable catalysts include ruthenium and osmium carbene catalysts as disclosed in U.S. Pat. Nos. 5,312,940, 5,342,909, 5,710,298, 5,728,785, 5,728,917, 5,750,815, 5,831,108, 5,922,863, 6,306,988, 6,414,097, 6,696,597, 6,794,534, 7,102,047, 7,378,528, and U.S. Pat. Appl. Publ. No. 2009/0264672 A1, and PCT/US2008/009635, pp. 18-47, all of which are incorporated herein by reference. A number of metathesis catalysts that may be advantageously employed in metathesis reactions are manufactured and sold by Materia, Inc. (Pasadena, Calif.).

As a non-limiting aspect, a typical route to obtain MTAG is via the cross metathesis of a natural oil with a lower weight olefin. As a non-limiting aspect, reaction routes using triolein with 1-butene and triolein with ethylene are shown below in Scheme 3a and 3b, respectively.

Scheme 3a. Metathesis reaction of triolein with 1-butene.

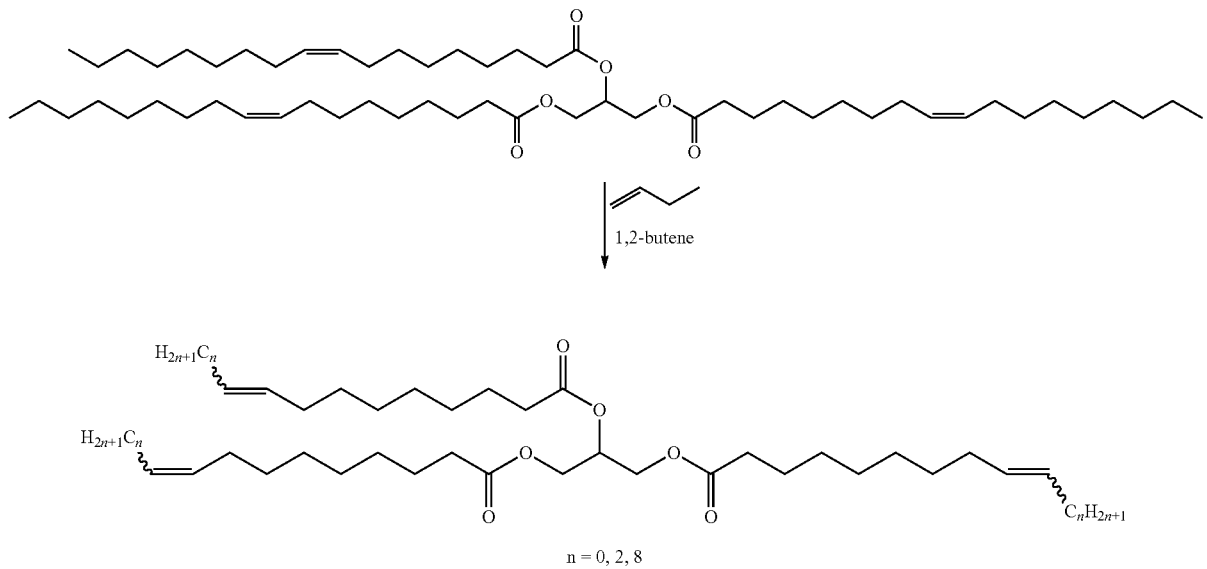

n = 0, the fatty acid is 9-denenoic acid (D), n = 2, the fatty acid is 9-dodecenoic acid (Dd) and n = 8, the fatty acid is oleic acid (O).

Scheme 3b. Metathesis reaction of triolein with ethylene.

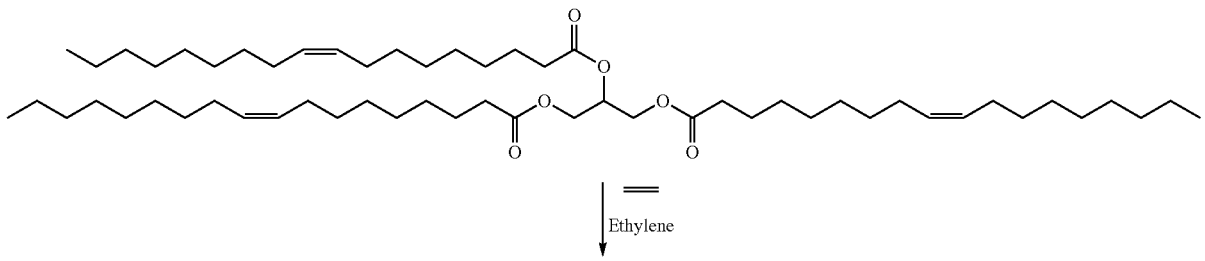

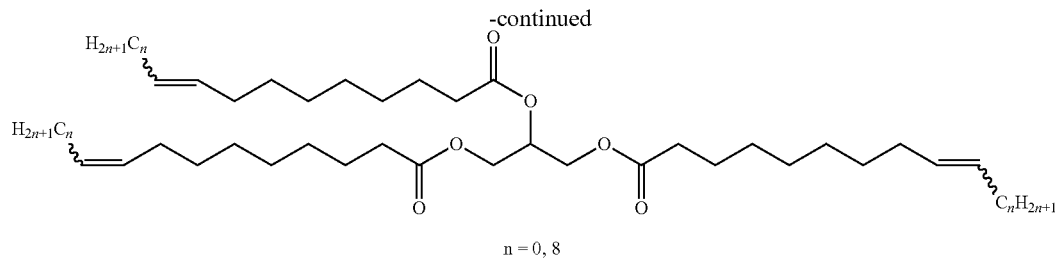

n = 0, 8 n = 0, the fatty acid is 9-denenoic acid (D), and n = 8, the fatty acid is oleic acid (O).

As used herein, the term "lower weight olefin" may refer to any one or a combination of unsaturated straight, branched, or cyclic hydrocarbons in the $C_2$ to $C_{14}$ range. Lower weight olefins include "alpha-olefins" or "terminal olefins," wherein the unsaturated carbon-carbon bond is present at one end of the compound. Lower weight olefins may also include dienes or trienes. Examples of low weight olefins in the $C_2$ to $C_6$ range include, but are not limited to: ethylene, propylene, 1-butene, 2-butene, isobutene, 1-pentene, 2-pentene, 3-pentene, 2-methyl-1-butene, 2-methyl-2-butene, 3-methyl-1-butene, cyclopentene, 1-hexene, 2-hexene, 3-hexene, 4-hexene, 2-methyl-1-pentene, 3-methyl-1-pentene, 4-methyl-1-pentene, 2-methyl-2-pentene, 3-methyl-2-pentene, 4-methyl-2-pentene, 2-methyl-3-pentene, and cyclohexene. Other possible low weight olefins include styrene and vinyl cyclohexane. In certain embodiments, it is preferable to use a mixture of olefins, the mixture comprising linear and branched low weight olefins in the $C_4$-$C_{10}$ range. In one embodiment, it may be preferable to use a mixture of linear and branched $C_4$ olefins (i.e., combinations of: 1-butene, 2-butene, and/or isobutene). In other embodiments, a higher range of $C_{11}$-$C_{14}$ may be used.

As used herein, the term "natural oil" may refer to oil derived from plants or animal sources. The term "natural oil" includes natural oil derivatives, unless otherwise indicated. Examples of natural oils include, but are not limited to, vegetable oils, algal oils, animal fats, tall oils, derivatives of these oils, combinations of any of these oils, and the like. Representative non-limiting examples of vegetable oils include canola oil, rapeseed oil, coconut oil, corn oil, cottonseed oil, jojoba oil, olive oil, palm oil, peanut oil, safflower oil, sesame oil, soybean oil, sunflower oil, linseed oil, palm kernel oil, tung oil, jatropha oil, mustard oil, camelina oil, pennycress oil, hemp oil, algal oil, and castor oil. Representative non-limiting examples of animal fats include lard, tallow, poultry fat, yellow grease, and fish oil. Tall oils are by-products of wood pulp manufacture. In certain embodiments, the natural oil may be refined, bleached, and/or deodorized. In some embodiments, the natural oil may be partially or fully hydrogenated. In some embodiments, the natural oil is present individually or as mixtures thereof.

Natural oils generally comprise triacylglycerols of saturated and unsaturated fatty acids. Suitable fatty acids may be saturated or unsaturated (monounsaturated or polyunsaturated) fatty acids, and may have carbon chain lengths of 3 to 36 carbon atoms. Such saturated or unsaturated fatty acids may be aliphatic, aromatic, saturated, unsaturated, straight chain or branched, substituted or unsubstituted and mono-, di-, tri-, and/or poly-acid variants, hydroxy-substituted variants, aliphatic, cyclic, alicyclic, aromatic, branched, aliphatic- and alicyclic-substituted aromatic, aromatic-substituted aliphatic and alicyclic groups, and heteroatom substituted variants thereof. Any unsaturation may be present at any suitable isomer position along the carbon chain as would be noted to a person skilled in the art.

Some non-limiting examples of saturated fatty acids include propionic, butyric, valeric, caproic, enanthic, caprylic, pelargonic, capric, undecylic, lauric, tridecylic, myristic, pentadecanoic, palmitic, margaric, stearic, nonadecyclic, arachidic, heneicosylic, behenic, tricosylic, lignoceric, pentacoyslic, cerotic, heptacosylic, carboceric, montanic, nonacosylic, melissic, lacceroic, psyllic, geddic, ceroplastic acids.

Some non-limiting examples of unsaturated fatty acids include butenoic, pentenoic, hexenoic, pentenoic, octenoic, nonenoic acid, decenoic acid, undecenoic acid, dodecenoic acid, tridecenoic, tetradecenoic, pentadecenoic, palmitoleic, palmitelaidic, oleic, ricinoleic, vaccenic, linoleic, linolenic, elaidic, eicosapentaenoic, behenic and erucic acids. Some unsaturated fatty acids may be monounsaturated, diunsaturated, triunsaturated, tetraunsaturated or otherwise polyunsaturated, including any omega unsaturated fatty acids.

In a typical triacylglycerol, each of the carbons in the triacylglycerol molecule is numbered using the stereospecific numbering (sn) system. Thus one fatty acyl chain group is attached to the first carbon (the sn-1 position), another fatty acyl chain is attached to the second, or middle carbon (the sn-2 position), and the final fatty acyl chain is attached to the third carbon (the sn-3 position). The triacylglycerols described herein may include saturated and/or unsaturated fatty acids present at the sn-1, sn-2, and/or sn-3 position In some embodiments, the natural oil is palm oil. Palm oil is typically a semi-solid at room temperature and comprises approximately 50% saturated fatty acids and approximately 50% unsaturated fatty acids. Palm oil typically comprises predominately fatty acid triacylglycerols, although monoacylglycerols and diacylglycerols may also be present in small amounts. The fatty acids typically have chain lengths ranging from about C12 to about C20. Representative saturated fatty acids include, for example, C12:0, C14:0, C16:0, C18:0, and C20:0 saturated fatty acids. Representative unsaturated fatty acids include, for example, C16:1, C18:1, C18:2, and C18:3 unsaturated fatty acids. As used herein, metathesized triacylglycerols derived from palm oil may be referred to interchangeably as "palm oil MTAG" or "PMTAG" or "MTAG of/from palm oil."

Palm oil is constituted mainly of palmitic acid and oleic acid with ~43% and ~41%, respectively. The fatty acid and triglyceride (TAG) profiles of palm oil are listed in Table 1 and Table 2, respectively.

TABLE 1

Fatty acid profile of palm oil

| | \ | Fatty acid | | | | | |
|---|---|---|---|---|---|---|---|
| | C12:0 | C14:0 | C16:0 | C18:0 | C18:1 | C18:2 | Others |
| Content (%) | 0.2 | 1.0 | 42.9 | 4.4 | 40.8 | 10.2 | 0.5 |

TABLE 2

TAG profiles of palm oil. (M, myristic acid; O, oleic acid; P, palmitic acid; L, linoleic acid; S, stearic acid)

| Unsaturated TAGs | OLL | PLL | OLO | POL | PLP | OOO | POO | POP | SOO | POS |
|---|---|---|---|---|---|---|---|---|---|---|
| Content (%) | 0.4 | 1.2 | 1.5 | 8.9 | 9.2 | 3.9 | 23.2 | 30.2 | 2.9 | 6.7 |

| Saturated TAGs | PPM | | PPP | | PPS | | Others | | | |
|---|---|---|---|---|---|---|---|---|---|---|
| Content (%) | 0.2 | | 6.7 | | 1.1 | | 3.8 | | | |

Analytical Methods for PMTAG

The PMTAG, as represented by the non-limiting synthesis procedure, was analyzed using different techniques. These techniques can be broken down into: (i) chemistry characterization techniques, including iodine value, acid value, nuclear magnetic resonance (NMR), gas chromatography (GC), and high pressure liquid chromatography (HPLC), including fast and slow methods of the HPLC; and (ii) physical characterization methods, including thermogravimetric analysis (TGA), differential scanning calorimetry (DSC), rheology, solid fat content (SFC), and polarized light microscopy (PLM).

Chemistry Characterization Techniques

Iodine and acid values of the PMTAG was determined according to ASTM D5554-95 and ASTM D4662-03, respectively.

$^1$H-NMR spectra were recorded on a Varian Unity-INOVA at 499.695 MHz. $^1$H chemical shifts are internally referenced to CDCl$_3$ (7.26 ppm) for spectra recorded in CDCl$_3$. All spectra were obtained using an 8.6 µs pulse with 4 transients collected in 16 202 points. Datasets were zero-filled to 64 000 points, and a line broadening of 0.4 Hz was applied prior to Fourier transforming the sets. The spectra were processed using ACD Labs NMR Processor, version 12.01.

HPLC analysis was performed on a Waters Alliance (Milford, Mass.) e2695 HPLC system fitted with a Waters ELSD 2424 evaporative light scattering detector. The HPLC system was equipped with an inline degasser, a pump, and an auto-sampler. The ELSD nitrogen flow was set at 25 psi with nebulization and drifting tube maintained at 12° C. and 55° C., respectively. Gain was set at 500. All solvents were HPLC grade and obtained from VWR International, Mississauga, ON. Waters Empower Version 2 software was used for data collection and data analysis. Purity of eluted samples was determined using the relative peak area. For a fast method of PMTAG analysis, the analysis was performed on a C18 column (150 mm×4.6 mm, 5.0 µm, X-Bridge column, Waters Corporation, MA) maintained at 30° C. by column oven (Waters Alliance). The mobile phase was chloroform:acetonitrile (40:60)v run for 10 min at a flow rate of 1 ml/min. 1 mg/ml (w/v) solution of crude sample in chloroform was filtered through single step filter vial (Thomson Instrument Company, 35540, CA) and 10 µL of sample was passed through the C18 column by reversed-phase in isocratic mode. For a slower method of PMTAG analysis, the analysis was performed using two columns (C18, 150 mm×4.6 mm, 5.0 µm, X-Bridge column, Waters Corporation, MA, and Superspher 100 RP-18, 250 mm×4.0 mm, Thermo Science) set up in series at 30° C. The mobile phase was 2-Propanol:acetonitrile:Heptane (38:57:5)v run for 120 min at a flow rate of 0.5 ml/min. 5 mg/ml (w/v) solution of crude sample in Heptane was filtered through single step filter vial (Thomson Instrument Company, 35540, CA) and 4 µL of sample was passed through the columns by reversed-phase in isocratic mode. This method achieved a better separation than the fast method.

Gas chromatography (GC) was performed on an Agilent 7890 Gas Chromatograph equipped with a split/splitless inlet. The column effluent was split using an Agilent splitter assembly with makeup gas. The splitter was connected the two detectors via deactivated guard columns. The length of the guard column was 0.5 m to the Flame Ionization Detector and 5.0 m to the Agilent 5975C Mass Selective detector. The column used for the analysis was a Restek Rtx-65TG capillary column (Crossbond 65% diphenyl/35% dimethyl polysiloxane; 30 m×0.25 mm×0.1 µm df). One microliter of the sample was injected using a LEAP Technologies Combi-PAL autosampler equipped with a 10 µL syringe.

| Instrument Parameters - Agilent GC/MS - FID | |
|---|---|
| Injection Volume | 1 µL |
| Syringe Size | 10 µL |
| Septum Purge Flow | 3 mL/minute |
| Split Ratio | 20:1 |
| Split Flow | 40 mL/minute |
| Column Flow (Helium) | 2 mL/minute (constant flow) |
| Initial Column Pressure | 16.0 psig |
| Inlet Temperature | 275° C. |
| MSD Transfer Line | 300° C. |
| Oven Parameters | |
| Equilibration Time | 0.5 minutes |
| Initial Temperature | 40° C. |
| Initial Time | 5 minutes |
| Temperature Ramp 1 | 10° C./minute |
| Final Temperature 1 | 200° C. |
| Time 1 | 0 minutes |
| Temperature Ramp 2 | 20° C./minute |
| Final Temperature 2 | 350° C. |
| Time 2 | 11.5 minutes |
| Total Run Time | 40 minutes |
| MSD Parameters | |
| Solvent Delay | 2 minutes |
| EMV Mode | Relative |

| Instrument Parameters - Agilent GC/MS - FID | |
| --- | --- |
| Relative Voltage | 0 |
| Resulting EM Voltage | 1765 |
| Low Mass | 35.0 amu |
| High Mass | 550 amu |
| MS Source Temperature | 230° C. |
| MS Quad Temperature | 150° C. |
| FID Parameters | |
| Detector Temperature | 375° C. |
| Hydrogen Flow | 30 mL/minute |
| Air Flow | 400 mL/minute |
| Makeup Flow (Nitrogen) | 25 mL/minute |

Physical Characterization Techniques

TGA was carried out on a TGA Q500 (TA Instruments, DE, USA) equipped with a TGA heat exchanger (P/N 953160.901). Approximately 8.0-15.0 mg of sample was loaded in the open TGA platinum pan. The sample was heated from 25 to 600° C. under dry nitrogen at a constant rate of 10° C./min.

DSC measurements were run on a Q200 model (TA Instruments, New Castle, Del.) under a nitrogen flow of 50 mL/min. TAG samples between 3.5 and 6.5 (±0.1) mg were run in hermetically sealed aluminum DSC pans. Crystallization and melting behavior of PMTAG was investigated using standard DSC. The samples were equilibrated at 90° C. for 10 min to erase thermal memory, and then cooled at a constant rate of 5.0, 1.0 or 0.1° C./min to −90° C. where they were held isothermally for 5 min, and subsequently reheated at a constant rate of 5.0° C./min to 90° C. The "TA Universal Analysis" software was used to analyze the DSC thermograms and extract the peak characteristics. Characteristics of non-resolved peaks were obtained using the first and second derivatives of the differential heat flow.

SFC measurements were performed on a Bruker Minispec mq 20 pNMR spectrometer (Milton, ON, Canada) equipped with a combined high and low temperature probe supplied with $N_2$. The temperature was controlled with Bruker's BVT3000 temperature controller with an accuracy of ±0.1° C. The temperature was calibrated with commercial canola oil using a type K probe (TRP-K, Omega, Stamford, Conn.) immersed in the oil and an external data logger (Oakton, Eutech Instruments, Singapore). Approximately 0.57±0.05 ml of fully melted sample was quickly pipetted into the bottom portion of the NMR tube. The thermal protocol used in the DSC were also used in the NMR. Bruker's minispec V2.58 Rev. 12 and minispec plus V1.1 Rev. 05 software were used to collect SFC data as a function of time and temperature. The SFC values are reported as the ratio of the intensity of the NMR signal of the solid part to the total detected NMR signal in percent (labelled as SFC %).

A Leica DM2500P polarized light microscope (PLM) fitted with a Leica DFC420C digital camera (Leica Microsystems, Wetzlar, Germany) was used for image capture of the microstructure of the PMTAG. The samples were processed in a temperature-controlled stage (Linkam LTS 350) fitted to the PLM. The formation of the fat crystal network from the early crystallites through their growth and aggregation were observed in-situ under the PLM. The micrographs presented (100× and 500×) were captured at −90° C.

A temperature-controlled Rheometer (AR2000ex, TA Instruments, DE, USA) was used to measure the viscosity and flow property of PMTAG using a 40 mm 2° steel geometry. Temperature control was achieved by a Peltier attachment with an accuracy of 0.1° C. Shear Stress was measured at each temperature by varying the shear rate from 1 to 1200 $s^{-1}$. Measurements were taken at 10° C. intervals from high temperature (100° C.) to 10° C. below the DSC onset of crystallization temperature of each sample. Viscosities of samples were measured from each sample's melting point up to 110° C. at constant temperature rate (1.0 and 3.0° C./min) with constant shear rate (200 $s^{-1}$). Data points were collected at intervals of 1° C. The viscosity obtained in this manner was in very good agreement with the measured viscosity using the shear rate/share stress. The shear rate range was optimized for torque (lowest possible is 10 µNm) and velocity (maximum suggested of 40 rad/s).

The shear rate-shear stress curves were fitted with the Herschel-Bulkley equation (Eq 1), a model commonly used to describe the general behavior of materials characterized by a yield stress.

$$\tau = \tau_0 + K\dot{\gamma}^n \quad \text{Eq. 1}$$

where $\dot{\gamma}$ denotes the shear stress, $\tau_0$ is the yield stress below which there is no flow, K the consistency index and n the power index. n depends on constitutive properties of the material. For Newtonian fluids n=1, shear thickening fluids, n>1 and for shear thinning fluids, n<1.

Palm Oil MTAG Compositional Analysis

The natural oil composition, and in particular, the palm oil composition, was described previously in commonly assigned U.S. Provisional Patent Application Ser. No. 61/971,475, and the TAG profiles of palm oil were also described previously. The TAGs which can potentially compose PMTAG based on palm oil composition and the possible products of cross-metathesis of palm oil are listed in Table 3a. The potential structures of TAGs in PMTAG are listed in Table 3b.

TABLE 3a

Potential TAG composition in PMTAG. D: 9-decenoic acid; Dd: 9-dodecenioc acid; M, myristic acid; O, oleic acid; P, palmitic acid; L, linoleic acid; S, stearic acid. There are both trans- and cis- double bonds in the TAG

| TAGs in Palm oil | Potential TAG composition of PMTAG |
| --- | --- |
| OLL, OLO, OOO | ODD, DDD, DDDd, DDdDd, OLL, OLO, OOO, OLD, OLDd, OOD, ODD, ODDd, ODdDd, LDD, LDDd, LDdDd, DdDdDd, and their isomers |
| PLL | PLL, PDD, PLD, PDDd, PLDd, PDdDd and their isomers |
| POL, POO | POL, POO, PDD, POD, PDDd, PODd, PDdDd and their isomers |
| SOO | SOO, SDD, SOD, SDDd, SODd, SDdDd and their isomers |
| PLP, | PLP, PDP, PDdP |
| POP | POP, PDP, PDdP |
| POS | POS, PDS, PDdS |
| PPM, PPP, PPS | PPM, PPP, PPS |

TABLE 3b
Structures of potential TAGs in PMTAG
| Compounds | Structures |
|---|---|
| OLL | 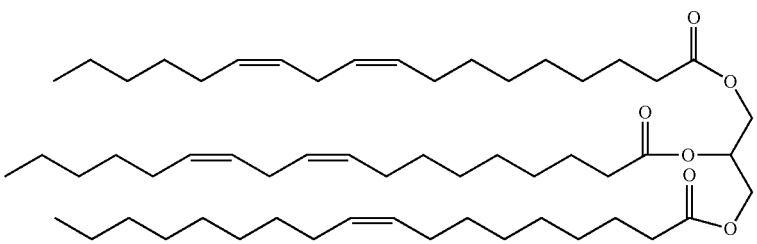 [SMILES: CCCCC/C=C\C/C=C\CCCCCCCC(=O)OCC(COC(=O)CCCCCCC/C=C\CCCCCCCC)OC(=O)CCCCCCC/C=C\C/C=C\CCCCC] |
| OLO | 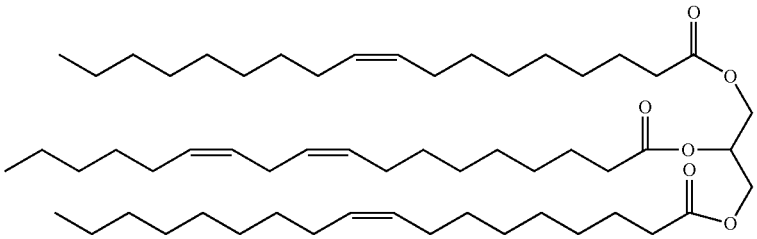 [SMILES: CCCCC/C=C\C/C=C\CCCCCCCC(=O)OC(COC(=O)CCCCCCC/C=C\CCCCCCCC)COC(=O)CCCCCCC/C=C\CCCCCCCC] |
| OOO | 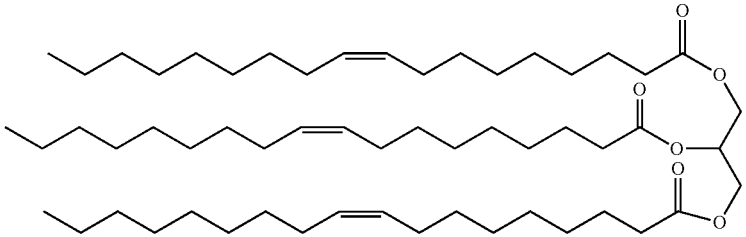 [SMILES: CCCCCCCC/C=C\CCCCCCCC(=O)OCC(COC(=O)CCCCCCC/C=C\CCCCCCCC)OC(=O)CCCCCCC/C=C\CCCCCCCC] |
| ODD | 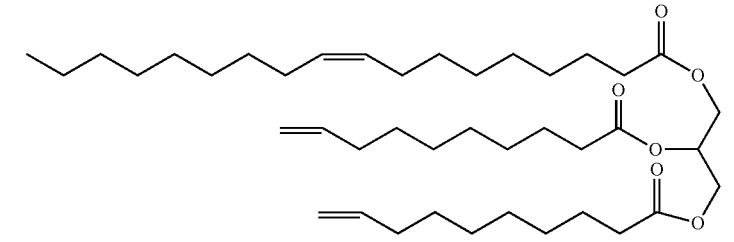 [SMILES: C=CCCCCCCCC(=O)OCC(COC(=O)CCCCCCC/C=C\CCCCCCCC)OC(=O)CCCCCCCC=C] |
| DDD | 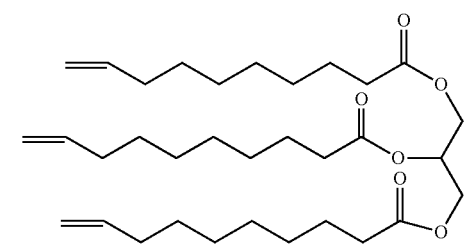 [SMILES: C=CCCCCCCCC(=O)OCC(COC(=O)CCCCCCCC=C)OC(=O)CCCCCCCC=C] |
| DDDd | 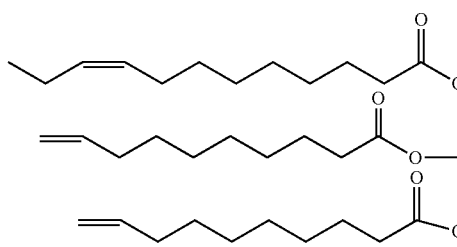 |

TABLE 3b-continued
Structures of potential TAGs in PMTAG
| Compounds | Structures |
|---|---|
| DDdDd | 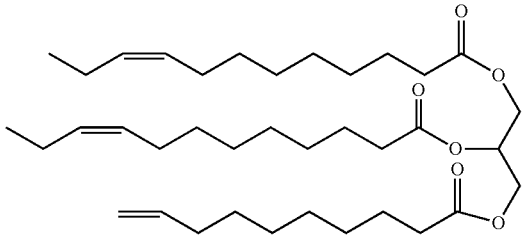 [SMILES: C=CCCCCCCCC(=O)OCC(COC(=O)CCCCCCC/C=C\CC)OC(=O)CCCCCCC/C=C\CC] |
| OLD | 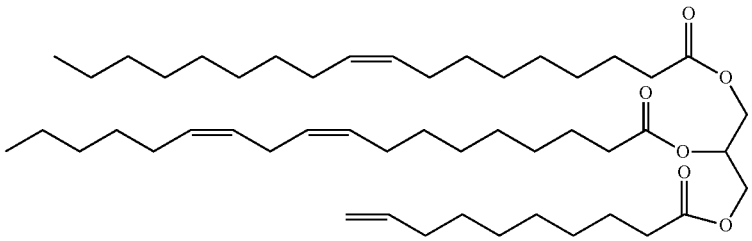 [SMILES: C=CCCCCCCCC(=O)OCC(COC(=O)CCCCCCC/C=C\CCCCCCCC)OC(=O)CCCCCCC/C=C\C/C=C\CCCCC] |
| OLDd | 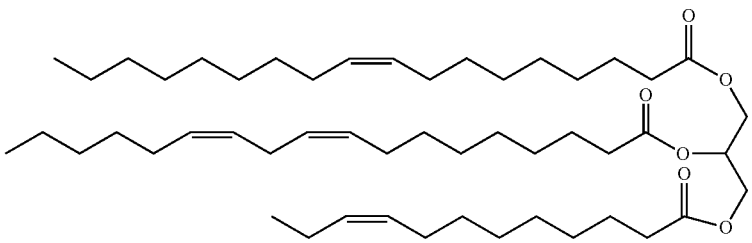 [SMILES: CC/C=C\CCCCCCCC(=O)OCC(COC(=O)CCCCCCC/C=C\CCCCCCCC)OC(=O)CCCCCCC/C=C\C/C=C\CCCCC] |
| OOD | 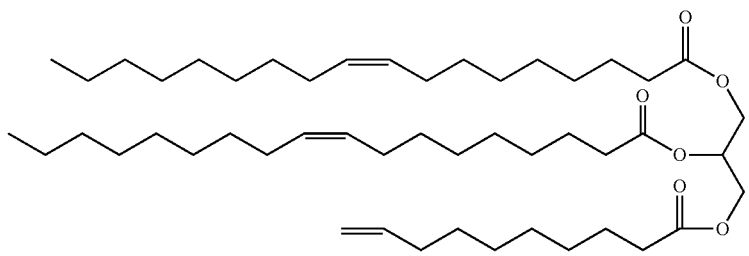 [SMILES: C=CCCCCCCCC(=O)OCC(COC(=O)CCCCCCC/C=C\CCCCCCCC)OC(=O)CCCCCCC/C=C\CCCCCCCC] |
| ODD | 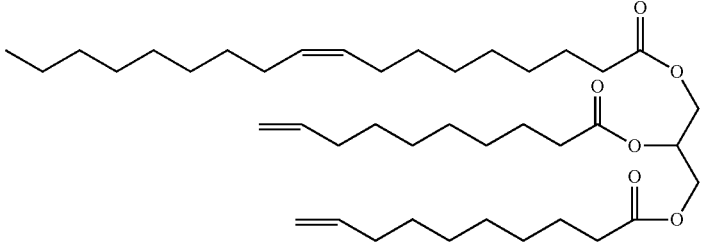 [SMILES: C=CCCCCCCCC(=O)OCC(COC(=O)CCCCCCC/C=C\CCCCCCCC)OC(=O)CCCCCCCC=C] |
| ODDd | 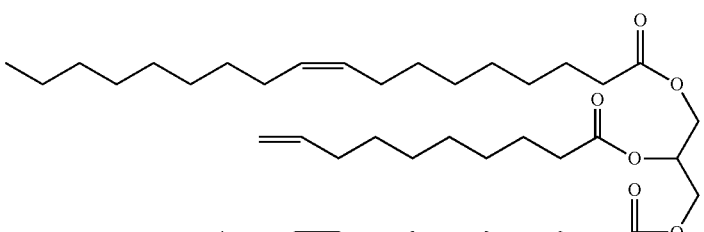 |

TABLE 3b-continued
Structures of potential TAGs in PMTAG
| Compounds | Structures |
|---|---|
| ODdDd | 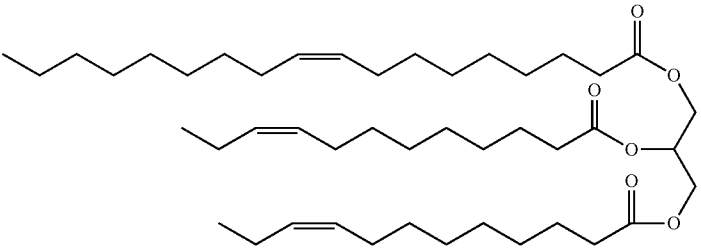 [SMILES: CC/C=C\CCCCCCCC(=O)OCC(COC(=O)CCCCCCC/C=C\CCCCCCCC)OC(=O)CCCCCCC/C=C\CC] |
| LDD | 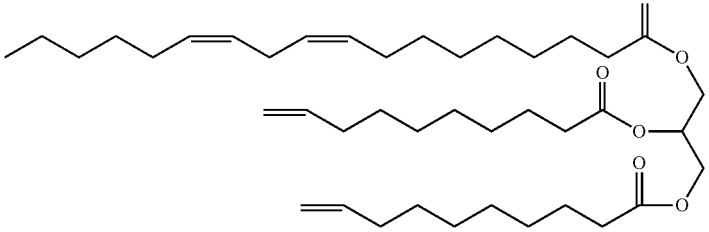 |
| LDDd | 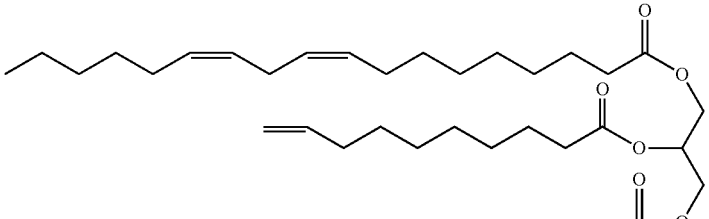 |
| LDdDd | 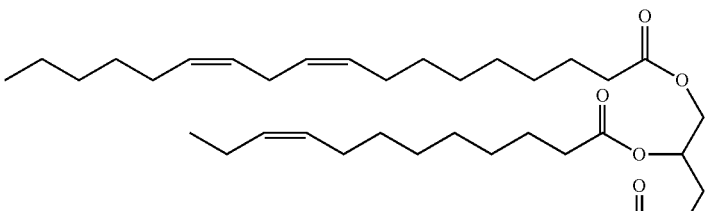 |
| DdDdDd | 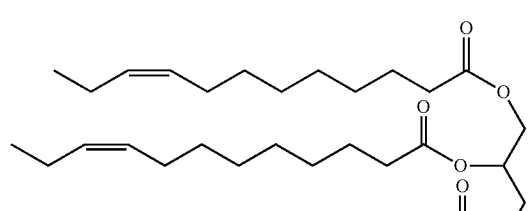 |
| PLL | 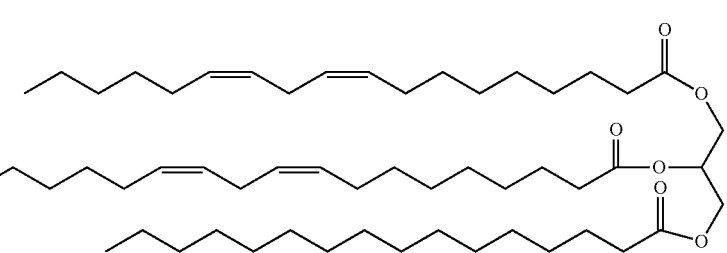 |

TABLE 3b-continued
Structures of potential TAGs in PMTAG
| Compounds | Structures |
|---|---|
| PDD | 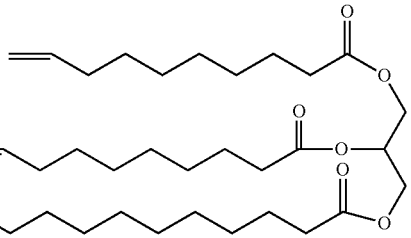 |
| PLD | 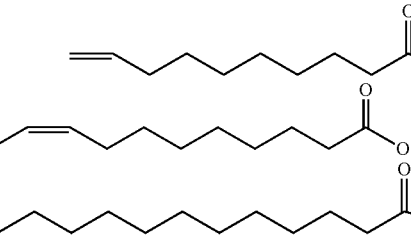 |
| PDDd | 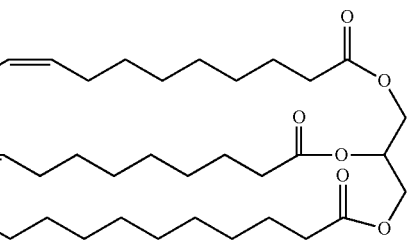 |
| PLDd | 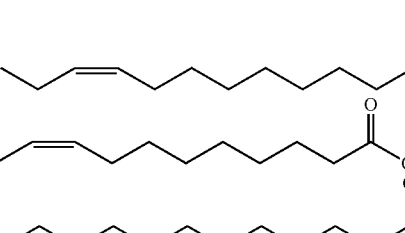 |
| PDdDd | 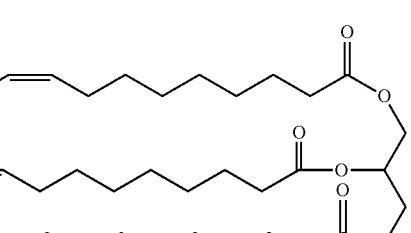 |
| POL | 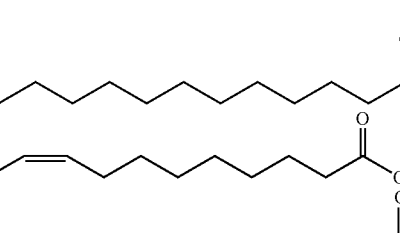 |

TABLE 3b-continued
Structures of potential TAGs in PMTAG
| Compounds | Structures |
|---|---|
| POO | 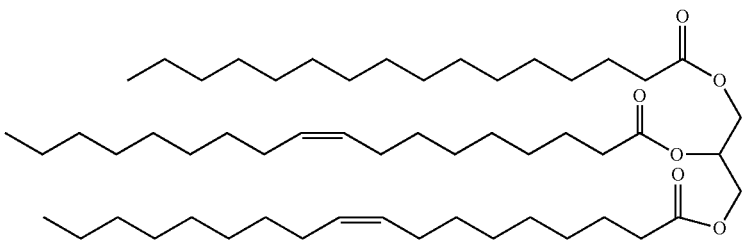 [SMILES: CCCCCCCC/C=C\CCCCCCCC(=O)OCC(COC(=O)CCCCCCCCCCCCCCC)OC(=O)CCCCCCC/C=C\CCCCCCCC] |
| POD | 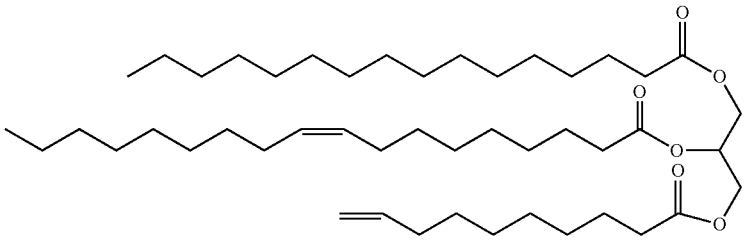 [SMILES: C=CCCCCCCCC(=O)OCC(COC(=O)CCCCCCCCCCCCCCC)OC(=O)CCCCCCC/C=C\CCCCCCCC] |
| PODd | 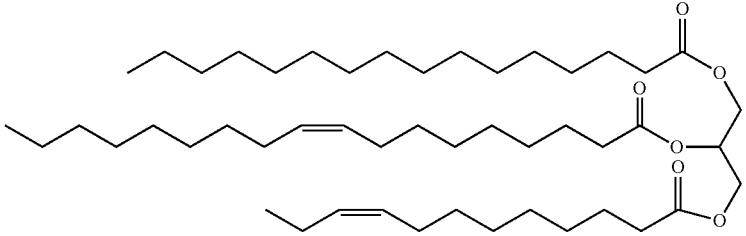 [SMILES: CC/C=C\CCCCCCCC(=O)OCC(COC(=O)CCCCCCCCCCCCCCC)OC(=O)CCCCCCC/C=C\CCCCCCCC] |
| SOO | 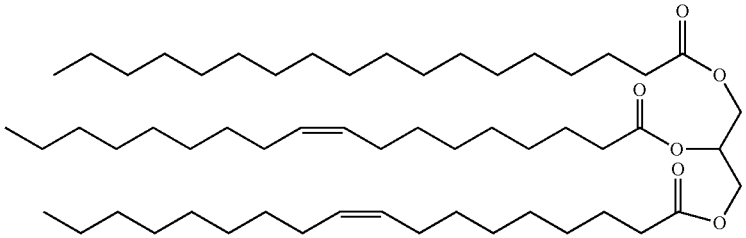 [SMILES: CCCCCCCC/C=C\CCCCCCCC(=O)OCC(COC(=O)CCCCCCCCCCCCCCCCC)OC(=O)CCCCCCC/C=C\CCCCCCCC] |
| SDD | 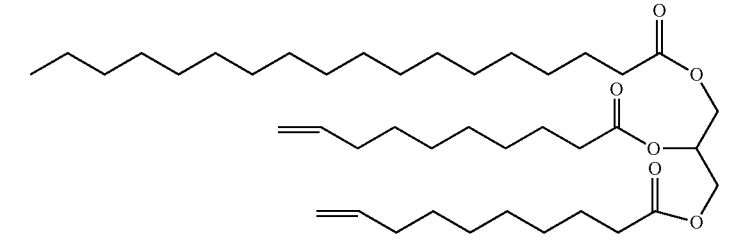 [SMILES: C=CCCCCCCCC(=O)OCC(COC(=O)CCCCCCCCCCCCCCCCC)OC(=O)CCCCCCCC=C] |
| SOD | 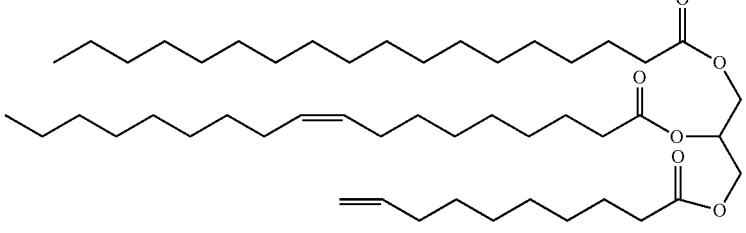 |

TABLE 3b-continued

Structures of potential TAGs in PMTAG

| Compounds | Structures |
|---|---|
| SDDd | 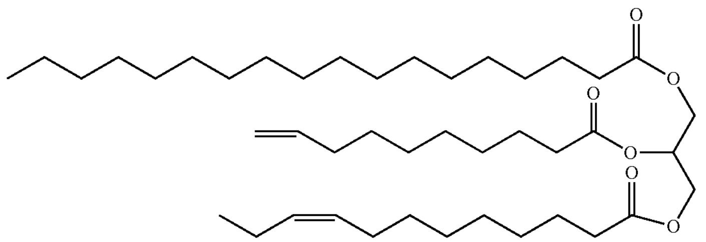 [SMILES: C=CCCCCCCCC(=O)OC(COC(=O)CCCCCCC/C=C\CC)COC(=O)CCCCCCCCCCCCCCCCC] |
| SODd | 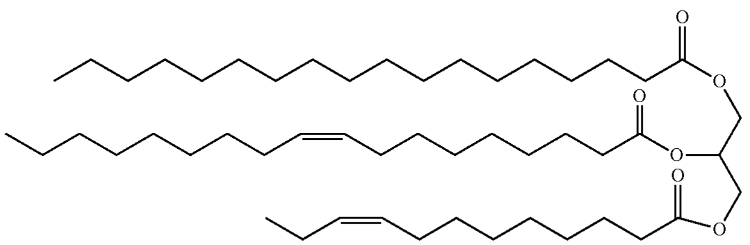 [SMILES: CC/C=C\CCCCCCCC(=O)OCC(COC(=O)CCCCCCCCCCCCCCCCC)OC(=O)CCCCCCC/C=C\CCCCCCCC] |
| SDdDd | 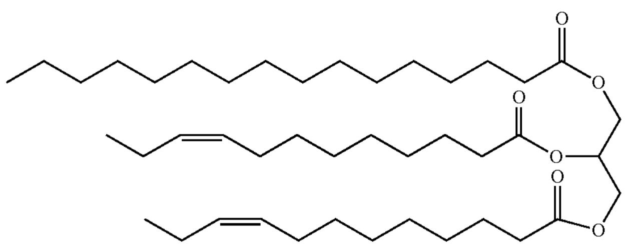 [SMILES: CC/C=C\CCCCCCCC(=O)OCC(COC(=O)CCCCCCCCCCCCCCC)OC(=O)CCCCCCC/C=C\CC] |
| PLP | 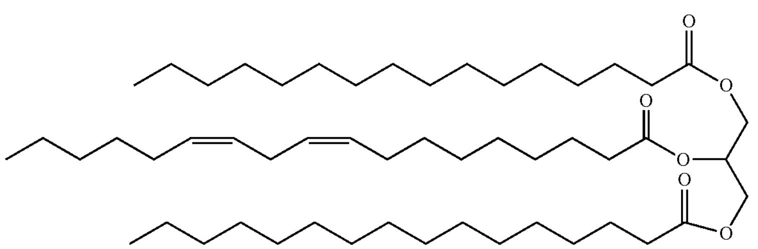 [SMILES: CCCCC/C=C\C/C=C\CCCCCCCC(=O)OC(COC(=O)CCCCCCCCCCCCCCC)COC(=O)CCCCCCCCCCCCCCC] |
| PDP | 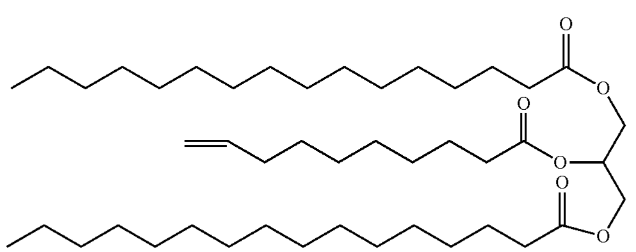 [SMILES: C=CCCCCCCCC(=O)OC(COC(=O)CCCCCCCCCCCCCCC)COC(=O)CCCCCCCCCCCCCCC] |
| PDdP | 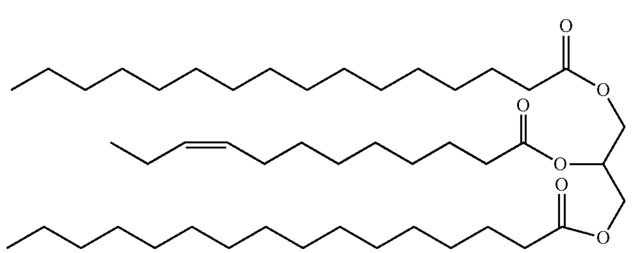 [SMILES: CC/C=C\CCCCCCCC(=O)OC(COC(=O)CCCCCCCCCCCCCCC)COC(=O)CCCCCCCCCCCCCCC] |

TABLE 3b-continued

Structures of potential TAGs in PMTAG

| Compounds | Structures |
|---|---|
| POP | 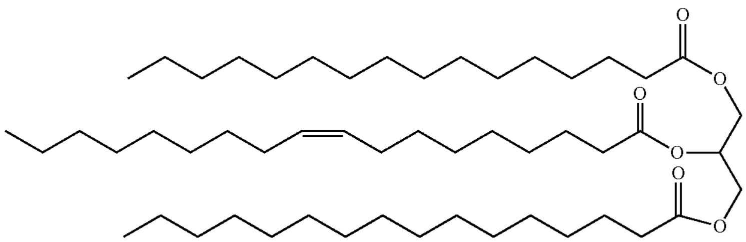 [SMILES: CCCCCCCC/C=C\CCCCCCCC(=O)OC(COC(=O)CCCCCCCCCCCCCCC)COC(=O)CCCCCCCCCCCCCCC] |
| POS | 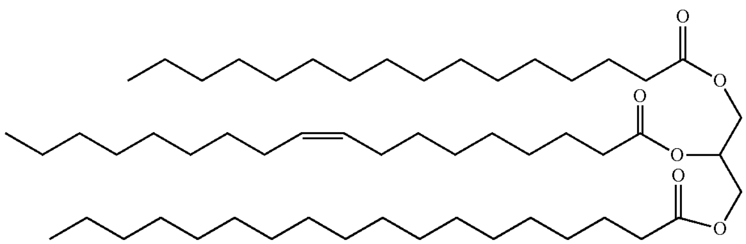 [SMILES: CCCCCCCC/C=C\CCCCCCCC(=O)OC(COC(=O)CCCCCCCCCCCCCCC)COC(=O)CCCCCCCCCCCCCCCCC] |
| PDS | 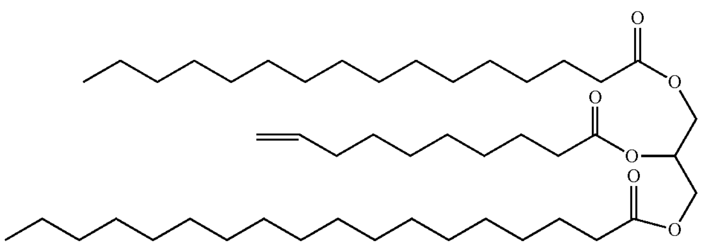 [SMILES: C=CCCCCCCCC(=O)OC(COC(=O)CCCCCCCCCCCCCCC)COC(=O)CCCCCCCCCCCCCCCCC] |
| PDdS | 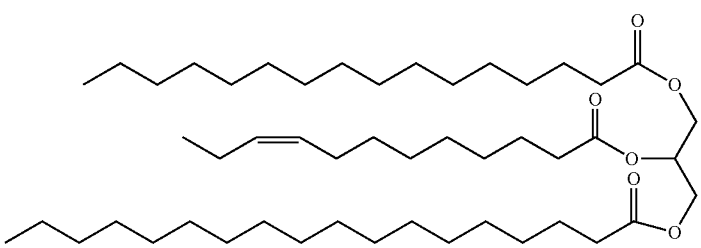 [SMILES: CC/C=C\CCCCCCCC(=O)OC(COC(=O)CCCCCCCCCCCCCCC)COC(=O)CCCCCCCCCCCCCCCCC] |
| PPM | 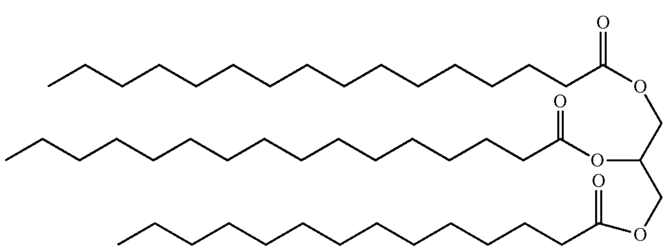 [SMILES: CCCCCCCCCCCCCCCC(=O)OCC(COC(=O)CCCCCCCCCCCCC)OC(=O)CCCCCCCCCCCCCCC] |
| PPP | 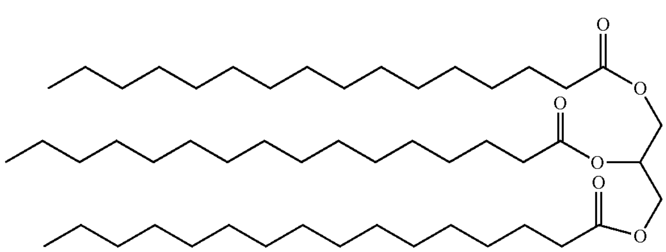 [SMILES: CCCCCCCCCCCCCCCC(=O)OCC(COC(=O)CCCCCCCCCCCCCCC)OC(=O)CCCCCCCCCCCCCCC] |

TABLE 3b-continued

Structures of potential TAGs in PMTAG

| Compounds | Structures |
|---|---|
| PPS | 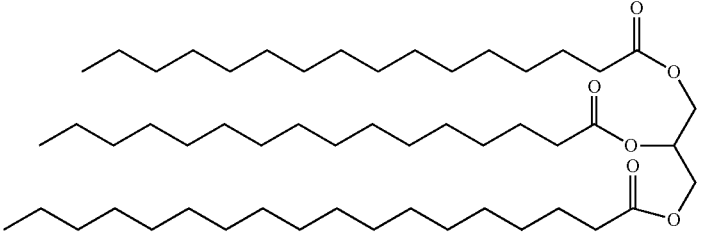 [SMILES: CCCCCCCCCCCCCCCCCC(=O)OCC(COC(=O)CCCCCCCCCCCCCCC)OC(=O)CCCCCCCCCCCCCCC] |

Fatty Acid and TAG Profile of PMTAG

The fatty acid profile of the PMTAG was obtained by GC. Fatty acid profile was also determined using $^1$H-NMR data. TAG profile of PMTAG was investigated using HPLC. Three pure TAGs, namely 3-(stearoyloxy) propane-1,2-diyl bis(dec-9-enoate), or DSS, 3-(dec-9-enoyloxy) propane-1,2-diyl distearate or DDS, and 1, 2, 3-triyl tris (dec-9-enoate) or DDD were synthesized and used as standards to help in the determination of the TAG profile of the PMTAG.

GC of PMTAG Results

TABLE 4

GC results of methylated PMTAG. UFA: unsaturated fatty acids; SFA: saturated fatty acids

| UFA | C10:1 | C12:1 | C12:1 | C12:1 | C13:2 | C15:1 | C15:2 | C15:2 | C18:1 | C18:1 | C18:2 |
|---|---|---|---|---|---|---|---|---|---|---|---|
| Wt. % | 17.52 | 0.28 | 9.13 | 2.04 | 0.91 | 0.58 | 0.22 | 0.29 | 2.97 | 2.80 | 0.17 |
| SFA | C12:0 | C14:0 | C16:0 | C18:0 | C20:0 | C21:0 | Others | | | | |
| Wt. % | 0.31 | 1.24 | 50.35 | 9.28 | 0.35 | 0.12 | 1.28 | | | | |

There are 36.9 wt % unsaturated fatty acids, which includes the double bond of C10:1 in a terminal position (n=0 in Scheme 4). The double bond with n≠0 contains trans- or/and cis-configurations. The GC detected less than 2 wt. % of polyunsaturated fatty acids and more than 60 wt. % saturated fatty acids. Note that the ratio of the trans-/cis-configuration depends on the reaction conditions, such as reaction temperature and catalyst.

HPLC of PMTAG Results

The HPLC curve recorded using the slow method described in the analytical methods section is shown in FIG. 1. As shown, an excellent separation was obtained. The analysis of the HPLC of PMTAG was carried out with the help of pure synthesized TAGs (DDD, DSS and DDS) used as standards. The retention time of these standards were well matched with the related PMTAG fractions. The results of the analysis are reported in Table 5.

TABLE 5

HPLC analysis data of PMTAG

| Peak | Retention time (min) | Content (%) | Structure |
|---|---|---|---|
| 1 | 10.2 | 0.25 | DDD |
| 2 | 11.0 | 0.75 | — |
| 3 | 17.0 | 10.4 | — |
| 4 | 19.9 | 11.3 | DDS |
| 5 | 34.3 | 42.4 | — |
| 6 | 41.9 | 16.4 | — |

TABLE 5-continued

HPLC analysis data of PMTAG

| Peak | Retention time (min) | Content (%) | Structure |
|---|---|---|---|
| 7 | 51.8 | <0.1 | DSS |
| 8 | 79.6 | 5.6% | — |

Figure 2A:
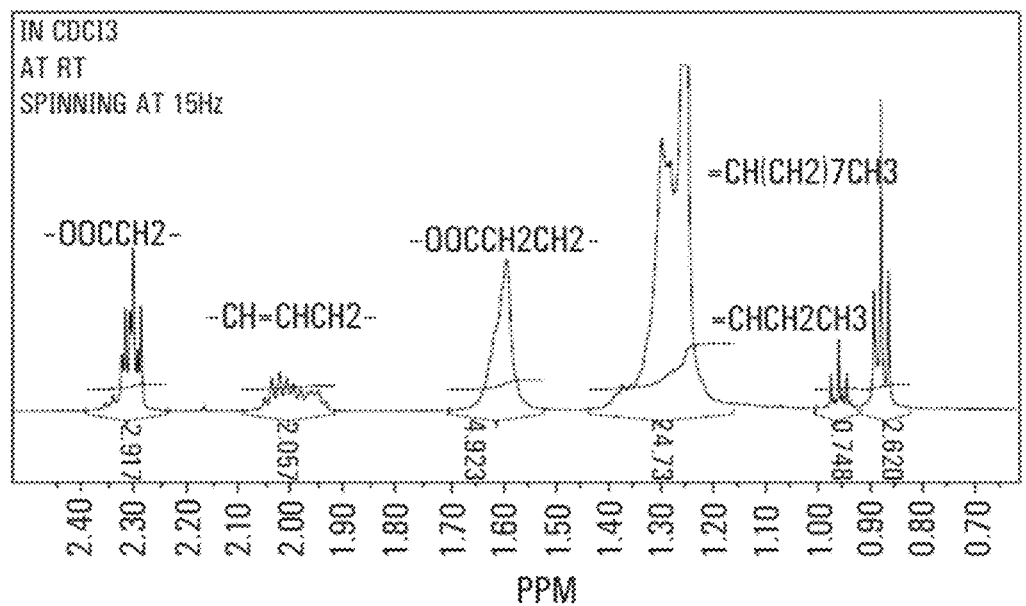
FIG. 2A depicts $^1$H-NMR of PMTAG, with chemical shift range between δ 2.5 and 0.7 ppm.
Figure 2B:
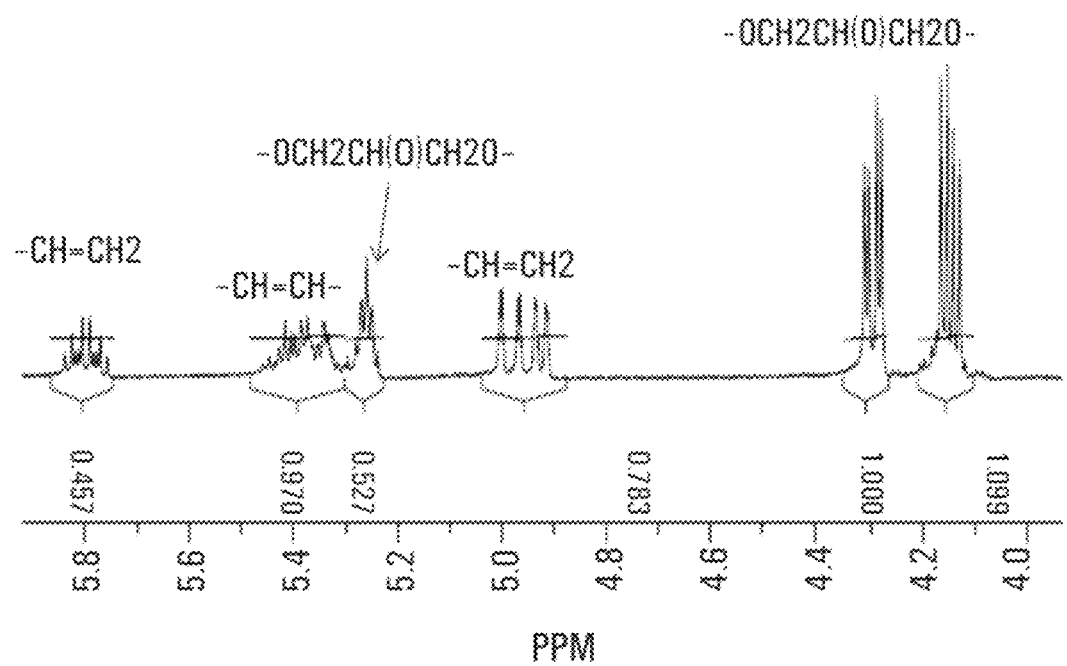
FIG. 2B depicts $^1$H-NMR of PMTAG, with chemical shift range between δ 6.0 and 4.0 ppm.

$^1$H-NMR of PMTAG Results $^1$H-NMR spectra of PMTAG is shown in FIGS. 2A and 2B. The protons of the glycerol skeleton, —CH$_2$CH(O)CH$_2$— and —OCH$_2$CHCH$_2$O— are clearly present at δ 5.3-5.2 ppm and 4.4-4.1 ppm, respectively. Two kinds of double bonds were detected: (1) terminal double bond (n=0), —CH=CH$_2$ and —CH=CH$_2$ present at δ 5.8 ppm and 5.0 to 4.9 ppm, respectively, and the internal double bond (n≠0), —CH=CH— at δ 5.5 ppm to δ 5.3 ppm. The ester group —C(=O)CH$_2$— was present at δ 2.33-2.28 ppm, α-H to —CH=CH— at δ 2.03-1.98 ppm, and —C(=O)CH$_2$CH$_2$— at δ 1.60 ppm. Two kind of —CH$_3$ were detected, one with n=2 at 1.0-0.9 ppm and another with n=8 at 0.9-0.8 ppm. It should be noticed that polyunsaturated fatty acids were not detected by NMR as the chemical shift at 2.6 to 2.8 ppm, the signature $^1$H-NMR of the proton between two double bonds in a polyunsaturated fatty acid was not presented.

Due to the very low content of free fatty acid in the MTAG material as indicated by the acid value (<1), the analysis was performed assuming that only TAG structures were present in the MTAG. The fatty acid profile of PMTAG was calculated based on the relative area under the characteristic chemical shift peaks. The results are listed in Table 6.

TABLE 6

Fatty acid profile of PMTAG calculated based on the relative area under the characteristic NMR chemical shift peaks.

| Fatty Acids with: | Content (mol %) |
|---|---|
| —CH=CH$_2$ | 24.9 |
| —CH=CHCH$_2$CH$_3$ | 15.8 |
| other non-terminal double bonds | 10.6-14.5 |
| Saturated fatty acid | 44.8-48.7 |

The possible structures of the MTAG are presented in Scheme 4. These contain fatty acids with terminal double bonds, internal double bonds with n=2 or 8, as well as saturated fatty acids with m=11 to 20. PMTAG also contains saturated TAGs including PPP, PPM and PPS that exist in the starting natural oil.

cooling cycles became sharper and more defined as cooling rate was decreased. Three exotherms can be observed for the lowest cooling rate. The crystallization peak showing above room temperature (exotherm at ~32° C.) is associated with a high temperature fraction of the MTAG, labelled PMTAG stearin, and the two crystallization peaks appearing below room temperature (exotherm at ~12° C.) and at sub-zero temperatures (exotherm at ~−11° C.) are associated with two lower temperature fractions of the PMTAG, labelled collectively PMTAG olein, similar to their palm oil counterparts. The first two fractions were dominantly present as indicated by their relative enthalpy of crystallization of 28.5 J/g and 60.1 J/g (15% and 32% of the total enthalpy, respectively).

At least six endotherm and two resolved exotherms were observed in the DSC heating thermograms of PMTAG outlining that the material is polymorphic. Although not Scheme 4. Possible structures composing PMTAG.

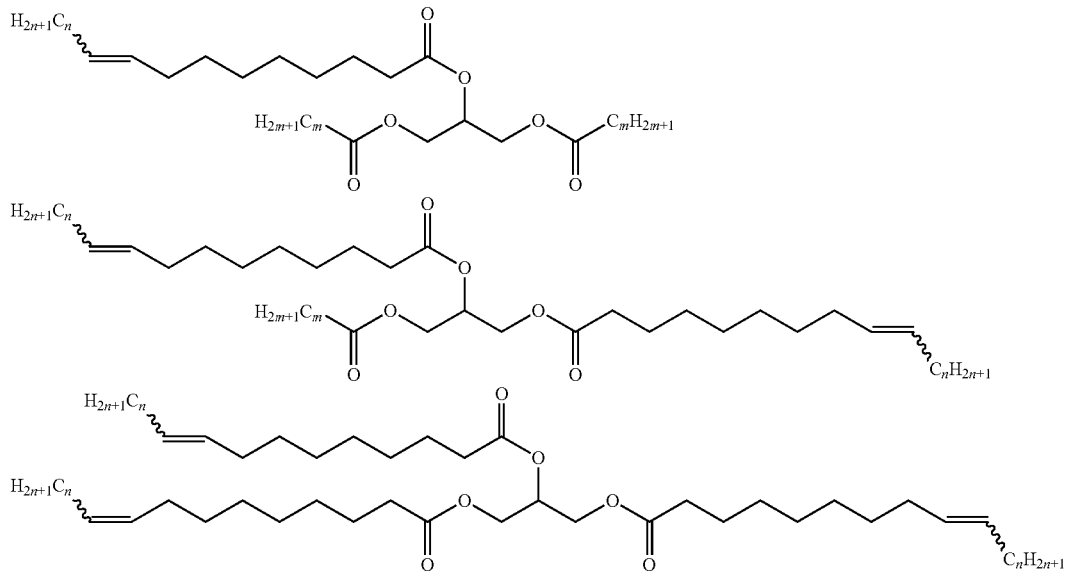

n = 0, 2, 8; m = 11 to 20.

Physical Properties of PMTAG
Thermal Degradation of PMTAG

Figure 3:
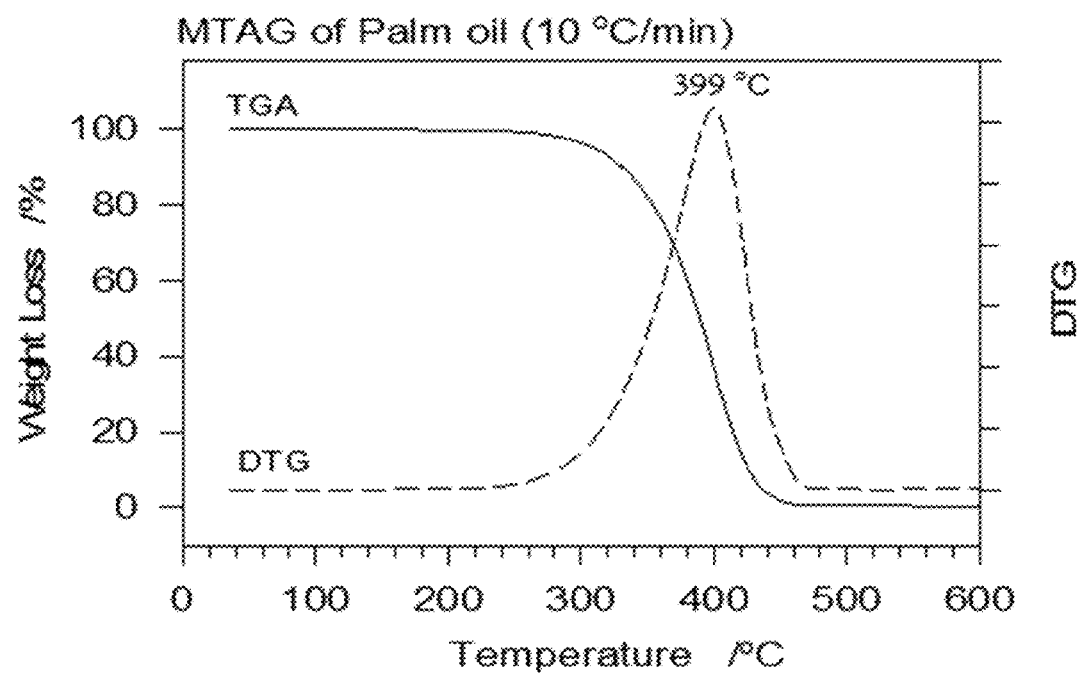
FIG. 3 depicts TGA and DTG of PMTAG.

The TGA and DTG profiles of the PMTAG are shown in the FIG. 3. TGA and DTG reveal one-step decomposition mechanisms for the PMTAG, associated with the breakage of the ester bonds. The onset of degradation of PMTAG as measured by the temperature at 1%, 5% and 10% decomposition was 260.3, 309.0 and 330.5° C., respectively. The extrapolated onset temperature is 333° C. As can be seen from the TGA curve and more precisely from the DTG curve, the decomposition ends at 470° C. The DTG peak occurs at 399.3° C. Nearly 60 wt % of the PMTAG decomposed at this temperature. The data indicates a thermal stability relatively higher than common commercial vegetable oils, such as olive, canola, sunflower and soybean oils, for which first DTG peaks as low as 325° C. have been detected.

Crystallization and Melting Behavior of PMTAG

Figure 4A:
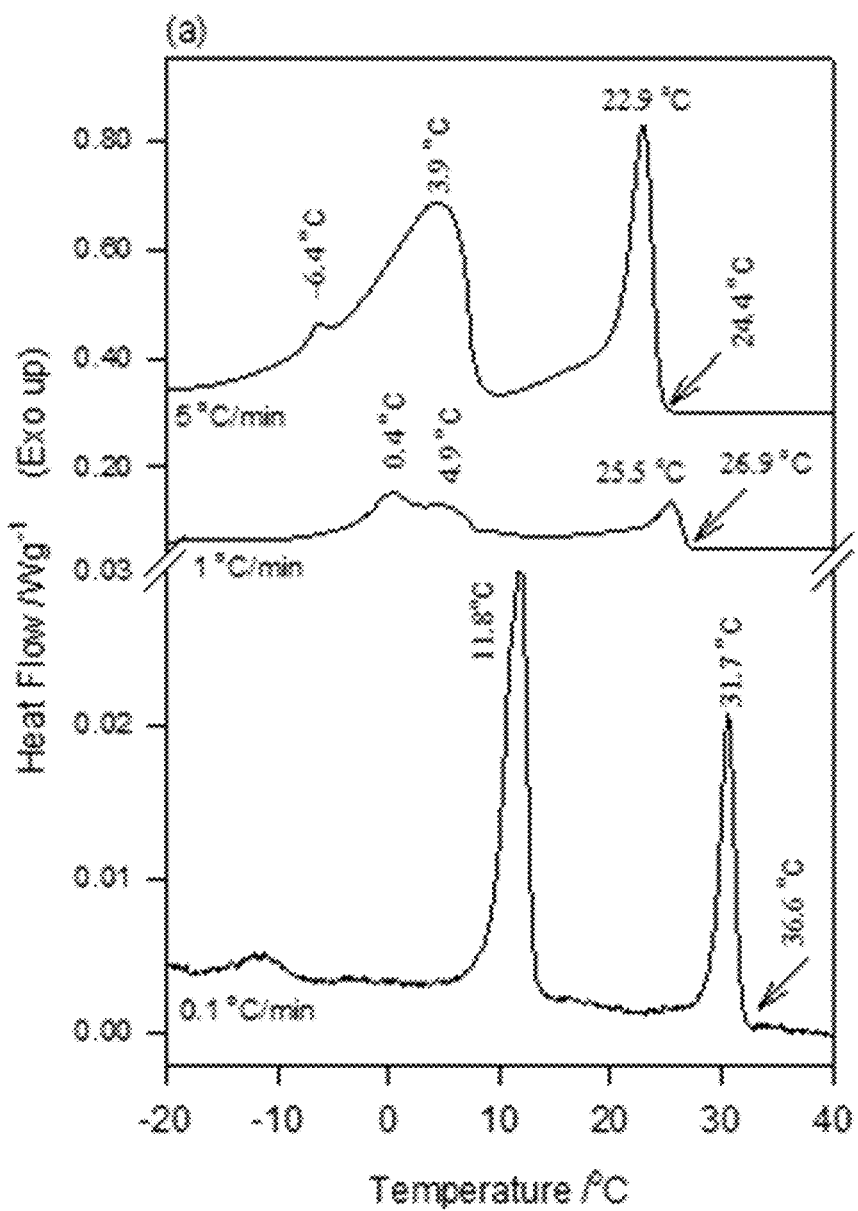
FIG. 4A depicts DSC cooling (5.0, 1.0 and 0.1° C./min)
Figure 4B:
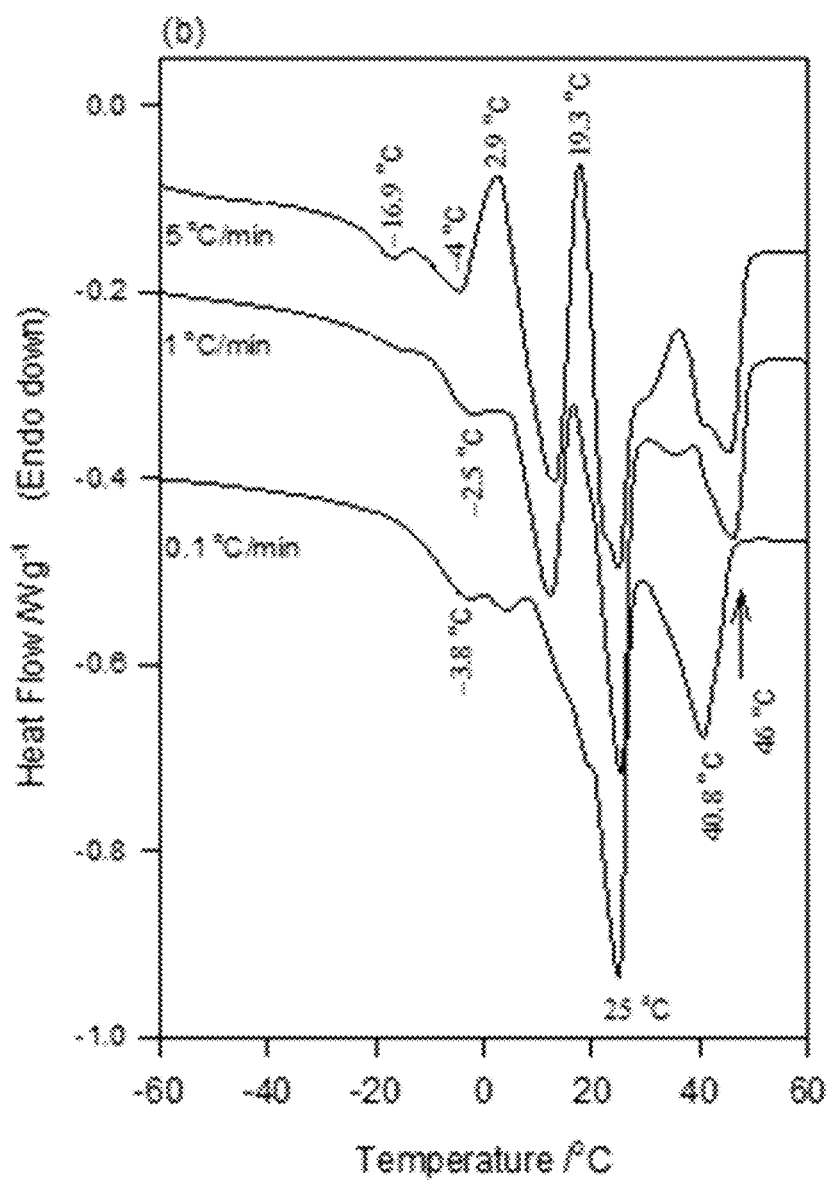
FIG. 4B depicts subsequent DSC heating (5° C./min) thermograms of PMTAG. Cooling rates are reported at the left hand side above each curve and Peak temperatures are reported on the signal maximums.

The DSC thermograms obtained on cooling PMTAG at 5.0, 1.0 and 0.1° C./min and the thermograms obtained by subsequent heating at 5° C./min are presented in FIGS. 4A and 4B, respectively. The exothermic peaks presented in the apparent in the DSC heating thermogram obtained at 0.1° C./min, the last endotherm (at ~41° C., FIG. 4B) is indicative of a phase that was recrystallized during the heating process and subsequently melted. The recorded enthalpy of heating, calculated from the area of the endotherms (109.7 J/g), was much lower than the total enthalpy of crystallization (186.1 J/g), indicating a competition of exothermic and endothermic events during heating which is the result of recrystallization mediated by melt.

The endotherms observed below 30° C. are associated with the melting of PMTAG olein and the endotherms observed above are associated with the melting of PMTAG stearin. As shown in FIG. 4B, the melting of the PMTAG olein and PMTAG stearin were not fully resolved, indicating that a dry fractionation is only possible by using very slow cooling.

Solid Fat Content of PMTAG

Figure 5A:
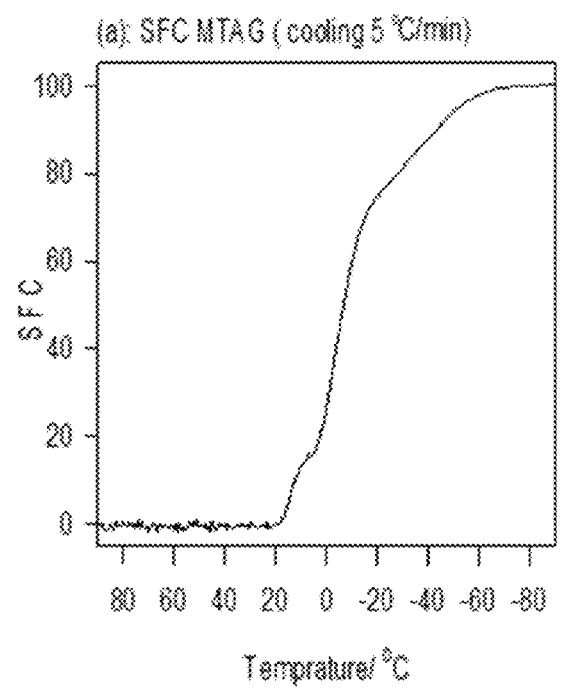
FIG. 5A depicts SFC versus temperature of PMTAG obtained during cooling at 5° C./min.
Figure 5B:
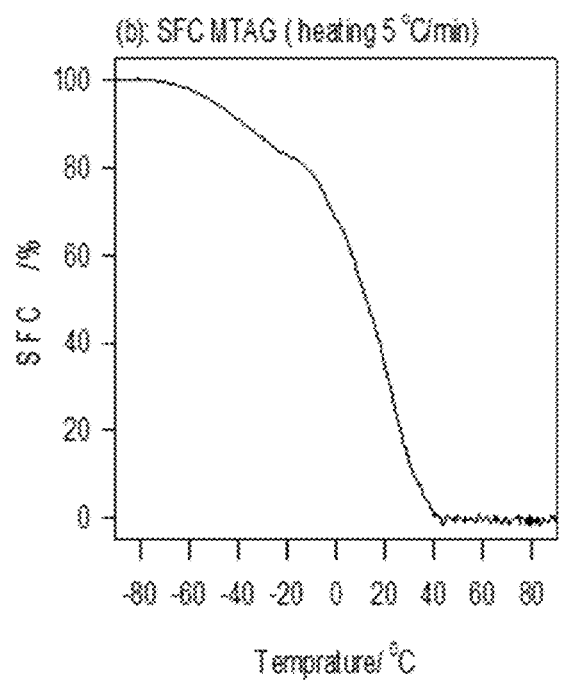
FIG. 5B depicts the subsequent heating at 5° C./min.
Figure 6A:
FIGS. 6A, 6B, 6C, and 6D depict the Microstructure (100×) development of the PMTAG during cooling (5° C.) from the melt.
Figure 6B:
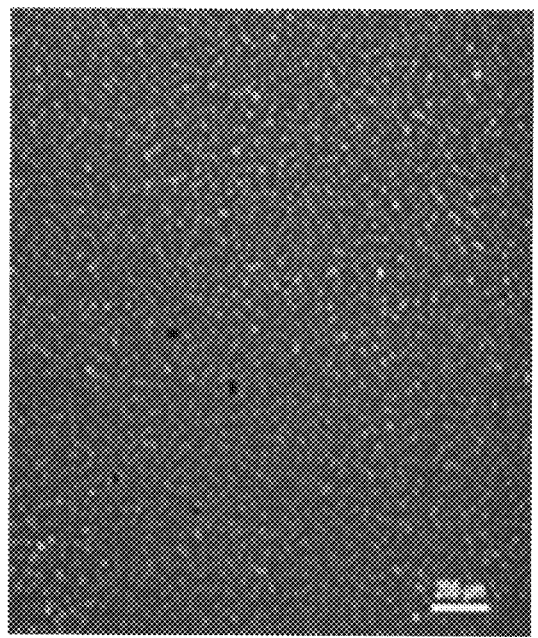
Figure 6C:
Figure 6D:
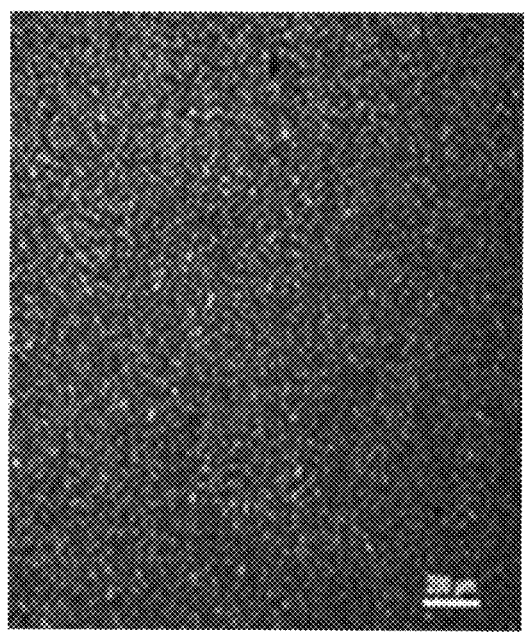
Figure 6E:
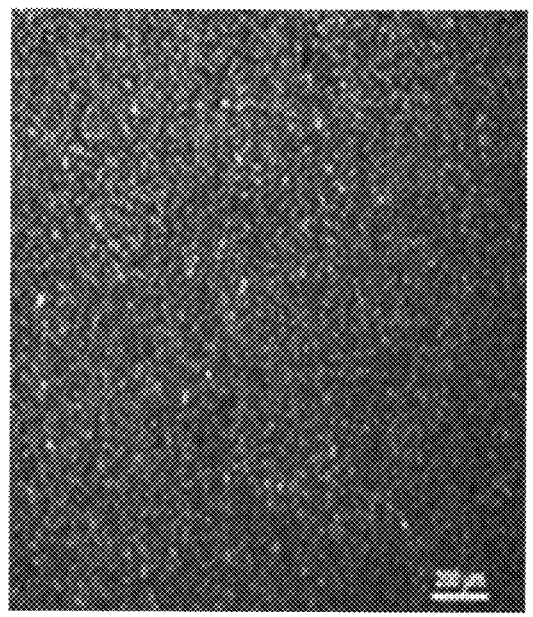
FIGS. 6E and 6F depict the final microstructure of the PMTAG at −90° C. obtained at 100× and 500× magnification, respectively.
Figure 6F:
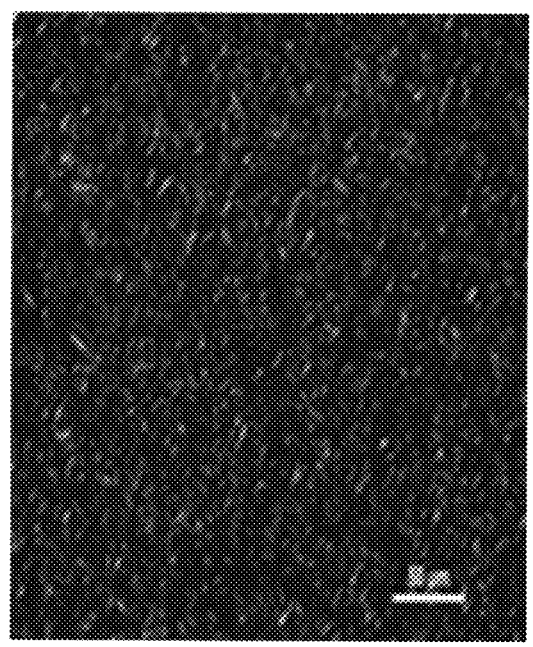

Solid Fat Content (SFC) versus temperature profiles of PMTAG during cooling (5° C./min) and heating (5° C./min) are shown in FIGS. 5A and 5B, respectively. As can be seen in FIG. 5A, the SFC cooling curve presented three segments indicative of a three-step solidification process. The first SFC segment can be associated with PMTAG stearin and the two others to PMTAG olein, similar to the exothermic events observed in the DSC.

Microstructure of PMTAG Evolution

The microstructural analysis was performed in order to determine the microstructure size, shape, development kinetics and final network formation. The development of the microstructure was followed while the sample was cooling at 5° C./min.

FIGS. 6A-6F highlight the development of the microstructure of the PMTAG during cooling at 5° C./min. Crystallization initiated at ~26.1±0.5° C. with very small crystals of average size 20±5 μm. The same type of crystals developed from 26° C. to 14° C. Crystal development was relatively fast. From 14 to 5° C. no development was observed. Secondary nucleation initiated at ~5.0±0.5° C. and several small fibril-like crystals developed at this temperature and continued to develop below 0° C. The different modes of crystallization indicated by both DSC and SFC are reflected in the microstructure development as different types of microstructure evolved following secondary nucleation.

The microstructure analysis also supports that the 5° C./min rate does not allow a microstructure suitable for fractionation to be developed. Higher cooling rates usually lead to the formation of very small microstructures, a situation which is maintained by PMTAG, as evidenced by FIGS. 6E-6F.

Flow Behavior and Viscosity of PMTAG

Figure 7A:
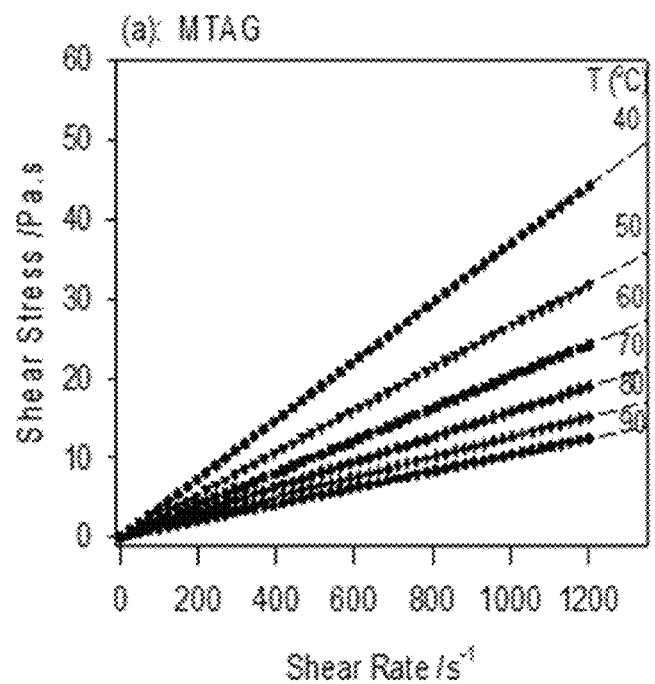
FIG. 7A depicts the heat rate versus shear stress curves of PMTAG showing Newtonian behavior.
Figure 7B:
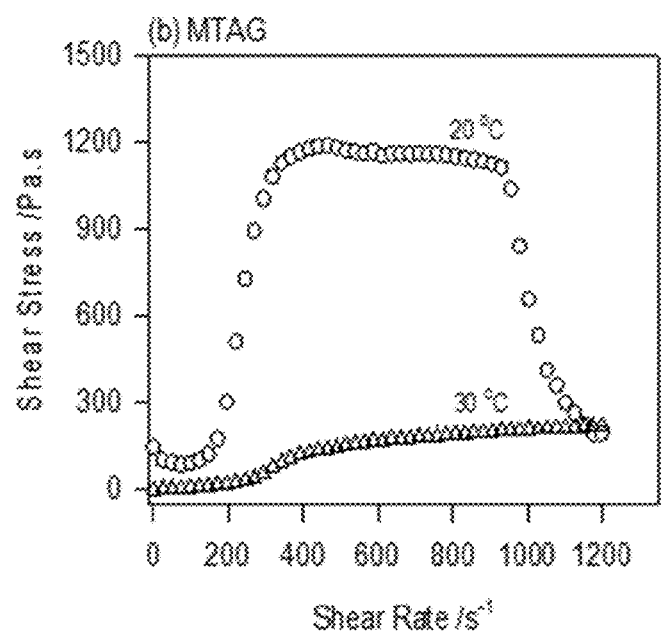
FIG. 7B depicts the heat rate versus shear stress curves of MTAG showing non-Newtonian behavior.
Figure 8:
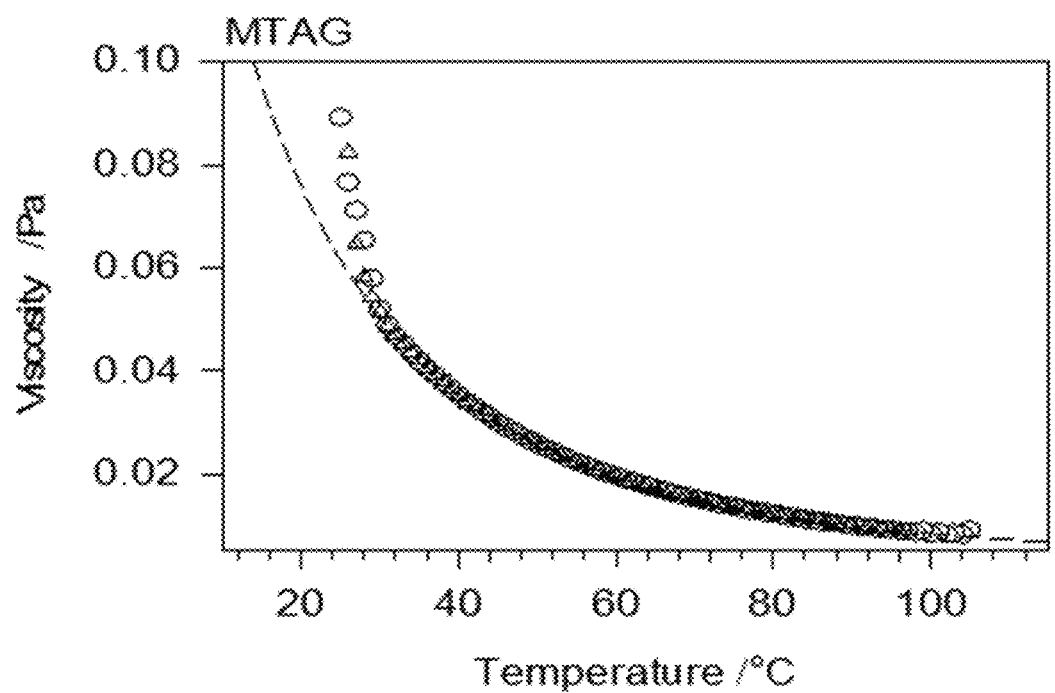
FIG. 8 depicts viscosity versus temperature curves obtained during cooling of PMTAG at (○) 3° C./min and (Δ) 1° C./min. Dashed lines are a guide for the eye.

FIG. 7 shows the flow behavior of MTAG of Palm Oil. Shear rate-shear stress curves of MTAG of Palm Oil obtained at different temperatures are displayed in (FIGS. 7A and 7B). FIG. 8 show the viscosity versus temperature curves obtained during cooling of PMTAG at 3° C./min and 1° C./min. The application of the Herschel-Bulkley equation (Eq. 1) to share rate-shear stress data obtained for the PMTAG at temperatures between 40° C. and 90° C. (R2>0.9999) generated power index values (n) all approximately equal to unity, indicating Newtonian behavior. Fits to the Herschel-Bulkley (eq. 1) model are included in FIG. 7A. The data collected at 30° C. and below (FIG. 7B), indicated that the sample started crystallizing at this temperature, in good correspondence with DSC. The flow behavior observed for PMTAG is very similar to that of vegetable oils.

The viscosity versus temperature of PMTAG obtained using the ramp procedure in the range of temperatures where it was in the liquid state presented the typical exponential behavior of liquid hydrocarbons.

Polyols from MTAG of Palm Oil

Synthesis of Polyols from MTAG of Palm Oil (PMTAG Polyol)

The synthesis of the PMTAG polyol involves epoxidation and subsequent hydroxylation of a MTAG of a natural oil, which is preferably palm oil. Any peroxyacid may be used in the epoxidation reaction, and this reaction will convert a portion of or all of the double bonds present in the PMTAG to epoxide groups. Peroxyacids (peracids) are acyl hydroperoxides and are most commonly produced by the acid-catalyzed esterification of hydrogen peroxide. Any suitable peroxyacid may be used in the epoxidation reaction. Examples of hydroperoxides that may be used include, but are not limited to, hydrogen peroxide, tert-butylhydroperoxide, triphenylsilylhydroperoxide, cumylhydroperoxide, trifluoroperoxyacetic acid, benzyloxyperoxyformic acid, 3,5-dinitroperoxybenzoic acid, m-chloroperoxybenzoic acid and preferably, hydrogen peroxide. The peroxyacids may be formed in-situ by reacting a hydroperoxide with the corresponding acid, such as formic or acetic acid. Other organic peracids may also be used, such as benzoyl peroxide, and potassium persulfate. The epoxidation reaction can be carried out with or without solvent. Commonly used solvents in the epoxidation of the present invention may be chosen from the group including but not limited to aliphatic hydrocarbons (e.g., hexane and cyclohexane), organic esters (i.e. ethyl acetate), aromatic hydrocarbons (e.g., benzene and toluene), ethers (e.g., dioxane, tetrahydrofuran, ethyl ether, tert-butyl methyl ether) and halogenated hydrocarbons (e.g., dichloromethane and chloroform).

Subsequent to the epoxidation reaction, the reaction product may be neutralized. A neutralizing agent may be added to neutralize any remaining acidic components in the reaction product. Suitable neutralizing agents include weak bases, metal bicarbonates, or ion-exchange resins. Non-limiting examples of neutralizing agents that may be used include ammonia, calcium carbonate, sodium bicarbonate, magnesium carbonate, amines, and resin, as well as aqueous solutions of neutralizing agents. Subsequent to the neutralization, commonly used drying agents may be utilized. Such drying agents include inorganic salts (e.g. calcium chloride, calcium sulfate, magnesium sulfate, sodium sulfate, and potassium carbonate).

After the preparation of the epoxidized PMTAG, the next step is to ring-open at least a portion of the epoxide groups via a hydroxylation step. In the present effort, all of the epoxide groups were opened. The hydroxylation step consists of reacting the oxirane ring of the epoxide in an aqueous or organic solvent in the presence of an acid catalyst in order to hydrolyze the oxirane ring to a dihydroxy intermediate. In some aspects, the solvent may be water, aliphatic hydrocarbons (e.g., hexane and cyclohexane), organic esters (i.e. ethyl acetate), aromatic hydrocarbons (e.g., benzene and toluene), ethers (e.g., dioxane, tetrahydrofuran, ethyl ether, tert-butyl methyl ether) and halogenated hydrocarbons (e.g., dichloromethane and chloroform), preferably water and/or tetrahydrofuran. The acid catalyst may be an acid such as sulfuric, pyrosulfuric, perchloric, nitric, halosulfonic acids such as fluorosulfonic, chlorosulfonic or trifluoromethane sulfonic, methane sulfonic acid, ethane sulfonic acid, ethane disulfonic acid, benzene sulfonic acid, or the benzene disulfonic, toluene sulfonic, naphthalene sulfonic or naphthalene disulfonic acids, and preferably perchloric acid. As needed, subsequent washing steps may be utilized, and suitable drying agents (i.e. inorganic salts) may be used.

General Materials for PMTAG Polyol Synthesis

Formic acid (88 wt %) and hydrogen peroxide solution (30 wt %) were purchased from Sigma-Aldrich and perchloride acid (70%) from Fisher Scientific. Hexane, dichloromethane, ethyl acetate and tetrahydrofuran were purchased from ACP chemical Int. (Montreal, Quebec, Canada) and were used without further treatment.

Synthesis of PMTAG Polyol

PMTAG Polyol was prepared in a two-step reaction: epoxidation by formic acid (or acetic acid) and $H_2O_2$, followed by a hydroxylation using $HClO_4$ as a catalyst, as described in Scheme 5. The reaction conditions were optimized for both of the epoxidation and hydroxylation steps with respect to the amount of catalyst, the type of solvent and the reaction temperature. The detailed information is presented in Table 7.

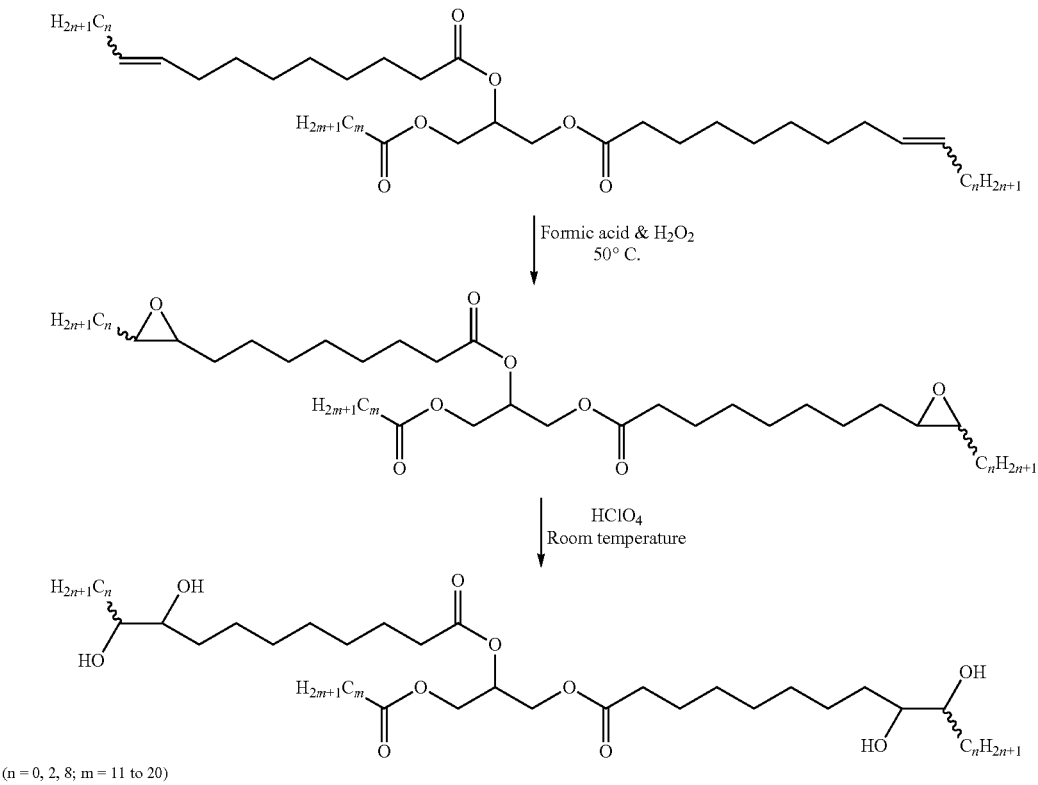

Scheme 5. Synthesis of PMTAG Polyol (n = 0, 2, 8; m = 11 to 20)

Epoxidation Procedure

Formic acid (88%; 200 g) was added to a solution of PMTAG (200 g) in dichloromethane (240 mL). This mixture was cooled to 0° C. Hydrogen peroxide (30%, 280 g) was added dropwise. The resulting mixture was stirred at 50° C., and the progress of the reaction was monitored by a combination of TLC and $^1$H-NMR. The reaction was completed after 48 to 50 hours.

Upon completion, the reaction mixture was diluted with 250 mL dichloromethane, washed with water (200 mL×2), and then with saturated sodium hydrogen carbonate (200 mL×2), and water again (200 mL×2), then dried over anhydrous sodium sulfate. After removing the drying agent by filtration, solvent was removed by roto-evaporation. The crude epoxide was used for the hydroxylation.

$^1$H-NMR Results of Epoxidized PMTAG

Figure 9A:
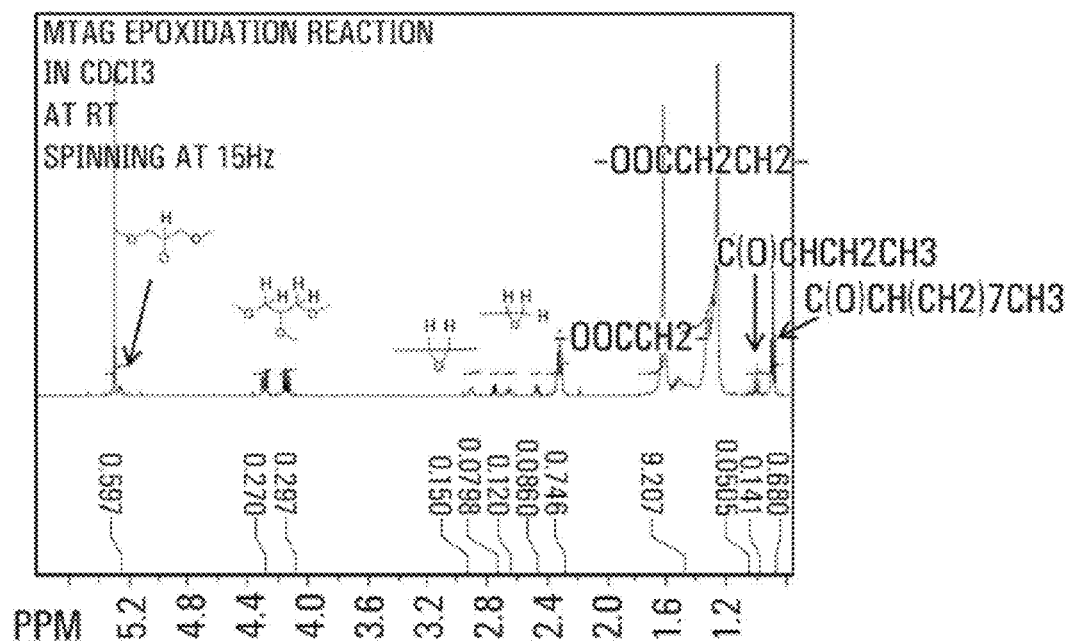
FIG. 9A depicts the $^1$H-NMR spectrum of epoxidized PMTAG.

The $^1$H-NMR of epoxidized PMTAG is shown in FIG. 9A. The protons of the glycerol skeleton, —CH$_2$CH(O) CH$_2$— and —OCH$_2$CHCH$_2$O— are present at δ 5.3-5.2 ppm and 4.4-4.1 ppm, respectively; —C(=O)CH$_2$— at δ 2.33-2.28 ppm; α-H to —CH=CH— at δ 2.03-1.98 ppm; and —C(=O)CH$_2$CH$_2$— at δ 1.60 ppm. There are two types of —CH$_3$, one with n=2 and another with n=8. The first presented a proton at δ=1.0-0.9 ppm, and the second a proton at 0.9-0.8 ppm. The chemical shift at 5.8, 5.4 and 5.0 ppm, characteristic of double bonds, disappeared, whereas, the chemical shift at 2.85 ppm, related to non-terminal epoxy ring, and the chemical shift at 2.7 to 2.4 ppm, related to terminal epoxy ring, appeared, indicating that the epoxidation reaction was successful and complete.

Hydroxylation Procedure

Approximately 200 g crude epoxy PMTAG was dissolved into a 500 mL solvent mixture of THF/H$_2$O (3:2) containing 14.5 g perchloric acid. The reaction mixture was stirred at room temperature and the progress of the reaction was monitored by a combination of TLC and $^1$H-NMR. The reaction was completed after 36 h. The reaction mixture was poured into 240 mL water and extracted with CH$_2$Cl$_2$ (2×240 mL). The organic phase was washed by water (2×240 mL), followed by 5% aqueous NaHCO$_3$ (2×200 mL) and then water (2×240 mL) again. The organic phase was then dried over Na$_2$SO$_4$. After removing the drying agent by filtration, the solvent was removed with a rotary evaporator and further dried by vacuum overnight, giving a light yellow grease-like solid.

Optional Hydroxylation Procedure 50 g epoxidized PMTAG was suspended in 250 mL water. 6 g HClO$_4$ (70%) was added into reaction mixture. The reaction mixture was heated to reflux for 6 h. The mixture was then poured into 1 L water. The mixture was kept at room temperature overnight to solidify the product. The solid polyol was collected by filtration and then dried under vacuum at 60° C.

Optimization of Synthesis of PMTAG Polyol

To reduce the cost and to achieve an alternate chemical route the synthesis of PMTAG Polyol was optimized. The optimization was mainly focused on reducing the amount of formic acid, hydrogen peroxide, perchloric acid and using milder solvents in both epoxidation and hydroxylation reaction. The reaction progress was monitored by TLC and $^1$H-NMR. The achieved products were analyzed using HPLC and $^1$H-NMR. The detailed information is listed in Table 7. As seen in Table 7, the epoxidation of PMTAG was effective and complete when DCM (dichloromethane) was used as solvent, but not when THF, Ethyl Acetate and $H_2O$ were used as solvent, especially for terminal double bonds. Furthermore, a by-product having a formic acid unit attached on the fatty acid backbone was detected when ethyl acetate and water were used as solvent. It should be noted, however, that any of these other methods may be used satisfactorily in an industrial process to produce PMTAG Polyol, depending on the requirements of the end polyurethane product.

Figure 9B:
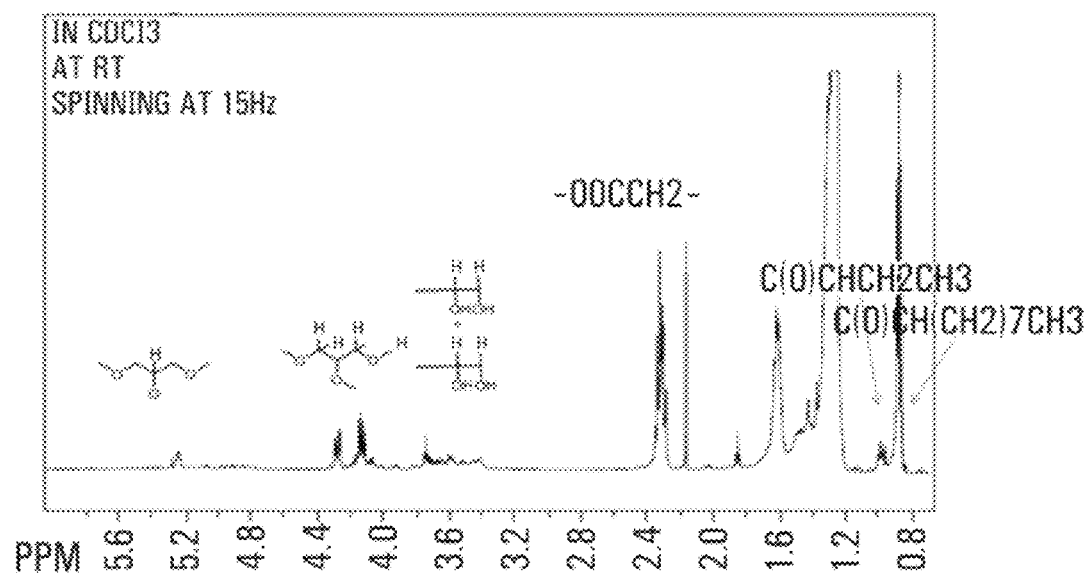
FIG. 9B depicts the $^1$H-NMR spectrum of ring-opened epoxidized (hydroxylated) PMTAG.

The hydroxylation of the epoxidized PMTAG was carried out either in a mixture of THF and water or water only. When a mixture of THF and water was used as solvent, the hydroxylation was carried out at room temperature and 50° C. The reaction performed at 50° C. produced polyols with higher acid values. The weight ratio of perchloric acid/PMTAG was optimized in the hydroxylation reaction performed with THF and water as solvent (see Table 7). For a ratio of 1:1, the polyol (so-called polyol 100%) displayed a higher acid value and lower OH number (Table 7). Its NMR spectrum (FIG. 9B) indicated that the typical TAG-like glycerol backbone was lost, a sign that the hydrolysis of the ester link in TAG occurred.

Figure 9C:
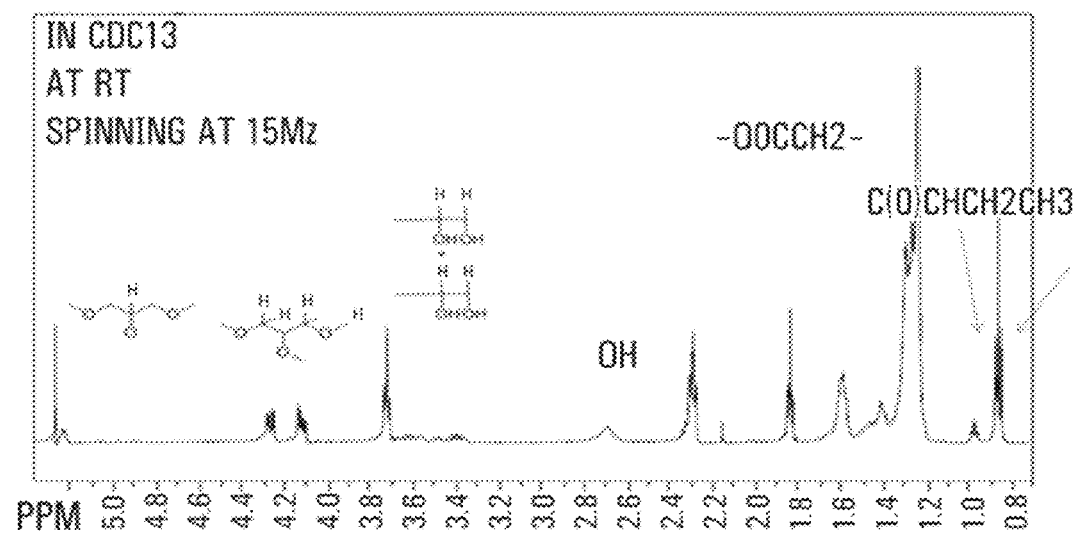
FIG. 9C depicts the $^1$H-NMR spectrum of ring-opened epoxidized (hydroxylated) PMTAG.

When the ratio was reduced to 0.1:1 and 0.05:1, the polyols (so called polyol 10% or polyol 5%, respectively,) displayed much lower acid value and higher OH number (Table 7). A typical TAG-like glycerol backbone was clearly shown in the NMR spectra of PMTAG Polyol 10% and 5% (FIG. 9C), indicating that the hydrolysis of the ester link in TAG was avoided.

The hydroxylation of epoxidized PMTAG in $H_2O$ was also carried out. The reaction time was found to be highly dependent on the acid/PMTAG ratio. When the acid/PMTAG ratio increased from 0.012 to 0.18, the reaction time decreased from 32 hours to 2 hours. When compared with the PMTAG Polyol prepared using THF and $H_2O$ as solvent, the polyol prepared using $H_2O$ as solvent presented a lower OH number but the same acid value, indicating that polyol oligomers were formed during the hydroxylation reaction.

TABLE 7

Optimization parameters of synthesis of PMTAG Polyol and results achieved. Concentration of $H_2O_2$ was 30%; concentration of formic acid was 88%; the ratio listed for the starting materials is based on the 30% $H_2O_2$ solution and 88% formic acid solution.

| Step | Ratio of starting materials (w/w) | Solvent | T (° C.) | Time (hrs) | Note |
|---|---|---|---|---|---|
| Epoxidation | PMTAG/Formic acid/$H_2O_2$ = 1/1/1.4 | DCM | 50 | 48 | Good and completed |
|  |  | THF | 50 | 72 | Not completed, more than 60% terminal double bonds remained |
|  |  | Ethyl acetate | 50 | 72 | Not completed and there were by-products |
|  |  | No solvent | 50, 70, 100 | 72 | Not completed, more than 50% terminal double bonds remained; there were by products at 100° C. |
|  |  | No solvent | 60; exothermic; self-heated to 100° C. | 24 | No double bond detected; Formic ester polyol was formed |
|  | PMTAG/Formic acid/$H_2O_2$ = 1/0.3/1 | DCM | 50 | 72 | Not completed for both terminal and internal double bonds |
|  | PMTAG/Formic acid/$H_2O_2$ = 1/0.2/1 | DCM | 50 | Over 1 week | Not completed for both terminal and internal double bonds |
| Hydroxylation | PMTAG/$HClO_4$ = 1/1 (Polyol 100%) | THF + $H_2O$ | RT | 20 | High acid value(>50) OH value ~120 |
|  | PMTAG/$HClO_4$ = 1/0.1 (Polyol 10%) | THF + $H_2O$ | RT | 48 | Low acid value (~6) OH value ~150 |
|  | PMTAG/$HClO_4$ = 1/0.05 (Polyol 5%) | THF + $H_2O$ | RT | 48 | Low acid value (~6) OH value ~150 NMR is same as polyol10% |
|  | PMTAG/$HClO_4$ = 1/0.08 | $H_2O$ | Reflux | 5 to 6 | Low acid value (~7) OH value ~130 NMR and HPLC is same as polyol 5% |
|  | PMTAG/$HClO_4$ = 1/0.18 | $H_2O$ | Reflux | 2 | NMR and HPLC are similar to polyol 5% |
|  | PMTAG/$HClO_4$ = 1/0.012 | $H_2O$ | Reflux | 32 | NMR and HPLC similar to 5% polyol |

A standardized PMTAG Polyol was therefore synthesized using the procedure outlined for MTAG Polyol 5%. It will be heretofore referred to simply as PMTAG Polyol; however, the various other examples of process and solvent summarized in Table 7 used to produce various classes of PMTAG-derived polyol are by inclusion valued as capable of producing various other useful classes of polyols. As shown in FIG. 11, for the standardized PMTAG Polyol, the chemical shifts at 2.8-2.4 ppm related to the epoxy ring disappeared from the $^1$H-NMR of the PMTAG Polyol, and the chemical shifts at 3.8-3.4 ppm related to proton neighbored by —OH appeared, indicating that the hydroxylation of epoxy ring was complete.

Synthesis of Green Polyols from PMTAG

The synthesis of the Green (solvent free) Polyol from the MTAG of palm oil involves epoxidation and subsequent hydroxylation of a MTAG of palm oil. Four different batches of Green Polyol were prepared (B1 to B4-Polyol) by adjusting reaction parameters during epoxidation.

Any peroxyacid may be used in the epoxidation reaction, and this reaction will convert a portion of or all of the double bonds present in the PMTAG to epoxide groups. Peroxyacids (peracids) are acyl hydroperoxides and are most commonly produced by the acid-catalyzed esterification of hydrogen peroxide. Any suitable peroxyacid may be used in the epoxidation reaction. Examples of hydroperoxides that may be used include, but are not limited to, hydrogen peroxide, tert-butylhydroperoxide, triphenylsilylhydroperoxide, cumylhydroperoxide, trifluoroperoxyacetic acid, benzyloxyperoxyformic acid, 3,5-dinitroperoxybenzoic acid, m-chloroperoxybenzoic acid and preferably, hydrogen peroxide. The peroxyacids may be formed in-situ by reacting a hydroperoxide with the corresponding acid, such as formic or acetic acid. Other organic peracids may also be used, such as benzoyl peroxide, and potassium persulfate.

Subsequent to the epoxidation reaction, the reaction product may be neutralized. A neutralizing agent may be added to neutralize any remaining acidic components in the reaction product. Suitable neutralizing agents include weak bases, metal bicarbonates, or ion-exchange resins. Non-limiting examples of neutralizing agents that may be used include ammonia, calcium carbonate, sodium bicarbonate, magnesium carbonate, amines, and resin, as well as aqueous solutions of neutralizing agents. Subsequent to the neutralization, commonly used drying agents may be utilized. Such drying agents include inorganic salts (e.g. calcium chloride, calcium sulfate, magnesium sulfate, sodium sulfate, and potassium carbonate).

After the preparation of the epoxidized PMTAG, the next step is to ring-open at least a portion of the epoxide groups via a hydroxylation step. In the present effort, all of the epoxide groups were opened. The hydroxylation step consists of reacting the oxirane ring of the epoxide in the presence of an acid catalyst in order to hydrolyze the oxirane ring to a dihydroxy intermediate. The acid catalyst may be an acid such as sulfuric, pyrosulfuric, perchloric, nitric, halosulfonic acids such as fluorosulfonic, chlorosulfonic or trifluoromethane sulfonic, methane sulfonic acid, ethane sulfonic acid, ethane disulfonic acid, benzene sulfonic acid, or the benzene disulfonic, toluene sulfonic, naphthalene sulfonic or naphthalene disulfonic acids, and preferably perchloric acid. As needed, subsequent washing steps may be utilized, and suitable drying agents (i.e. inorganic salts) may be used.

General Materials for Green Polyol Synthesis from PMTAG

Formic acid (88 wt %) and hydrogen peroxide solution (30 wt %) were purchased from Sigma-Aldrich, and perchloride acid (70%) from Fisher Scientific.

Solvent Free Procedure of Synthesis of Green Polyol from PMTAG

PMTAG Green Polyol was prepared from PMTAG in a two-step reaction: epoxidation by formic acid (or acetic acid) and $H_2O_2$, followed by a hydroxylation using $HClO_4$ as a catalyst, as described in Scheme 5. Four batches of PMTAG Green Polyol were prepared using different reaction conditions. The epoxidation conditions were adjusted in order to optimize the reaction and manage the amount of formic acid that can be attached to the polyol. The reaction conditions and data for making the different batches of green polyols are listed in Table 7.

Scheme 5. Synthesis of PMTAG Green Polyol (without solvent).

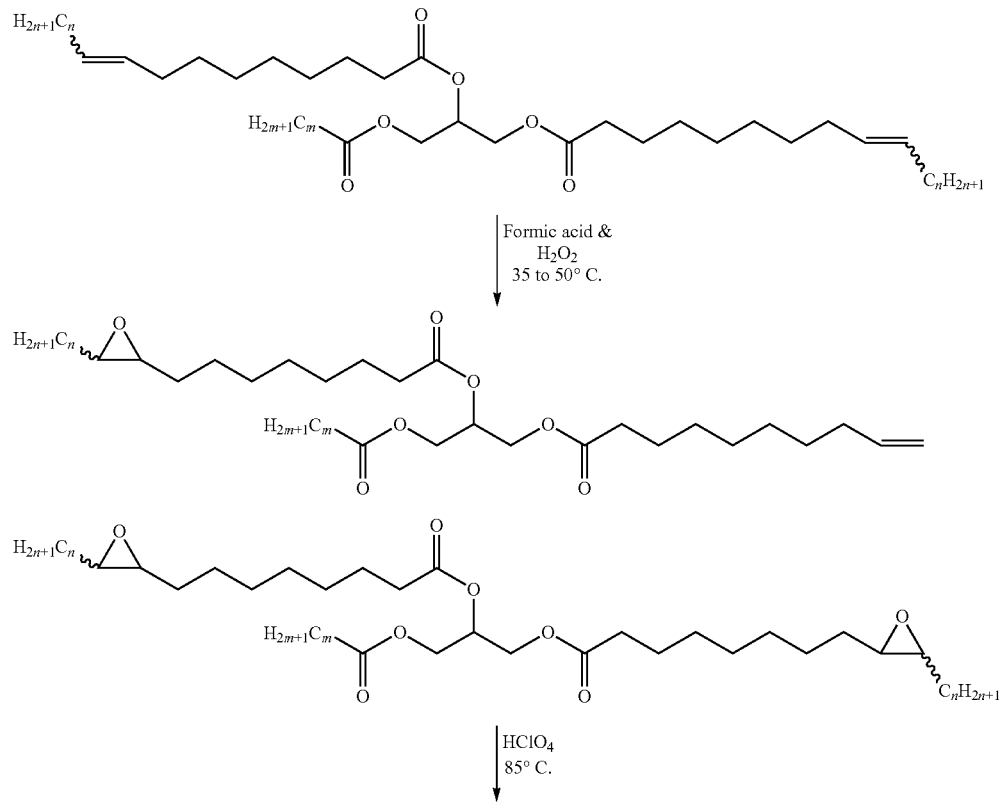

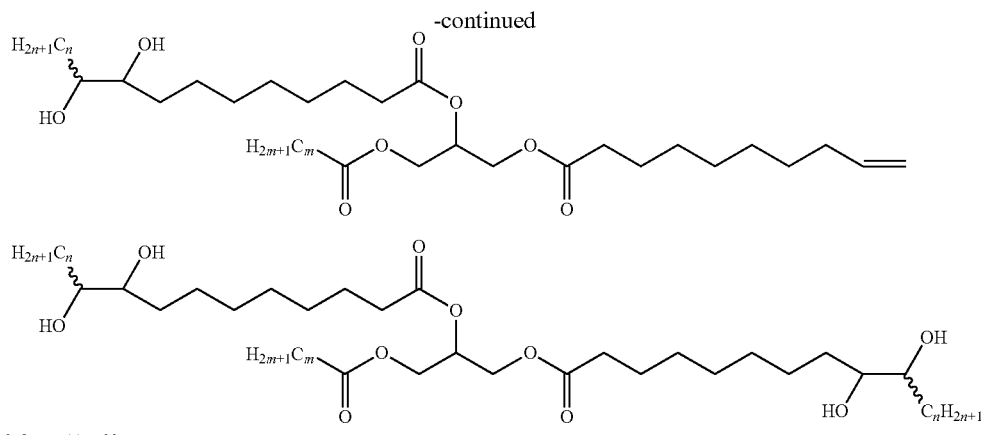

n = 0, 2, 8; m = 11 to 20

TABLE 8

Reaction conditions and data for the synthesis of PMTAG Green polyols. $T_i^{epox}$: Initial temperature of the epoxidation reaction; $T_{max}^{epox}$: highest temperature reached during the epoxidation reaction; $T_R^e$: reaction temperature for epoxidation; $t_{add}$: H$_2$O$_2$ addition time was ~3 h; $T_R^h$: reaction temperature for hydroxylation; $t_R$: reaction time

| Batch | Epoxidation[a] | | | | Hydroxylation[b] | |
|---|---|---|---|---|---|---|
| | $T_i^{epox}$ | $T_{max}^{epox}$ | $T_R^e$ | $t_R$ | $T_R^h$ | $t_R$ |
| 1 | 50 | 65 | 48 | 16 h at 45° C. then 12 h at 48° C. | 85 | 16 h |
| 2 | 40 | 49 | 48 | 16 h at 48° C. | 85 | 16 h |
| 3 | 25 | 95 | 45 | 16 h at 45° C. | 85 | 16 h |
| 4 | 25 | 48 | 25 | 16 h at 25-48° C. | 85 | 16 h |

[a] Formic acid/H$_2$O$_2$/PMTAG = 1/1.4/1. (Formic acid: 88%; H$_2$O$_2$: 30%)
[b] PMTAG/H$_2$O/perchloric acid = 1/5/0.05

Epoxidation Procedure 2 kg PMTAG was added into 2 kg formic acid (88%) in a reactor. The initial temperature of the epoxidation reaction ($T_i^{epox}$) was controlled using a circulator (Thermoscientific, Phoenix II, Newlington, USA). 2.8 L of hydrogen peroxide (30%) was added to the reactor slowly (~1 L/h) with good stirring to ensure that the temperature does not exceed 50° C. Due to the exothermic nature of the epoxidation reaction, the temperature increased to a maximum ($T_{max}^{epox}$) of 48 to 65° C., depending on the batch. The temperature was then reduced to the actual epoxidation temperature ($T^{epox}$) at which the reaction was continued overnight. The reaction mixture was finally washed with 1×2 L water, 1×1 L 5% NaHCO$_3$ and 2×2 L water sequentially. The mixture was used for the next step directly.

Note that the temperature control feature of the circulator was used to cool and heat the reactor for batch 1 and batch 2 but not for batch 3 and 4. Tap water was used to cool the batch 4 epoxidation reaction. For batch 3, where neither the circulator controlling system nor tap water were used, the reaction temperature reached its maximum ($T_{max}^{epox}$=95° C.). However, due to the circulator still operating at the initial setup, the reaction temperature remained less than 10 min at 95° C.

Note that when the temperature was below 70° C., the degree of epoxidation in the melt was limited (~80 to 90% conversion of total double bonds). Also, at temperatures higher than 50° C., the epoxide was opened by formic acid and a formic acid unit attached to the polyol backbone. Therefore, in order to control the amount of formic acid unit attached to the polyol backbone, the epoxidation temperature should be kept below 50° C.

Hydroxylation Procedure

The same hydroxylation parameters were used to make the PMTAG Green polyols (see Table 7). The epoxide of PMTAG (2 kg) was added into 10 L water, and then 140 g HClO$_4$ (70%) was added to the reactor. The reaction mixture was heated to ~85° C. and continued at that temperature for 16 h. The reaction was kept still until ready for phase separation. The organic layer was separated from the water layer. The organic layer was washed with 1×2 L water, 1×1 L 5% NaHCO$_3$ and 2×2 L water sequentially, and then dried on a rotary evaporator.

The analytical methods (chemistry and physical characterization), compositional analysis, HPLC data, chemical structures, and physical properties of PMTAG polyol and PMTAG Green polyol were described in commonly assigned U.S. Provisional Patent Application Nos. 61/971,475 and 62/109,441.

Fractionation of Polyols FROM MTAG of Palm Oil

The fractionation of PMTAG Polyol was achieved based on its crystallization and melting behaviors. Dry and solvent aided crystallization procedures were tried in order to separate the polyol into a high and low melting temperature fractions, referred to as the solid and liquid fractions, SF-Polyol and LF-Polyol, respectively.

Crystallization and Melting Behavior of PMTAG Polyols

Figure 10A:
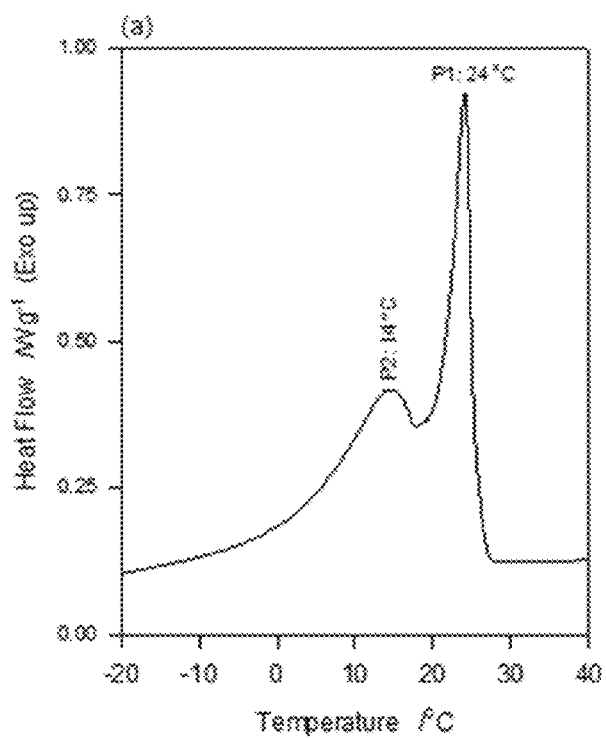
FIG. 10A depicts DSC thermograms of PMTAG Polyol during cooling at 5° C./min.

The fractionation by crystallization of PMTAG Polyol can be understood in light of its thermal transition behavior. The DSC thermogram obtained on cooling PMTAG Polyol and the thermogram obtained by subsequent heating, both at 5° C./min, are presented in FIGS. 10A and 10B, respectively.

Figure 10B:
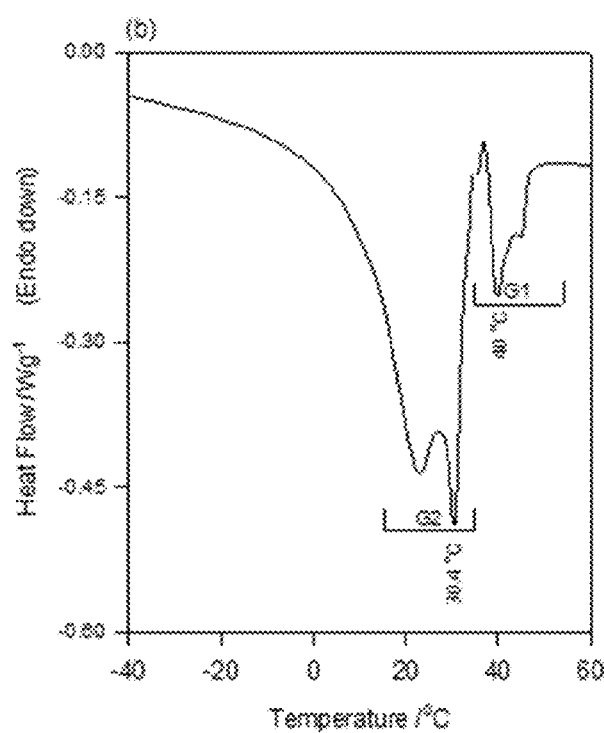
FIG. 10B depicts DSC thermograms of PMTAG Polyol during heating at 5° C./min.

As can be seen, the cooling thermogram of PMTAG Polyol presented two exotherms (P1 at 24° C. and P2 at 14° C. in FIG. 10A), and its heating thermogram presented two relatively well-separated groups of endotherms (G2 below 30° C. and G1 above 30° C. in FIG. 10B). The two exotherms of the cooling thermogram can be related to a high (centered at ~24° C. in FIG. 10A) and low (centered at ~14° C. in FIG. 10A) melting portions in the polyol. The heating thermograms of the polyol did not display exotherms, indicating that polymorphic transformations mediated by melt do not occur with the polyol. Furthermore, the polyol presented an enthalpy of melting of 96.2 J/g that was very similar to its enthalpy of crystallization (94.1 J/g). The high and low temperature melting groups of endotherms G1 and G2 are therefore the recording of the melting of the "high" and "low" melting portions of the polyol, respectively.

The DSC data indicate that with careful processing, it is possible to separate PMTAG Polyol into two fractions: a fraction that would be mainly constituted of the components of the low melting portion (so-called liquid fraction, LF-Polyol), and another that would be mainly constituted of the components of the high melting portion (so-called solid fraction, SF-Polyol). It is expected that at ambient temperature SF-Polyol would be solid and LF-Polyol would remain liquid for some time.

Two methods have been tried to separate PMTAG Polyol into a solid and liquid fractions: 1. Dry fractionation by quiescent cooling followed by isothermal crystallization, and 2. Solvent aided crystallization.

In the following, the liquid and solid fractions of PMTAG Polyol are labeled LF-Polyol and SF-Polyol, respectively. The detailed nomenclature used in the document is presented in Table 8.

Fractionation of PMTAG Polyol by Dry Crystallization—Quiescent Method

In the dry fractionation procedure, the sample was brought from the melt (60° C.) immediately to a temperature ($T_C$) at which it was left to crystallize isothermally for a period of time ($t_C$). The details of the different experiments and the results of the attempted dry fractionations are listed in Table 9.

Practically, ~100 g of melted polyol in 100-ml beaker was placed in a temperature controlled water bath (Julabo FP50-ME, Julabo USA Inc., Vista, Calif.) already set at 60° C. where it was melt and equilibrated for at least 10 min. The sample was then immediately transferred into an incubator already set at the crystallization temperature ($T_C$) and crystallized isothermally during a period of time ($t_C$). Three sets of experiments were conducted. The crystallization temperature ($T_C$=35, 38 and 40° C. in Table 9) were chosen within the span of the first exothermic event shown by the DSC of the polyol in order to promote the crystallization of the high melting components only. $t_C$ was varied in order to promote the crystallization of the solid components of the polyol only, and achieve an optimal separation.

In all these experiments, the polyol crystallized into a white milky and viscous liquid with very small crystals. Attempt to filter the solid part with filter paper (Fisherbrand™, P5) under vacuum (300 torr) failed. The viscosity of the crystallized sample, even after a short crystallization time ($t_C$=4 h in E3, Table 9), was apparently high enough to prevent any filtration. The dry fractionation method did not work for the polyol as it did for PMTAG, and was therefore abandoned.

TABLE 9

Polyol fractionation data (dry method). $T_C$: isothermal crystallization temperature (° C.), and $t_C$: crystallization time (h). Yield of liquid fraction (%)

| Experiment | Mass (g) | $T_C$ (° C.) | $t_C$ (h) | Yield (%) |
|---|---|---|---|---|
| E1 | 100 | 35.0 | 18 | 65.3 |
| E2 | 100 | 38.0 | 8 | 62.9 |
| E3 | 100 | 40.0 | 4 | 72.5 |

Fractionation of PMTAG Polyol by Solvent-Aided Crystallization

Three solvent systems (ethyl acetate (EA), hexane (HX) and tetrahydrofuran (THF)) were tried. In each experiment, 75 g of polyol was mixed at 50° C. under gentle stirring with the solvent (1:1 by weight) in 250 ml Erlenmeyer flask, and then left at room temperature (RT) for 24 hours. After this period of time, the sample with HX crystallized fully, and therefore could not be fractionated. After 24 hours at RT, the sample with THF remained liquid without any visible crystals. Furthermore, placed in a fridge at 2° C. for 60 hours, the sample presented only few visible crystals, which when filtered yielded 5.4 g of solid fraction only.

Sample with EA separated well in two phases after the isothermal crystallization at RT. The solid fraction was filtered from the liquid fraction by filter paper (P8, Fisher Brand) under 300 torr vacuum and yielded 25 g of solid fraction (33.3% solid). The data of this experiment are summarized in Table 10.

TABLE 10

PMTAG Polyol solvent fractionation data. Polyol mass = solvent Mass = 75.0 g; dissolution temperature $T_{disol}$ = 60° C.; V: volume of solvent; $T_C$(° C.): crystallization temperature; $t_C$ (h): crystallization time. Solvent Ethyl acetate (EA); LF-Polyol and SF-Polyol: Liquid and solid fractions of PMTAG Polyol, respectively.

| Polyol | $T_C$ (° C.) | $t_C$ (h) | SF (g) | Yield (%) |
|---|---|---|---|---|
| PMTAG Polyol | 25 | 24 | 25.0 | 33.3 |
| PMTAG Green Polyol | 25 | 24 | 11.4 | 22.1 |

Standard Solvent Fractionation Procedure of PMTAG Polyol

The HX method was not pursued further. The THF method was also abandoned given that even when using stringent fractionation conditions, its yield was very insufficient. Ethyl acetate was chosen as the solvent system for the standard solvent fractionation method of polyols.

Fractionation of Green Polyol by Solvent Aided Crystallization

The PMTAG Polyol synthesized using green method of Batch 4 (PMTAG Green Polyol) was fractionated with the solvent fractionation method. 51.5 gram of PMTAG Green Polyol was mixed at 60° C. under gentle stirring with ethyl acetate (1:1 by weight) in a 250 ml Erlenmeyer flask. The sample was left to crystallize isothermally at room temperature for 24 h.

Two separate phases were obtained. The solid phase was filtered from the liquid by filter paper (P8, Fisher Brand) under 300 torr vacuum. 11.4 g of solid fraction and 40.1 g of liquid fraction were collected (yield of solid=22.1%).

The solid fraction was analyzed by DSC, rheology, SFC, texture analysis and PLM and compared with bees wax.

Analytical Methods for Polyol from the Fractions of PMTAG

The fractions of PMTAG Polyol were analyzed using different techniques. These techniques can be broken down into: (i) chemistry characterization techniques, including iodine value, OH value, acid value, and nuclear magnetic resonance (NMR); and (ii) physical characterization methods, including thermogravimetric analysis (TGA), differential scanning calorimetry (DSC), solid fat content (SFC), polarized light microscopy (PLM) and rheology.

Chemistry Characterization Techniques for SF- and LF-Polyols

Iodine, OH and acid values of SF- and LF-Polyols were determined according to ASTM D5768-02, ASTM S957-86 and ASTM D4662-03, respectively.

$^1$H-NMR spectra were recorded in $CDCl_3$ on a Varian Unity-INOVA at 499.695 MHz. $^1$H chemical shifts are internally referenced to CDCl₃ (7.26 ppm). All spectra were obtained using an 8.6 µs pulse with 4 transients collected in 16 202 points. Datasets were zero-filled to 64 000 points, and a line broadening of 0.4 Hz was applied prior to Fourier transforming the sets. The spectra were processed using ACD Labs NMR Processor, version 12.01.

HPLC analysis was performed on a Waters Alliance (Milford, Mass.) e2695 HPLC system fitted with a Waters ELSD 2424 evaporative light scattering detector. The HPLC system was equipped with an inline degasser, a pump, and an auto-sampler. The ELSD nitrogen flow was set at 25 psi with nebulization and drifting tube maintained at 12° C. and 55° C., respectively. Gain was set at 500. All solvents were HPLC grade and obtained from VWR International, Mississauga, ON. The analysis was performed on a Betasil Diol column (250 mm×4.0 mm, 5.0 µm). The temperature of the column was maintained at 50° C. The mobile phase was started with heptane: ethyl acetate (90:10)v run for 1 min at a flow rate of 1 mL/min and in a Gradient mode, then was changed to heptane: ethyl acetate (67:33) in 55 min and then the ratio of Ethyl acetate was increased to 100% in 20 min and held for 10 min. 5 mg/ml (w/v) solution of crude sample in chloroform was filtered through single step filter vial, and 4 µL of sample was passed through the diol column by normal phase in Gradient mode. Waters Empower Version 2 software was used for data collection and data analysis. Purity of eluted samples was determined using the relative peak area.

Physical Characterization Techniques for Polyols from PMTAG Fractions

TGA was carried out on a TGA Q500 (TA Instruments, DE, USA) equipped with a TGA heat exchanger (P/N 953160.901). Approximately 8.0-15.0 mg of sample was loaded in the open TGA platinum pan. The sample was heated from 25 to 600° C. under dry nitrogen at a constant rate of 10° C./min.

DSC measurements of the PMTAG Polyol were run on a Q200 model (TA Instruments, New Castle, Del.) under a nitrogen flow of 50 mL/min. PMTAG Polyol samples between 3.5 and 6.5 (±0.1) mg were run in standard mode in hermetically sealed aluminum DSC pans. The sample was equilibrated at 90° C. for 10 min to erase thermal memory, and then cooled at 5.0° C./min to −90° C. where it was held isothermally for 5 min, and subsequently reheated at a constant rate of 5.0° C./min to 90° C.

"TA Universal Analysis" software was used to analyze the DSC and TGA. Characteristics of non-resolved peaks were obtained using the first and second derivatives of the signal.

SFC measurements were performed on a Bruker Minispec mq 20 pNMR spectrometer (Milton, ON, Canada) equipped with a combined high and low temperature probe supplied with N₂. The temperature was controlled with Bruker's BVT3000 temperature controller with an accuracy of ±0.1° C. The temperature was calibrated with commercial canola oil using a type K probe (TRP-K, Omega, Stamford, Conn.) immersed in the oil and an external data logger (Oakton, Eutech Instruments, Singapore). Approximately 0.57±0.05 ml of fully melted sample was quickly pipetted into the bottom portion of the NMR tube. The thermal protocol used in the DSC was also used in the NMR. Bruker's minispec V2.58 Rev. 12 and minispec plus V1.1 Rev. 05 software were used to collect SFC data as a function of time and temperature. The SFC values are reported as the ratio of the intensity of the NMR signal of the solid part to the total detected NMR signal in percent (labelled as SFC %).

A temperature-controlled Rheometer (AR2000ex, TA Instruments, DE, USA) was used to measure the viscosity and flow property of the PMTAG Polyol using a 40 mm 2° steel geometry. Temperature control was achieved by a Peltier attachment with an accuracy of 0.1° C. The shear rate range (1 to 1200 s⁻¹) was optimized for torque (lowest possible is 10 µNm) and velocity (maximum suggested of 40 rad/s). Measurements were taken at 10° C. intervals from high temperature (typically ~100° C.) to 10° C. below the DSC onset of crystallization temperature of each sample. Viscosities of samples were measured from each sample's melting point up to ~110° C. at constant temperature rate (1.0 and 3.0° C./min) with constant shear rate (200 s⁻¹). Data points were collected at intervals of 1° C. The viscosity obtained in this manner was in agreement with the viscosity obtained using shear rate/share stress curve.

A Leica DM2500P polarized light microscope (PLM) fitted with a Leica DFC420C digital camera (Leica Microsystems, Wetzlar, Germany) was used to follow microstructure development of the polyols. The samples were processed in a temperature-controlled stage (Linkam LTS 350) fitted to the PLM. The sample was equilibrated at 100° C. for 10 min to erase thermal memory, and then cooled at 5.0° C./min to 25° C.

A TA-HD plus texture analyzer (Stable Microsystems, Surrey, UK) fitted with a 5.0 kg load cell and with the ASTM D1321 standard needle (Model H1310, Humboldt Mfg. Co., Schiller Park, Ill., USA) was used for penetration measurements. Penetration was performed at a constant speed of 0.5 mm/s to a fixed depth of 2.5 mm according to an optimization procedure developed by procedures known in the literature (Boodhoo M V, Humphrey K L, and S S Narine, (2009) *Relative Hardness of Fat Crystal Networks Using Force Displacement Curves*, International Journal of Food Properties, V12, pp 129-144). Penetration experiments were controlled by Exponent Software Version 4.0.13.0 (Stable Microsystems, Surrey, UK).

Compositional Analysis of the Polyol Fractions

OH and Acid Values

OH and acid values of the standard solid and liquid fractions of PMTAG Polyol are listed in Table 11. Iodine, OH and acid values of solid and liquid fractions of PMTAG Green Polyol (SF-Green Polyol and LF-Green Polyol) are listed in Table 11. As listed in Table 11, the polyols presented very low acid values and high OH numbers.

TABLE 11

OH and acid values of the solid and liquid fractions of standard PMTAG Polyol and solid and liquid fractions of Green Polyol. Data for standard PMTAG Polyol and PMTAG Green Polyol are also listed for comparison purposes

| Fraction | Iodine Value | OH value | Acid value (mg KOH/g) |
|---|---|---|---|
| PMTAG Polyol | NA | 155 | 3 |
| LF-Polyol | NA | 150 | 4 |
| SF-Polyol | NA | 156 | 4 |
| PMTAG Green Polyol | 8 | 119 | 1.3 |
| LF-Green Polyol | 8 | 117 | 2.7 |
| SF-Green Polyol | 6 | 104 | 2.7 |

¹H-NMR Results of Standard LF- and SF-Polyols

Figure 11A:
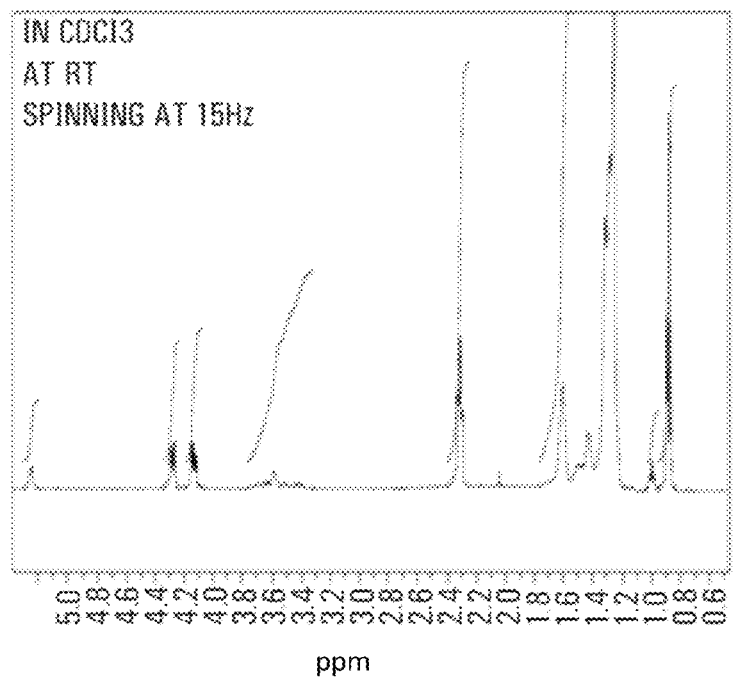
FIG. 11A depicts $^1$H-NMR spectrum of SF-Polyol.
Figure 11B:
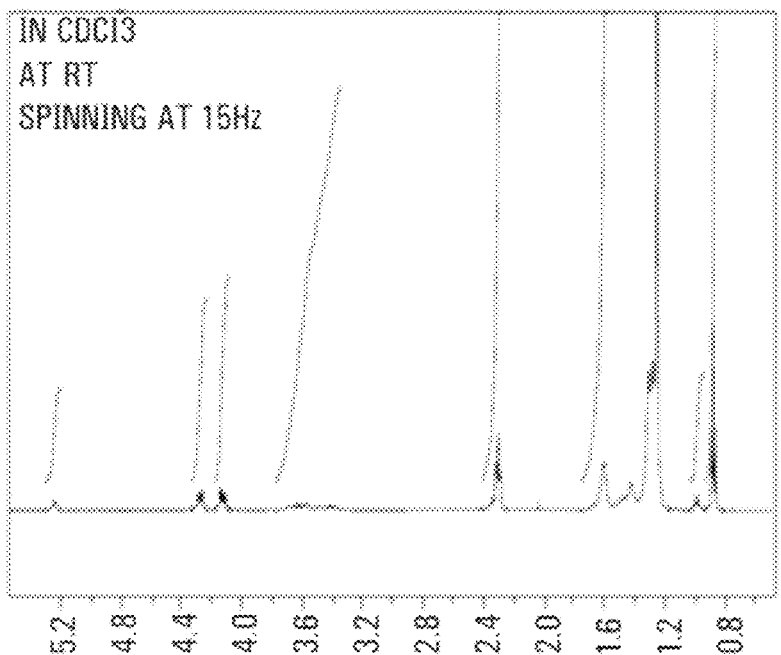
FIG. 11B depicts $^1$H-NMR spectrum of LF-Polyol.

The ¹H-NMR of the solid and liquid polyol fractions are shown in FIGS. 11A and 11B, respectively. The related ¹H-NMR chemical shifts, δ, in CDCl₃ are listed in Table 12.

The spectra of the polyols presented the chemical shifts at 3.8-3.4 ppm related to protons neighbored by —OH and did not present the chemical shifts at 2.8-2.4 ppm related to epoxy ring. The chemical shifts at 1.0 ppm related to terminal butyl and 0.8 ppm related to terminal oleyl were also presented. The ration of terminal butyl —CH₃: terminal oleyl —CH₃ was 1:7.4 for SF-Polyol and 1:4.8 in LF-Polyol, indicating that much less butyl terminal fatty acids were in SF-polyol than in LF-polyol.

TABLE 12

¹H-NMR chemical shifts, δ, of LF-Polyol and SF-Polyol

| | ¹H-NMR Chemical shifts, δ, in CDCl₃ (ppm) |
|---|---|
| SF-Polyol | 5.2 (m), 4.4-4.2 (dd), 4.2-4.0 (dd), 3.8-3.2 (m), 2.4-2.2 (m), 1.6-1.2 (m), 1.0 (t), 0.8 (t) |
| LF-Polyol | 5.2 (m), 4.4-4.2 (dd), 4.2-4.0 (dd), 3.8-3.2 (m), 2.4-2.2 (D2), 1.6-1.2 (m), 1.0 (t), 0.8 (t) |

Structures of SF- and LF-Polyol
Potential Composition of Liquid and Solid Fractions of PMTAG Polyol The natural oil composition, and in particular, the palm oil composition and the TAG profiles of palm oil were also described previously in commonly assigned U.S. Provisional Patent Application No. 61/971,475. The theoretical structures of PMTAG Polyol based on the TAG analysis of palm oil are given below in Scheme 6. The actual composition of the PMTAG Polyols was characterized by ¹H-NMR and HPLC.

Figure 12A:
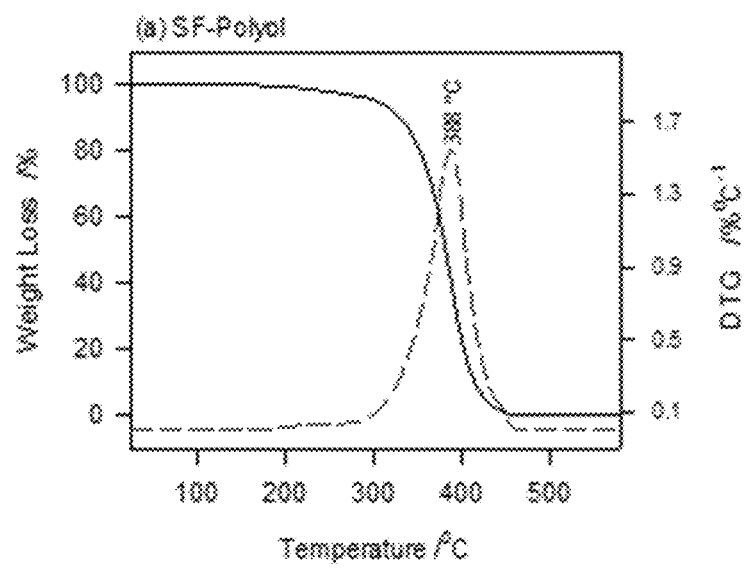
FIG. 12A depicts TGA and DTG profiles of SF-Polyol.
Figure 12B:
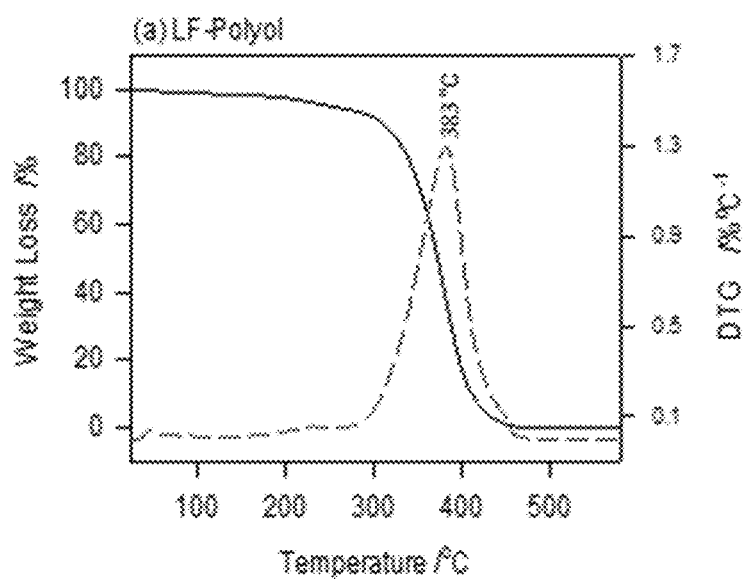
FIG. 12B depicts TGA and DTG profiles of LF-Polyol.
Figure 12C:
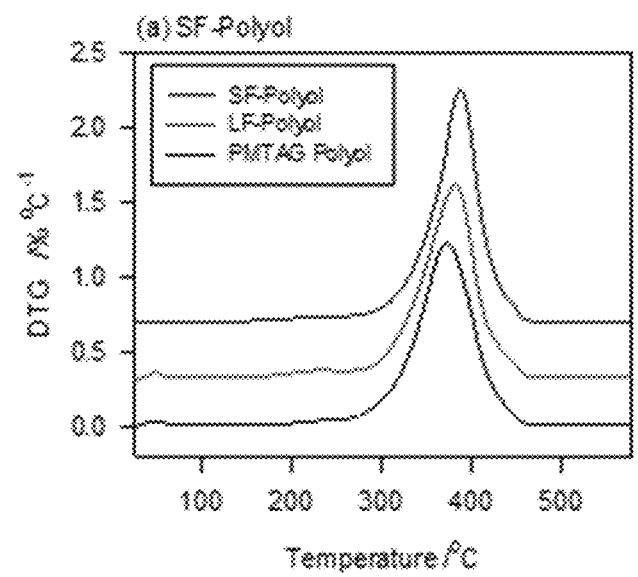
FIG. 12C depicts stacked DTG profiles of LF- and SF-Polyols with DTG of PMTAG Polyol.

Physical Properties of PMTAG Fractions
Thermogravimetric Analysis of SF- and LF-PMTAG Polyols The TGA and DTG profiles of SF- and LF-Polyols are shown in FIGS. 12A and 12B, respectively. For comparison purposes, the DTG curves of the liquid and solid polyol fractions are presented in FIG. 12C. The corresponding data (extrapolated onset and offset temperatures of degradation, temperature of degradation measured at 1, 5 and 10% decomposition, and the DTG peak temperatures) are provided in Table 13.

The TGA and DTG data indicate that polyols fractions undergo degradation mechanisms similar to the PMTAG Polyol itself. The DTG curves presented a very small first DTG peak ($T_{D1}$ in FIG. 12) that involved ~1 to 4% weight loss only followed by a very a large peak at ~385° C. with ~60% weight loss ($T_D$ in FIG. 12) indicating that degradation occurred mainly in one step. This dominant mechanism of degradation was also observed in the TGA of the PMTAG Polyol starting material and is associated with the breakage of the ester bonds.

The thermal stability of the liquid fraction was similar to the PMTAG polyol itself both relatively lower thermal stability than SF-Polyol (see Table 14). SF-Polyol presented an extrapolated onset of thermal degradation 10° C. higher than that of LF-Polyol and recorded 5% weight loss at 304° C., 40° C. higher than LF-Polyol.

Scheme 6. Possible structures in SF- and LF- PMTAG Polyol

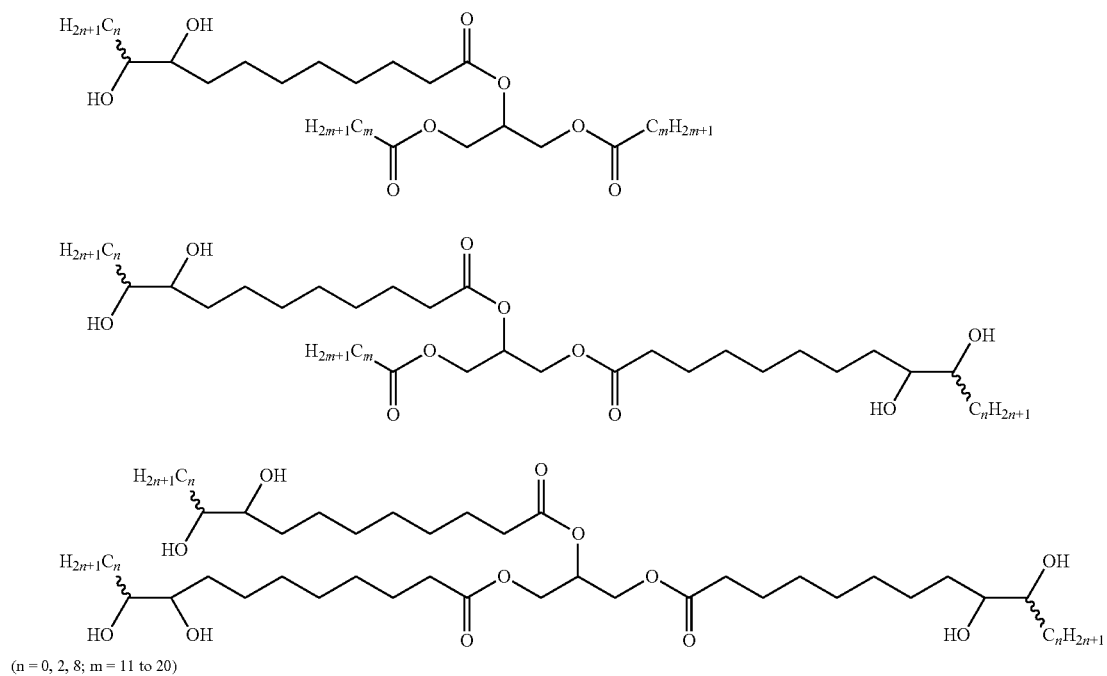

(n = 0, 2, 8; m = 11 to 20)

TABLE 13

Temperature of degradation at 1, 5 and 10% weight loss ($T_{1\%}^d$, $T_{5\%}^d$, $T_{10\%}^d$, respectively), DTG peak temperatures ($T_D$), and extrapolated onset ($T_{on}$) and offset ($T_{off}$) temperatures of degradation of LF- and SF-Polyols

| | Temperature (° C.) | | | | | | | Weight loss (%) at | | |
|---|---|---|---|---|---|---|---|---|---|---|
| | $T_{1\%}^d$ | $T_{5\%}^d$ | $T_{10\%}^d$ | $T_{on}$ | $T_{D1}$ | $T_D$ | $T_{off}$ | $T_{on}$ | $T_{D1}$ | $T_D$ |
| PMTAG Polyol | 215 | 295 | 320 | 305 | 227 | 374 | 415 | 6 | 1.5 | 53 |
| SF-Polyol | 213 | 304 | 353 | 309 | 233 | 389 | 417 | 5.5 | 1.5 | 60 |
| LF-Polyol | 138 | 262 | 314 | 322 | 232 | 383 | 417 | 13 | 4 | 62 |

Crystallization and Melting Behavior of SF- and LF-Polyols

Figure 13A:
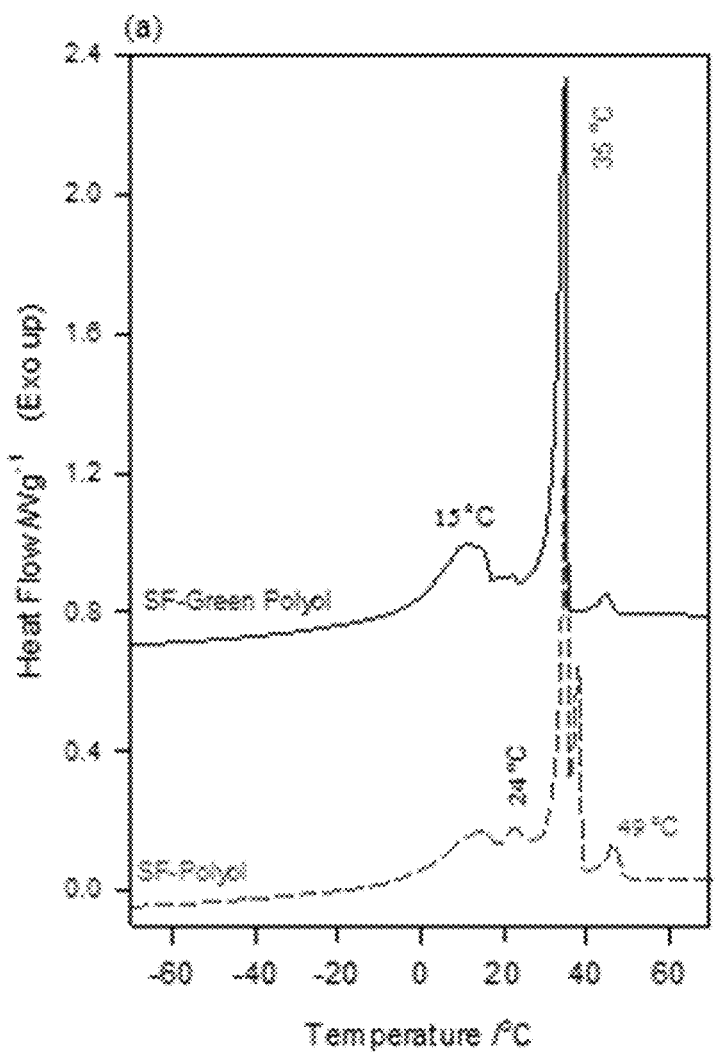
FIG. 13A depicts DSC thermograms of solid polyol fraction during cooling at 5° C./min.
Figure 13B:
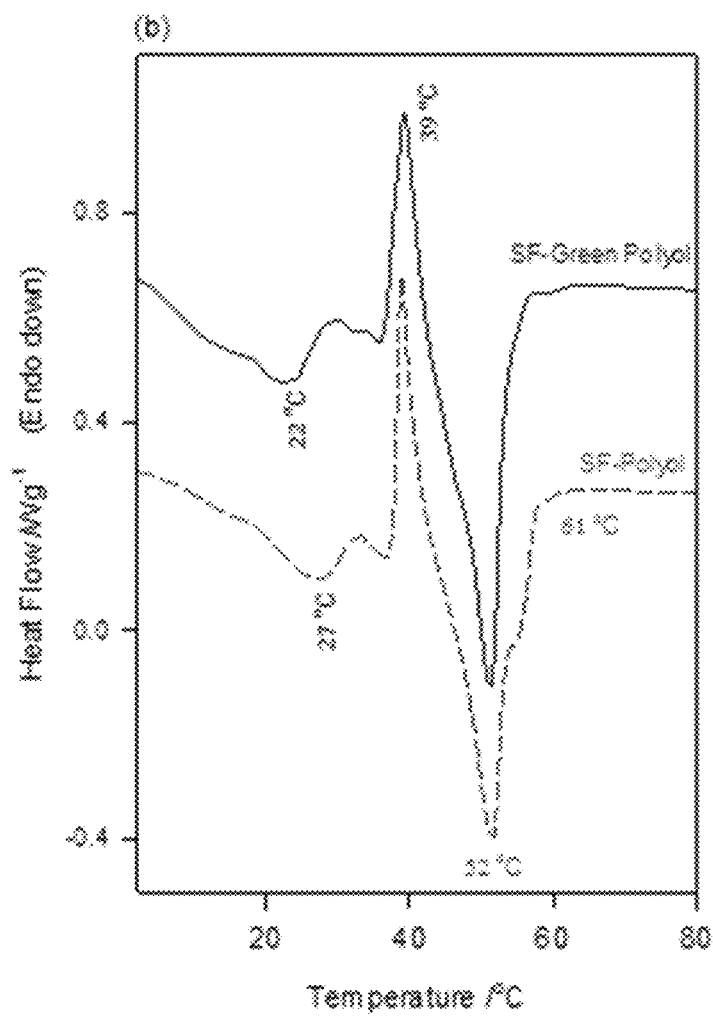
FIG. 13B depicts DSC thermograms of solid polyol fraction during subsequent heating at 5° C./min.
Figure 14A:
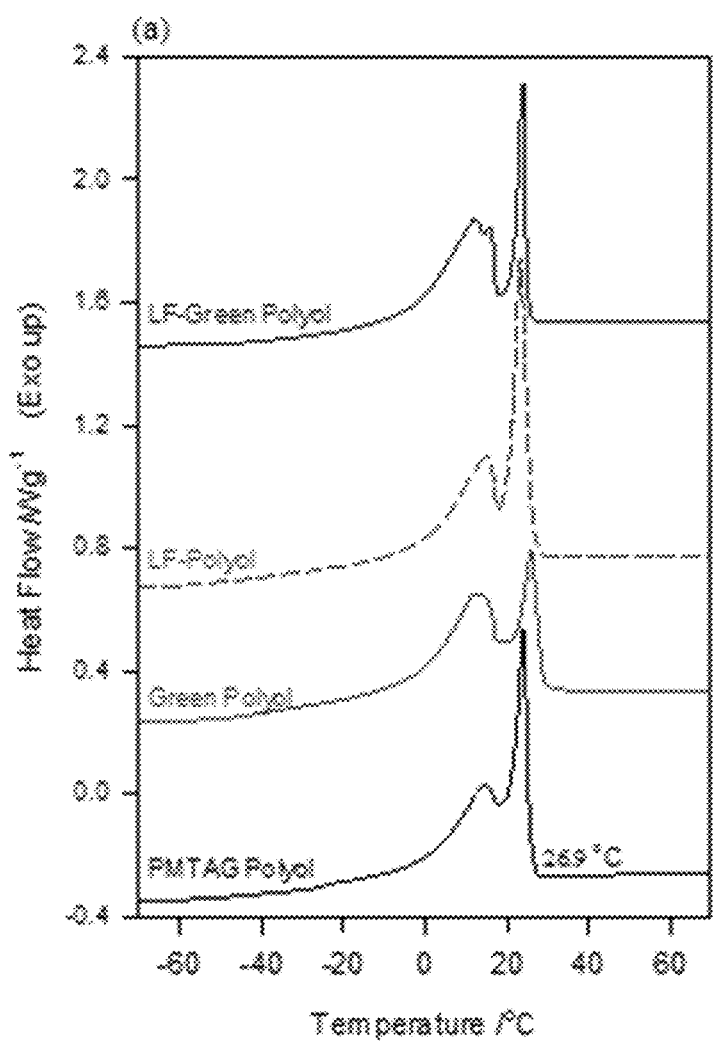
FIG. 14A depicts DSC thermograms of liquid polyol fractions during cooling at 5° C./min.
Figure 14B:
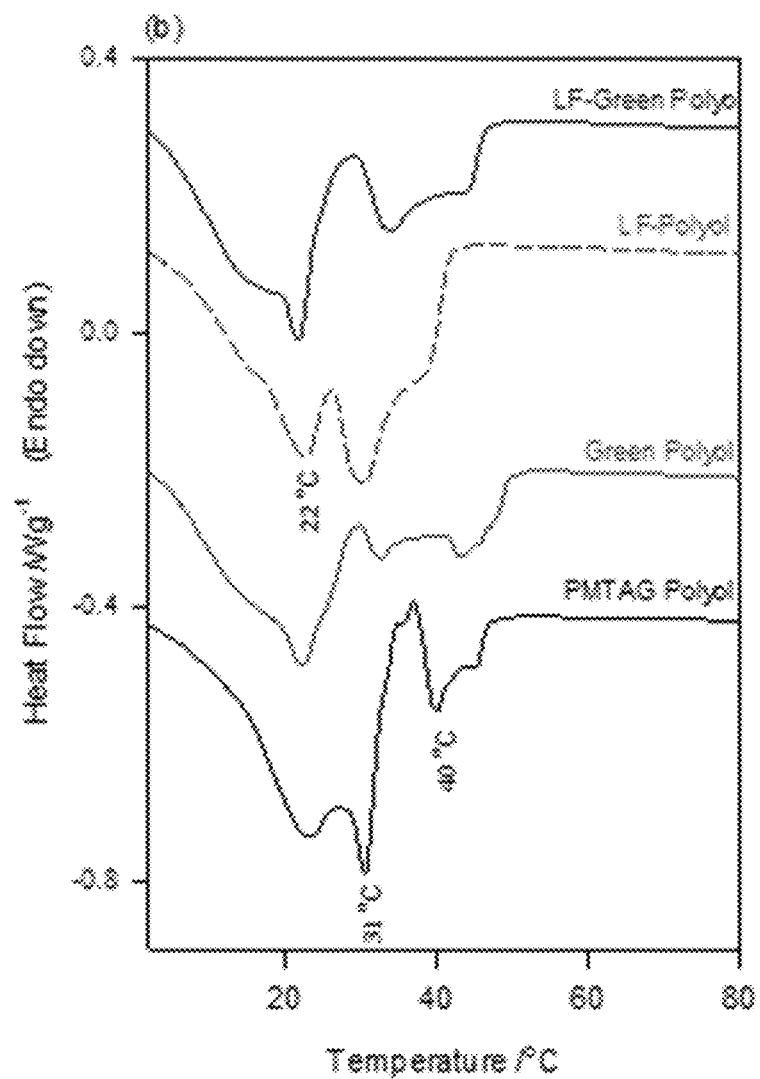
FIG. 14B depicts DSC thermograms of liquid polyol fractions during subsequent heating at 5° C./min.

The crystallization and heating profiles (both at 5° C./min) of SF-Polyol, are shown in FIGS. 13A and 13B, respectively. Those of LF-Polyol, are shown in FIGS. 14A and 14B, respectively. The DSC traces of PMTAG Polyol and PMTAG Green Polyol are also represented in FIGS. 14A and 14B for comparison purposes. The corresponding thermal data are listed in Table 14.

SF-Polyol crystallized well above sub ambient temperature ($T_{on}$ ~49° C.); whereas, LF-Polyol crystallized at ambient temperature ($T_{on}$ ~26° C.) similarly to the starting PMTAG Polyol. Five defined peaks were observed in the cooling thermograms of SF-Polyol (FIG. 13A) and only two in LF-Polyol (FIG. 14A). The first three peaks in the cooling thermogram of SF-Polyol are all above 27° C., the onset temperature of crystallization of the starting polyol, indicating a very selective fractionation. Furthermore, the peak at 27° C. was very weak compared to LF-Polyol and PMTAG Polyol, indicating that the high temperature crystallizing compounds developed a higher stability phase than in the starting polyol. Note that the solid fraction of the green polyol differed only slightly from SF-Polyol, in that it did present two peaks only above 27° C., suggesting a somehow different composition.

The heating thermogram of SF-Polyol displayed two groups of endothermic events separated by a strong exotherm (G1, G2 and R in FIG. 14B). One can notice that the lowest temperature endotherm of PMTAG Polyol at ~23 C, almost disappeared from the thermogram of SF-Polyol, indicating that SF-Polyol was depleted from the lowest melting compounds of the polyol. LF-Polyol did not display any exotherm, and similarly to the starting PMTAG Polyol presented the traces of melting of the low and high melting portion of the polyol (FIG. 14B).

The DSC data indicate that although LF-Polyol was depleted from some of the high melting components, it retained all of the species of the starting polyol. The significantly different thermal behavior of SF-PMTAG was probably due to a peculiar composition that favored early crystallization and strong polymorphic transformation.

TABLE 14

Thermal data of LF- and SF-Polyols obtained on cooling and heating (both at 5° C./min). Onset ($T_{on}$), offset ($T_{off}$), and peak temperatures ($T_{i=1-5}$ $T_{i=1-5}$), Enthalpy of crystallization ($\Delta H_C$), and Enthalpy of melting ($\Delta H_M$).

| Cooling | Temperature (° C.) | | | | | | | Enthalpy (J/g) |
|---|---|---|---|---|---|---|---|---|
| | $T_{on}$ | $T_1$ | $T_2$ | $T_3$ | $T_4$ | $T_5$ | $T_{off}$ | $\Delta H_C$ |
| PMTAG Polyol | −4.35 | — | — | — | 24.07 | 13.83 | | 94.1 |
| SF-Polyol | 49.28 | 46.71 | 38.19 | 35.30 | 22.17 | 14.66 | −12.36 | 109.6 |
| LF-Polyol | 26.07 | — | — | — | 23.31 | 15.10 | −3.11 | 101.2 |
| PMTAG Green Polyol | 28.63 | — | — | — | 26.00 | 12.57 | −7.28 | 87.1 |
| SF-Green Polyol | 47.39 | 44.79 | — | 34.91 | 22.17 | 12.83 | −5.89 | 117.7 |
| LF-Green Polyol | 24.83 | — | — | — | 23.91 | 11.87 | −6.99 | |

| Heating | $T_{on}$ | $T_1^a$ | $T_2$ | $T_3$ | $T_4$ | $T_5^a$ | $T_{off}$ | $\Delta H_M$ |
|---|---|---|---|---|---|---|---|---|
| PMTAG Polyol | −1.38 | 45.28 | 40.21 | 30.42 | 22.43 | — | 47.07 | 93.3 |
| SF-Polyol | 4.55 | 55.4 | 51.57 | 36.61 | 27.22 | 15.2 | 61.37 | 104.8 |
| LF-Polyol | 1.24 | 37.2 | | 30.52 | 2268 | 15.5 | 41.71 | 98.3 |
| PMTAG Green Polyol | 1.52 | 43.39 | | 32.34 | 22.40 | 14.5 | 49.52 | 91.6 |
| SF-Green Polyol | −0.08 | 51.25 | — | 35.94 | 22.17 | 13.84 | 63.66 | 121.8 |
| LF-Green Polyol | 0.18 | 43.5 | — | 33.80 | 21.73 | 14.47 | 46.21 | 88.9 |

$^a$Shoulder peak

Figure 15A:
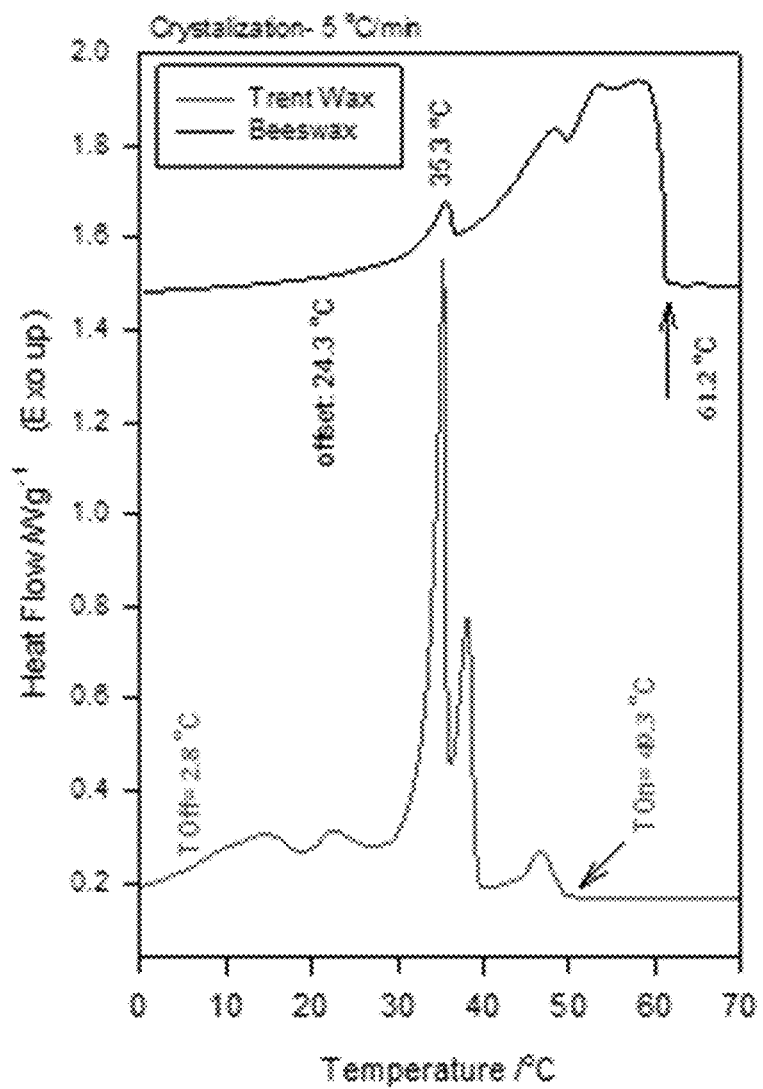
FIG. 15A depicts DSC thermograms of SF-Polyol and beeswax compared during cooling at 5° C./min.
Figure 15B:
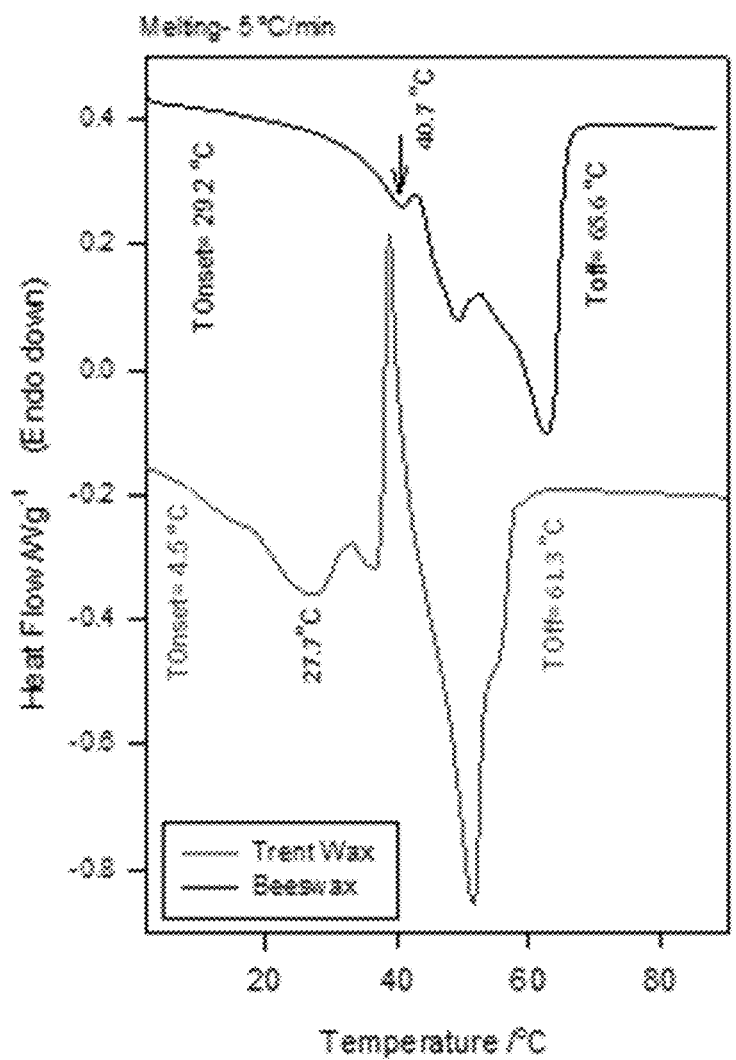
FIG. 15B depicts DSC thermograms of SF-Polyol and beeswax compared during subsequent heating at 5° C./min.

As can be seen in FIGS. 15A and 15B, SF-Polyol crystallized at a lower temperature than beeswax (49.3 compared to 61.2° C.) and presented a crystallization signal in which single exotherms were much more defined. Also, offset temperature of crystallization SF-Polyol was much lower than that of beeswax (24.3 compared to 2.8° C.). Furthermore, contrary to beeswax, the solid fraction of the polyol showed an intense recrystallization peak indication polymorphic transformation. Note that offset temperature of melting of SF-Polyol was relatively close to that of beeswax (61.3 compared to 65.6° C.)

Solid Fat Content of LF- and SF-Polyols

Figure 16A:
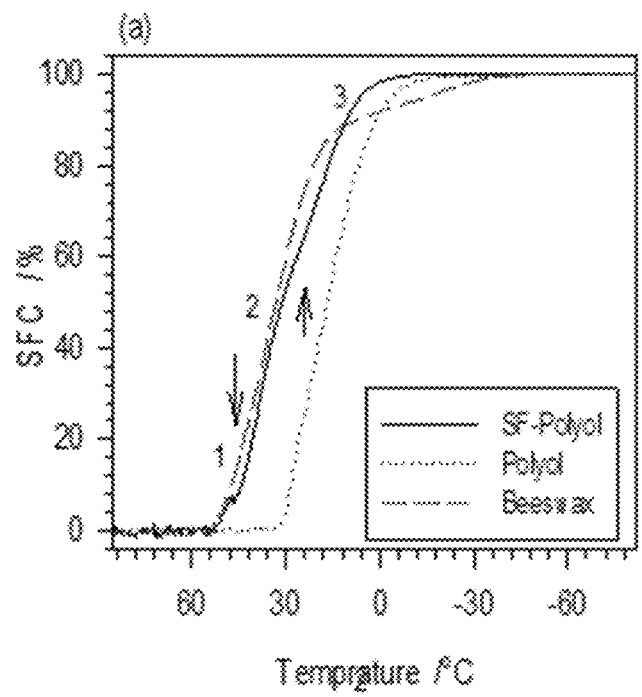
FIG. 16A depicts SFC versus temperature of SF-Polyol and beeswax during cooling at 5° C./min.
Figure 16B:
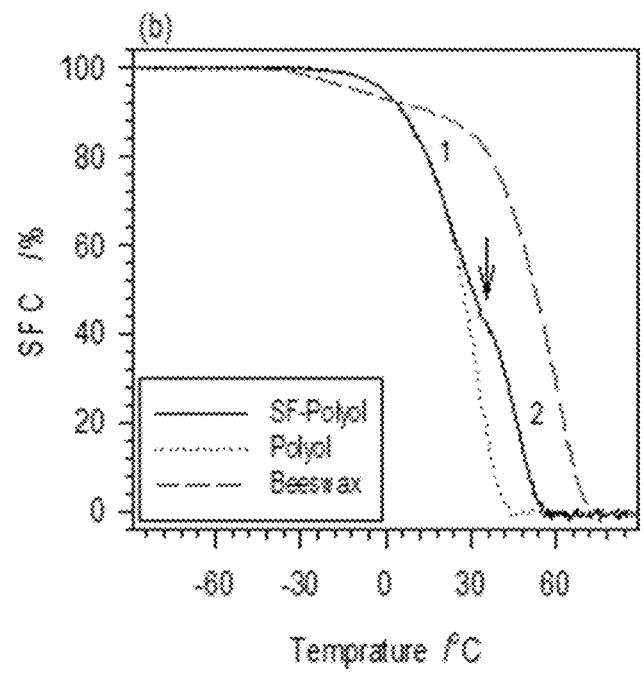
FIG. 16B depicts SFC versus temperature of SF-Polyol and beeswax during subsequent heating at 5° C./min. SFC versus temperature of PMTAG Polyol is also shown for comparison purposes.

Solid Fat Content (SFC) versus temperature curves on cooling (5° C./min) and heating (5° C./min) of the solid polyol fractions are shown in FIGS. 16A and 16B, respectively. SFC versus temperature of beeswax and PMTAG Polyol are also shown for comparison purposes. The starting PMTAG Polyol is shown in the figures for comparison purposes. Extrapolated induction and offset temperatures as determined by SFC during cooling and heating are listed in Table 15.

As can be seen in FIG. 16A, contrary to the starting PMTAG Polyol which presented only one segment in both its heating and cooling SFC traces, SF-Polyol presented three segments on cooling, and a two identifiable segments on heating (segments 1 and 2 in FIG. 16B) indicating the melting of two different portion of the polyol. The SFC traces of SF-Polyol mirrored what was observed in the DSC. The SFC solidification segments are associated with the exotherms of the crystallization process. The first segment in the SFC cooling cycle (segment 1 in FIG. 16A) is associated with the leading DSC peak of FIG. 13A, the second segment with the following main exotherm and the third segment with the remaining exotherm. The distinction between the components that melt at high and low temperature was not captured by the SFC of the PMTAG Polyol, probably because of the relatively high rate of cooling and heating (5 C).

The induction and offset temperatures of solidification of SF-Polyol (~51.5 and 55.6° C., respectively) were higher than those of PMTAG Polyol (30.8 and 43.8° C., respectively) in accordance with DSC findings.

TABLE 15

Extrapolated induction and offset temperatures ($T_{ind}$, $T_s$, respectively) of LF- and SF-PMTAG Polyols as determined by SFC

| Temperature (° C.) | Cooling | | Heating | |
| --- | --- | --- | --- | --- |
| | $T_{ind}$ | $T_s$ | $T_{ind}$ | $T_s$ |
| SF-Polyol | 51.5 | 1.3 | −23.9 | 55.6 |
| PMTAG Polyol | 30.8 | −2.9 | −21.2 | 43.8 |

Viscosity of SF-Polyol

Figure 17A:
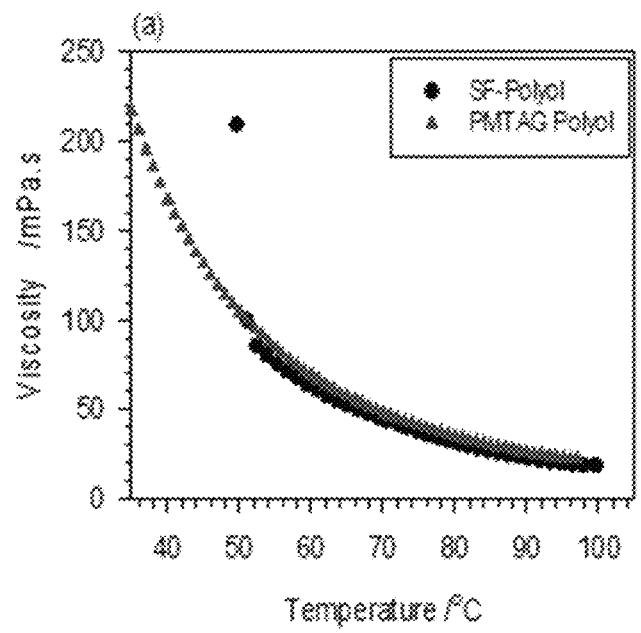
FIG. 17A depicts viscosity versus temperature curves obtained during cooling (1° C./min) of SF-Polyol and PMTAG Polyol.

FIG. 17A shows the viscosity versus temperature curves obtained during cooling at 1° C./min for SF-Polyol. Viscosity versus temperature curve of PMTAG Polyol is also presented for comparison purposes. Also, viscosity versus temperature curve of beeswax is compared with SF-Polyol in FIG. 17B.

The viscosity versus temperature of SF-Polyol presented the typical exponential behavior of liquid hydrocarbons. As can be seen in FIG. 17A, SF-Polyol displayed relatively lower viscosity than PMTAG Polyol at all temperatures above the crystallization point. The difference is small and ranges from ~30 mPas at 55° C. to 4 mPas at 70° C.

Figure 17B:
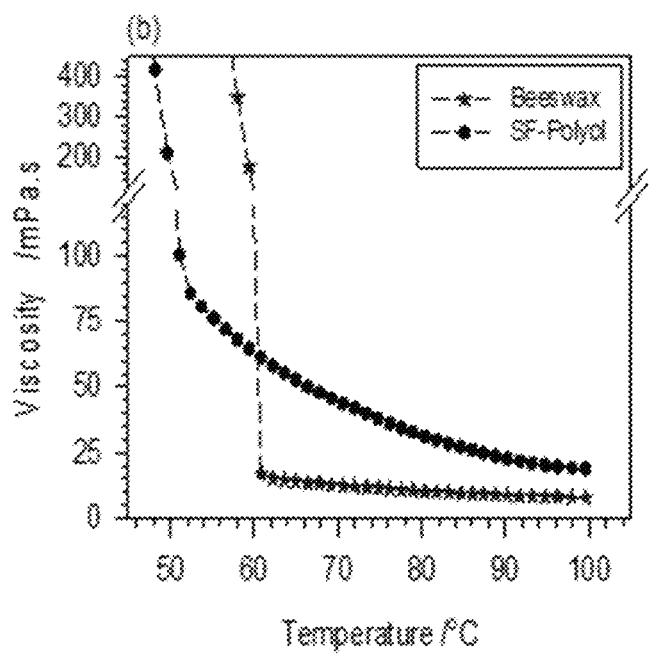
FIG. 17B depicts viscosity of SF-Polyol compared to beeswax.
Figure 18A:
FIGS. 18A-18F depicts microstructure development of SF-Polyol during cooling (5° C.) from the melt. Temperature and magnification at which the images were taken are indicated on top of the figures.
Figure 18B:
Figure 18C:
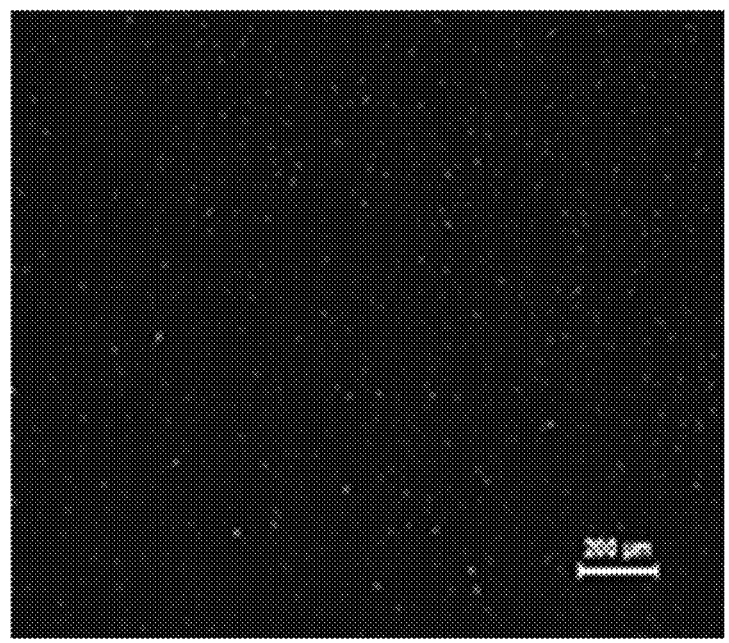
Figure 18D:
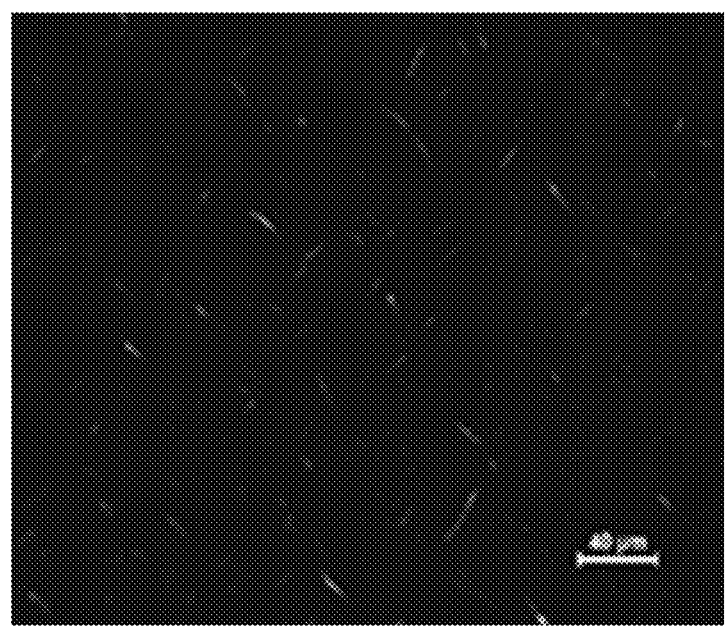
Figure 18E:
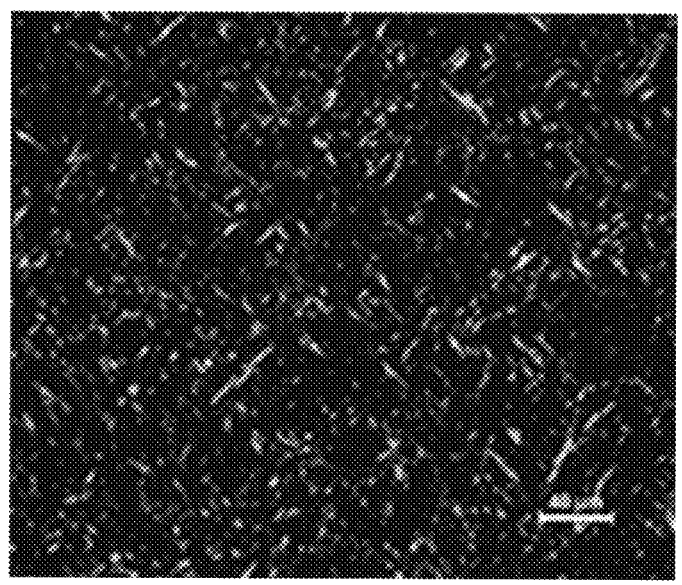
Figure 18F:
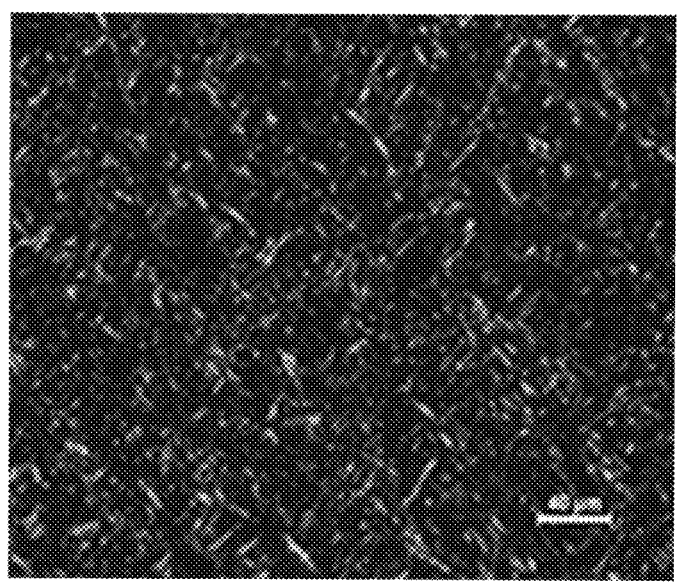

As can be seen in FIG. 17B, Viscosity of SF-Polyol is higher than that of beeswax before the onset of solidification. The difference is relatively small in the liquid state and decreases with increasing temperature. It ranges from ~44 mPas at 60° C. to 11 mPas at 100° C.

Microstructure Development of SF- and LF-Polyol

The microstructural analysis was performed in order to determine the microstructure size, shape, development kinetics and final network formation. The development of the microstructure was followed while the sample was cooling (5° C./min) from the melt to room temperature. FIGS. 18A-18F highlight the development of the microstructure of SF-Polyol during cooling at 5° C./min. PLM images (500×) of SF-Polyol and beeswax obtained at 25° C. are presented in FIG. 19 for comparison purposes.

Very small fibril-like crystals were observed first at ~50.1±0.5° C., a temperature close to the DSC onset of crystallization. Their number increased rapidly and developed into a very dense network. The average crystal size was 20±5 μm. The small size of the crystals is not unexpected as high cooling rates usually lead to the formation of small microstructures. The rapid development of the microstructure indicates that 5° C./min would not be a suitable rate for fractionating the polyol.

Figure 19A:
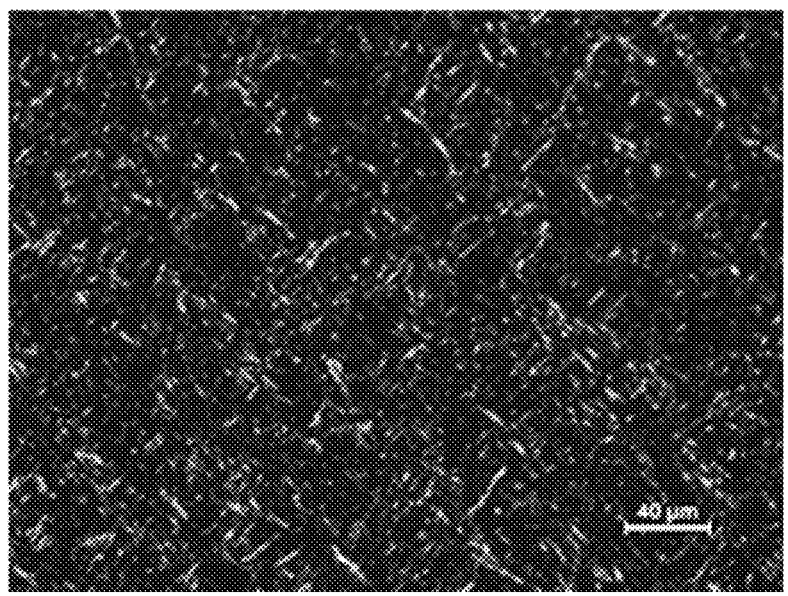
FIG. 19A depicts PLM images (500×) of SF-Polyol obtained at 25° C.
Figure 19B:
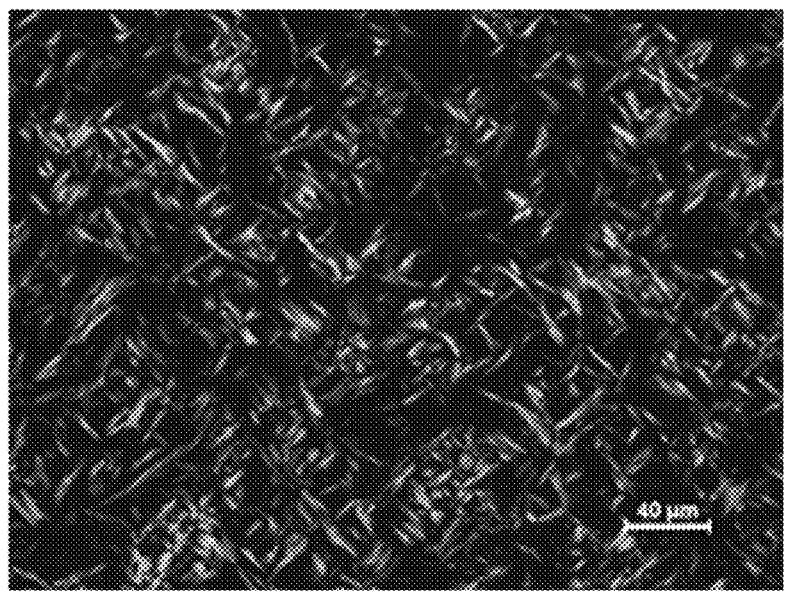
FIG. 19B depicts PLM images (500×) of beeswax obtained at 25° C.

As can be seen in FIG. 19, although slightly larger and better defined, SF-Polyol presented closely similar dense network of fibril-like crystals to those observed in beeswax.

Hardness of SF-Polyol

Figure 20:
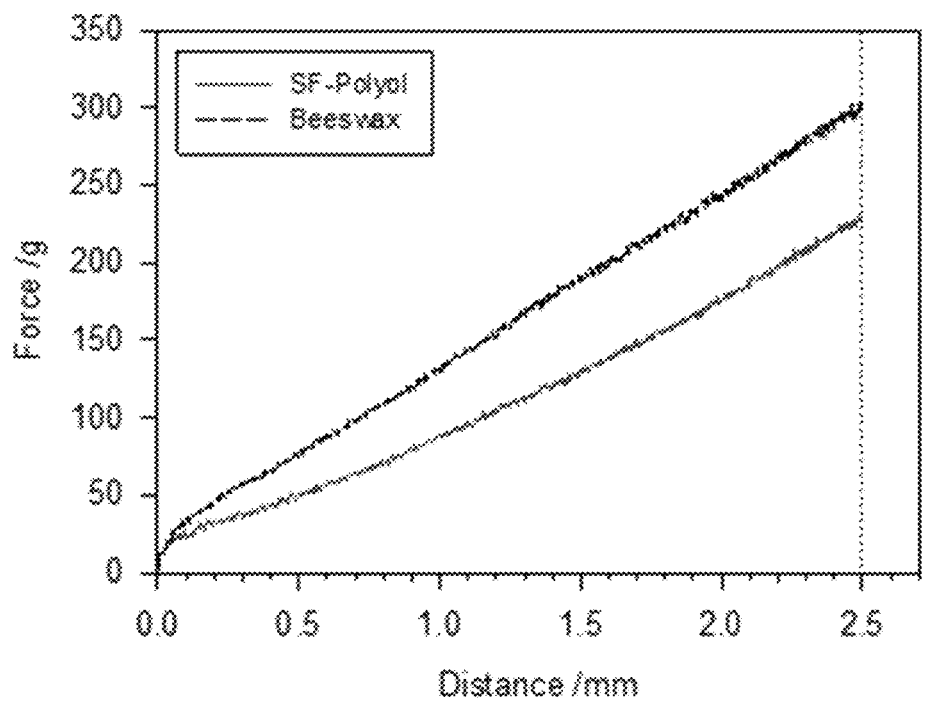
FIG. 20 depicts penetration versus distance of SF-Polyol and beeswax measured at 25° C.

The sample was melted at 80° C., poured into molds then left at room temperature for 4 h, and tested at room temperature. Penetrometry data are the average of five (5) sample runs. Penetration distance versus force for SF-Polyol is presented with that of beeswax in FIG. 20. Force at 2.5 mm penetration was 228.2±1.5 g. for SF-Polyol and 306.6±8.3 g for beeswax.

Polyurethane Foams from Polyols or Fractions Thereof

Polyurethane Foam Polymerization

Polyurethanes are one of the most versatile polymeric materials with regards to both processing methods and mechanical properties. The proper selection of reactants enables a wide range of polyurethanes (PU) elastomers, sheets, foams etc. Polyurethane foams are cross linked structures usually prepared based on a polymerization addition reaction between organic isocyanates and polyols, as generally shown in Scheme 7 below. Such a reaction may also be commonly referred to as a gelation reaction.

Scheme 7. General formation of urethane linkage between isocyanate group and OH group

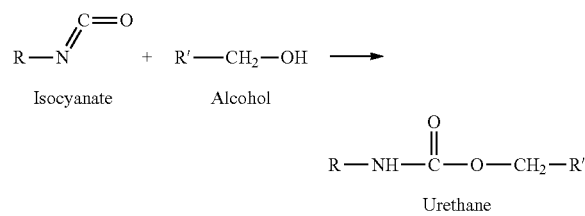

A polyurethane is a polymer composed of a chain of organic units joined by the carbamate or urethane link. Polyurethane polymers are usually formed by reacting one or more monomers having at least two isocyanate functional groups with at least one other monomer having at least two isocyanate-reactive groups, i.e. functional groups which are reactive towards the isocyanate function. The isocyanate ("NCO") functional group is highly reactive and is able to react with many other chemical functional groups. In order for a functional group to be reactive to an isocyanate functional group, the group typically has at least one hydrogen atom which is reactive to an isocyanate functional group. A polymerization reaction is presented in Scheme 8, using a hexol structure as an example.

Scheme 8. Preparation of cross linked polyuerthane from MDI and MTAG Polyols. Hexol structure is used as an example.

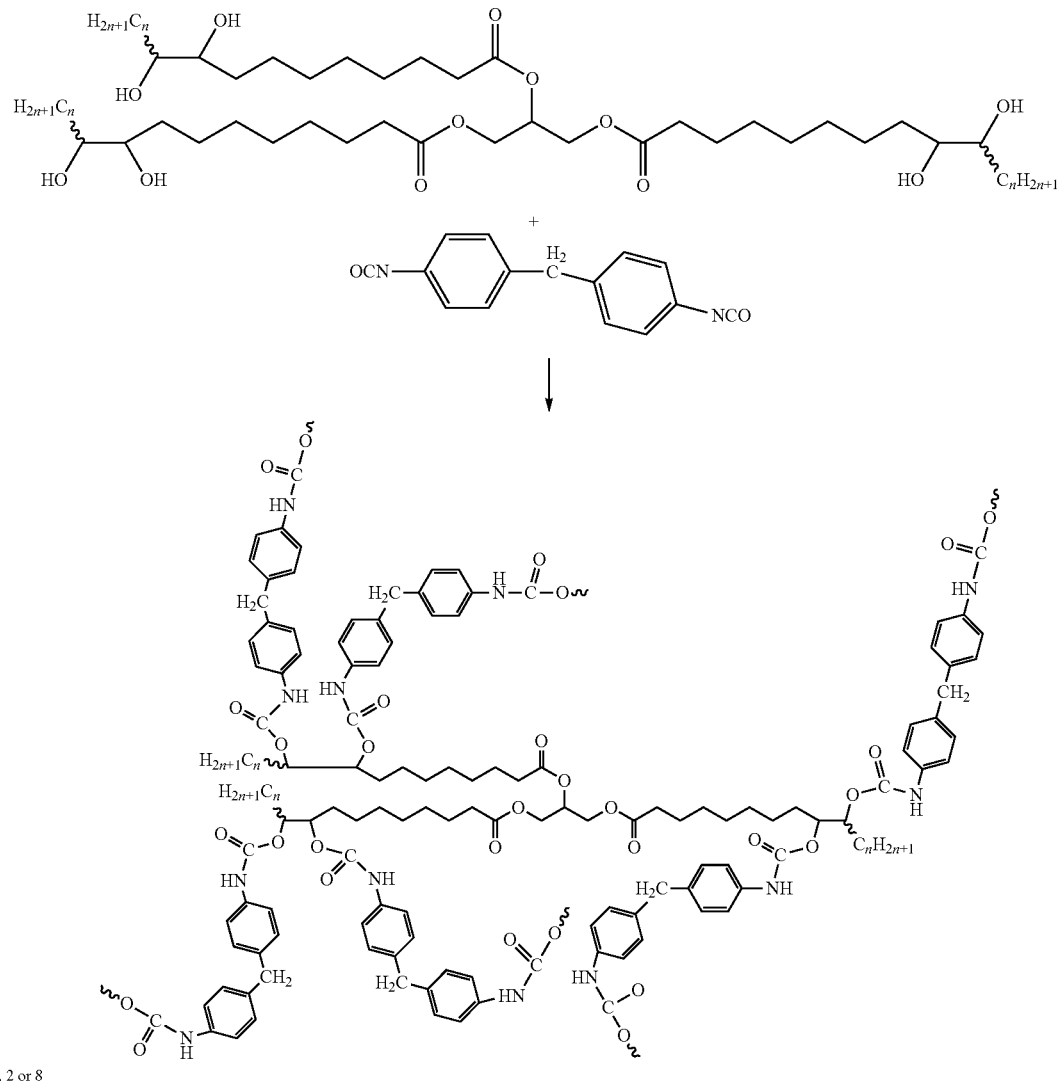

n = 0, 2 or 8

In addition to organic isocyanates and polyols, foam formulations often include one or more of the following non-limiting components: cross-linking components, blowing agents, cell stabilizer components, and catalysts. In some embodiments, the polyurethane foam may be a flexible foam or a rigid foam.

Organic Isocyanates

The polyurethane foams of the present invention are derived from an organic isocyanate compound. In order to form large linear polyurethane chains, di-functional or poly-functional isocyanates are utilized. Suitable polyisocyanates are commercially available from companies such as, but not limited to, Sigma Aldrich Chemical Company, Bayer Materials Science, BASF Corporation, The Dow Chemical Company, and Huntsman Chemical Company. The polyisocyanates of the present invention generally have a formula $R(NCO)_n$, where n is between 1 to 10, and wherein R is between 2 and 40 carbon atoms, and wherein R contains at least one aliphatic, cyclic, alicyclic, aromatic, branched, aliphatic- and alicyclic-substituted aromatic, aromatic-substituted aliphatic and alicyclic group. Examples of polyisocyanates include, but are not limited to diphenylmethane-4, 4'-diisocyanate (MDI), which may either be crude or distilled; toluene-2,4-diisocyanate (TDI); toluene-2,6-diisocyanate (TDI); methylene bis(4-cyclohexylisocyanate) ($H_{12}$MDI); 3-isocyanatomethyl-3,5,5-trimethyl-cyclohexylisocyanate (IPDI); 1,6-hexane diisocyanate (HDI); naphthalene-1,5-diisocyanate (NDI); 1,3- and 1,4-phenylenediisocyanate; triphenylmethane-4,4',4"-triisocyanate; polyphenylpolymethylenepolyisocyanate (PMDI); m-xylene diisocyanate (XDI); 1,4-cyclohexyl diisocyanate (CHDI); isophorone diisocyanate; isomers and mixtures or combinations thereof.

Polyols

The polyols used in the foams described herein are based on the fractions of metathesized triacylglycerol (MTAG) derived from natural oils, including palm oil. The synthesis of the MTAG Polyol was described earlier, and involves epoxidation and subsequent hydroxylation of a fraction of an MTAG derived from a natural oil, including palm oil.

Cross-Linking Components and Chain Extenders

Cross-linking components or chain extenders may be used if needed in preparation of polyurethane foams. Suitable cross-linking components include, but are not limited to, low-molecular weight compounds containing at least two moieties selected from hydroxyl groups, primary amino groups, secondary amino groups, and other active hydrogen-containing groups which are reactive with an isocyanate group. Crosslinking agents include, for example, polyhydric alcohols (especially trihydric alcohols, such as glycerol and trimethylolpropane), polyamines, and combinations thereof. Non-limiting examples of polyamine crosslinking agents include diethyltoluenediamine, chlorodiaminobenzene, diethanolamine, diisopropanolamine, triethanolamine, tripropanolamine, 1,6-hexanediamine, and combinations thereof. Typical diamine crosslinking agents comprise twelve carbon atoms or fewer, more commonly seven or fewer. Other cross-linking agents include various tetrols, such as erythritol and pentaerythritol, pentols, hexols, such as dipentaerythritol and sorbitol, as well as alkyl glucosides, carbohydrates, polyhydroxy fatty acid esters such as castor oil and polyoxy alkylated derivatives of poly-functional compounds having three or more reactive hydrogen atoms, such as, for example, the reaction product of trimethylolpropane, glycerol, 1,2,6-hexanetriol, sorbitol and other polyols with ethylene oxide, propylene oxide, or other alkylene epoxides or mixtures thereof, e.g., mixtures of ethylene and propylene oxides.

Non-limiting examples of chain extenders include, but are not limited to, compounds having hydroxyl or amino functional group, such as glycols, amines, diols, and water. Specific non-limiting examples of chain extenders include ethylene glycol, diethylene glycol, propylene glycol, dipropylene glycol, 1,4-butanediol, 1,3-butanediol, 1,5-pentanediol, neopentyl glycol, 1,6-hexanediol, 1,10-decanediol, 1,12-dodecanediol, ethoxylated hydroquinone, 1,4-cyclohexanediol, N-methylethanolamine, N-methylisopropanolamine, 4-aminocyclohexanol, 1,2-diaminoethane, 2,4-toluenediamine, or any mixture thereof.

Catalyst

The catalyst component can affect the reaction rate and can exert influence on the open celled structures and the physical properties of the foam. The proper selection of catalyst (or catalysts) appropriately balance the competing interests of the blowing and polymerization reactions. A correct balance is needed due to the possibility of foam collapse if the blow reaction proceeds relatively fast. On the other hand, if the gelation reaction overtakes the blow reaction, foams with closed cells might result and this might lead to foam shrinkage or 'pruning'. Catalyzing a polyurethane foam, therefore, involves choosing a catalyst package in such a way that the gas produced becomes sufficiently entrapped in the polymer. The reacting polymer, in turn, must have sufficient strength throughout the foaming process to maintain its structural integrity without collapse, shrinkage, or splitting.

The catalyst component is selected from the group consisting of tertiary amines, organometallic derivatives or salts of, bismuth, tin, iron, antimony, cobalt, thorium, aluminum, zinc, nickel, cerium, molybdenum, vanadium, copper, manganese and zirconium, metal hydroxides and metal carboxylates. Tertiary amines may include, but are not limited to, triethylamine, triethylenediamine, N,N,N',N'-tetramethylethylenediamine, N,N,N',N'-tetraethylethylenediamine, N-methylmorpholine, N-ethylmorpholine, N,N,N',N'-tetramethylguanidine, N,N,N',N'-tetramethyl-1,3-butanediamine, N,N-dimethylethanolamine, N,N-diethylethanolamine. Suitable organometallic derivatives include di-n-butyl tin bis(mercaptoacetic acid isooctyl ester), dimethyl tin dilaurate, dibutyl tin dilaurate, dibutyl tin sulfide, stannous octoate, lead octoate, and ferric acetylacetonate. Metal hydroxides may include sodium hydroxide and metal carboxylates may include potassium acetate, sodium acetate or potassium 2-ethylhexanoate.

Blowing Agents

Polyurethane foam production may be aided by the inclusion of a blowing agent to produce voids in the polyurethane matrix during polymerization. The blowing agent promotes the release of a blowing gas which forms cell voids in the polyurethane foam. The blowing agent may be a physical blowing agent or a chemical blowing agent. The physical blowing agent can be a gas or liquid, and does not chemically react with the polyisocyanate composition. The liquid physical blowing agent typically evaporates into a gas when heated, and typically returns to a liquid when cooled. The physical blowing agent typically reduces the thermal conductivity of the polyurethane foam. Suitable physical blowing agents for the purposes of the invention may include liquid carbon dioxide, acetone, and combinations thereof. The most typical physical blowing agents typically have a zero ozone depletion potential. Chemical blowing agents refers to blowing agents which chemically react with the polyisocyanate composition.

Suitable blowing agents may also include compounds with low boiling points which are vaporized during the exothermic polymerization reaction. Such blowing agents are generally inert or they have low reactivity and therefore it is likely that they will not decompose or react during the polymerization reaction. Examples of blowing agents include, but are not limited to, water, carbon dioxide, nitrogen gas, acetone, and low-boiling hydrocarbons such as cyclopentane, isopentane, n-pentane, and their mixtures. Previously, blowing agents such as chlorofluorocarbons (CFCs), hydrofluorocarbons (HFCs), hydrochlorofluorocarbons (HCFCs), fluoroolefins (FOs), chlorofluoroolefins (CFOs), hydrofluoroolefins (HFOs), and hydrochlorfluoroolefins (HCFOs), were used, though such agents are not as environmentally friendly. Other suitable blowing agents include water that reacts with isocyanate to produce a gas, carbamic acid, and amine, as shown below in Scheme 9.

Scheme 9. Blowing reaction during the polymerization process

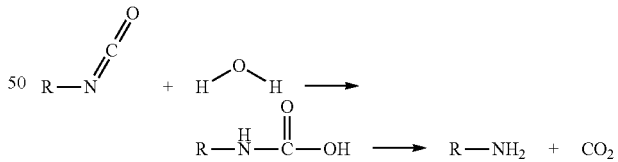

Various methods were adopted in the present study to produce rigid and flexible foams from fractions of PMTAG and Polyols derived therefrom.

Cell Stabilizers

Cell stabilizers may include, for example, silicone surfactants or anionic surfactants. Examples of suitable silicone surfactants include, but are not limited to, polyalkylsiloxanes, polyoxyalkylene polyol-modified dimethylpolysiloxanes, alkylene glycol-modified dimethylpolysiloxanes, or any combination thereof. Suitable anionic surfactants include, but are not limited to, salts of fatty acids, salts of sulfuric acid esters, salts of phosphoric acid esters, salts of sulfonic acids, and combinations of any of these. Such surfactants provide a variety of functions, reducing surface tension, emulsifying incompatible ingredients, promoting bubble nucleation during mixing, stabilization of the cell walls during foam expansion, and reducing the defoaming effect of any solids added. Of these functions, a key function is the stabilization of the cell walls, without which the foam would behave like a viscous boiling liquid.

Additional Additives

If desired, the polyurethane foams can have incorporated, at an appropriate stage of preparation, additives such as pigments, fillers, lubricants, antioxidants, fire retardants, mold release agents, synthetic rubbers and the like which are commonly used in conjunction with polyurethane foams.

Flexible and Rigid Foam Embodiments

In some embodiments, the polyurethane foam may be a flexible foam, where such composition comprises (i) at least one polyol composition derived from a fraction of a natural oil based metathesized triacylglycerols component; (ii) at least one polyisocyanate component, wherein the ratio of hydroxy groups in said at least one polyol to isocyanate groups in said at least one polyisocyanate component is less than 1; (iii) at least one blowing agent; (iv) at least one cell stabilizer component; and (v) at least one catalyst component; wherein the composition has a wide density range, which can be between about 85 kgm$^{-3}$ and 260 kgm$^{-3}$, but can in some instances be much wider.

In other embodiments, the polyurethane foam may be a rigid foam, where the composition comprises (i) at least one polyol derived from a fraction of a natural oil based metathesized triacylglycerols component; (ii) at least one polyisocyanate component, wherein the ratio of hydroxy groups in said at least one polyol to isocyanate groups in said at least one polyisocyanate component is less than 1; (iii) at least one cross-linking component (iv) at least one blowing agent; (v) at least one cell stabilizer component; and (vi) at least one catalyst component; wherein the composition has a wide density range, which can be between about 85 kgm$^{-3}$ and 260 kgm$^{-3}$, but can in some instances be much wider.

Waxes and Cosmetics

In certain aspects, the disclosure provides wax compositions, which includes polyester polyols made by the methods of any of the foregoing aspects and embodiments, or which is derived from a polyester polyol made by the methods of any of the foregoing aspects and embodiments.

In certain aspects, the disclosure provides personal care compositions, such as cosmetics compositions, which includes polyester polyols made by the methods of any of the foregoing aspects and embodiments, or which is derived from a polyester polyol made by the methods of any of the foregoing aspects and embodiments.

The foregoing detailed description and accompanying figures have been provided by way of explanation and illustration, and are not intended to limit the scope of the invention. Many variations in the present embodiments illustrated herein will be apparent to one of ordinary skill in the art, and remain within the scope of the invention and their equivalents. The skilled person in the art will recognize many variations that are within the spirit of the invention and scope of any current or future claims.

The invention claimed is:

1. A method of making a fractionated triacylglycerol polyol from a natural oil, the method comprising:
providing a metathesized triacylglycerol composition, which is formed by the cross-metathesis of the natural oil with lower-weight olefins, and which comprises triglyceride compounds having one or more carbon-carbon double bonds;
reacting at least a portion of the carbon-carbon double bonds in the compounds comprised by the metathesized triacylglycerol composition to form a triacylglycerol polyol composition; and
separating the triacylglycerol polyol composition into a liquid phase and a solid phase from to form a fractionated triacylglycerol polyol composition, which comprises compounds having one or more carbon-carbon double bonds.

2. The method of claim 1, wherein the lower-weight olefins comprise $C_2$-$C_6$ olefins.

3. The method of claim 1, wherein the lower-weight olefins comprise $C_2$-$C_6$ alpha olefins.

4. The method of claim 3, wherein the lower-weight olefins comprise ethylene or 1-butene.

5. The method of claim 4, wherein the lower-weight olefins comprise 1-butene.

6. The method of claim 1, wherein the natural oil is selected from canola oil, soybean oil, palm oil, and combinations thereof.

7. The method of claim 1, wherein the metathesized triacylglycerol composition comprises triglycerides that comprise 9-decenoate residues.

8. The method of claim 1, wherein the metathesized triacylglycerol composition comprises triglycerides that comprise 9-dodecenoate residues.

9. The method of claim 1, wherein the reacting comprises epoxidizing at least a portion of the carbon-carbon double bonds in the compounds comprised by the metathesized triacylglycerol composition to form a triacylglycerol polyol, followed by hydroxylating at least a portion of the epoxide groups formed by the epoxidizing step.

10. The method of claim 9, wherein the epoxidizing comprises reacting at least a portion of the carbon-carbon double bonds in the compounds comprised by the metathesized triacylglycerol composition with a peroxyacid.

11. The method of claim 9, wherein the reacting further comprises, after the epoxidizing and before the hydroxylating, neutralizing the product of the epoxidizing step.

12. The method of claim 9, wherein the epoxidizing comprises reacting at least a portion of the carbon-carbon double bonds in the compounds comprised by the metathesized triacylglycerol composition with formic acid or acetic acid.

13. The method of claim 1, wherein the separating comprises:
melting the triacylglycerol polyol composition;
cooling the melted triacylglycerol polyol composition to form a triacylglycerol polyol composition having the liquid phase and the solid phase; and
separating at least a portion of the liquid phase to form the fractionated triacylglycerol polyol composition.

14. The method of claim 1, wherein the separating comprises:
melting the triacylglycerol polyol composition;
cooling the melted triacylglycerol polyol composition to form a triacylglycerol polyol composition having the liquid phase and the solid phase; and
separating at least a portion of the solid phase to form the fractionated triacylglycerol polyol composition.

15. The method of claim 1, wherein the separating comprises:
dissolving the triacylglycerol polyol composition in a solvent;
cooling the dissolved triacylglycerol polyol composition to crystallize a portion of the triacylglycerol polyol composition to form the solid phase; and separating at least a portion of the dissolved triacylglycerol polyol composition from the crystallized triacylglycerol polyol composition to form the fractionated triacylglycerol polyol composition.

16. The method of claim 1, wherein the separating comprises:
dissolving the triacylglycerol polyol composition in a solvent;
cooling the dissolved triacylglycerol polyol composition to crystallize a portion of the triacylglycerol polyol composition to form the solid phase; and
separating at least a portion of the crystallized triacylglycerol polyol composition from the dissolved triacylglycerol polyol composition to form the fractionated triacylglycerol polyol composition.

17. The method of claim 15, wherein the solvent comprises ethyl acetate, hexane, or tetrahydrofuran.

18. The method of claim 15, wherein the solvent comprises dichloromethane, ethyl acetate, or tetrahydrofuran.

19. The method of claim 1, wherein the fractionated triacylglycerol polyol composition has an iodine value that is no less than that of the triacylglycerol polyol composition.

20. The method of claim 1, wherein the fractionated triacylglycerol polyol composition has an iodine value that is less than that of the triacylglycerol polyol composition.

* * * * *